United States Patent [19]

Gajewski

[11] Patent Number: 4,826,841

[45] Date of Patent: May 2, 1989

[54] ALKANOYL ANILIDES AS PESTICIDES

[75] Inventor: Robert P. Gajewski, Indianapolis, Ind.

[73] Assignee: Eli Lilly and Company, Indianapolis, Ind.

[21] Appl. No.: 836,658

[22] Filed: Mar. 5, 1986

Related U.S. Application Data

[63] Continuation-in-part of Ser. No. 720,236, Apr. 5, 1985, abandoned.

[51] Int. Cl.$^4$ .................. A01N 37/220; A01N 37/24; A01N 43/40; A01N 43/84
[52] U.S. Cl. ........................ 514/237.5; 514/237.8; 514/354; 514/357; 514/423; 514/427; 514/522; 514/535; 514/613; 514/626; 514/628
[58] Field of Search ............. 514/234, 521, 628, 352, 514/522, 535, 613, 626, 237.5, 237.8, 354, 357, 423, 427

[56] References Cited

U.S. PATENT DOCUMENTS 3,839,446 10/1974 Teach ........................ 260/562 A

FOREIGN PATENT DOCUMENTS 197756 10/1986 European Pat. Off. .
59-42368 3/1984 Japan .
1026922 4/1966 United Kingdom .
1347076 2/1974 United Kingdom .

OTHER PUBLICATIONS

Derwent 85-153144/26.
Derwent 85-159608/27.
Derwent 85-159610/27.
Derwent 84-290758/47.
Derwent 85-154141/26.
Derwent 85-052338/09.
Derwent 85-111873/19.
Chem. Abst. 64:2022a.
Chemical Abstracts 64, #11, 15861a.

Primary Examiner—Anton H. Sutto
Attorney, Agent, or Firm—Kathleen R. S. Page; Leroy Whitaker

[57] ABSTRACT

The present invention is in alkanoyl anilides exhibiting insecticidal and arachnicidal activity, wherein the alkanoyl is both branched and substantially or totally fluorinated.

64 Claims, No Drawings

ALKANOYL ANILIDES AS PESTICIDES

CROSS REFERENCE TO RELATED APPLICATION

This is a continuation-in-part of my copending application Ser. No. 720,236 filed Apr. 5, 1985 now abandoned.

BRIEF SUMMARY OF THE INVENTION

The present invention is in alkanoyl anilides of which the alkanoyl is both branched and substantially or totally fluorinated. These anilides exhibit excellent insecticidal and arachnicidal activity. The invention therefore also includes methods employing, and formulations comprising, these compounds as insecticides and arachnicides.

The novel alkanoyl anilides are defined by the following formulae:

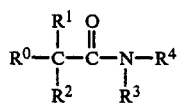

I

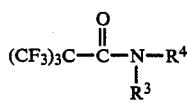

II and

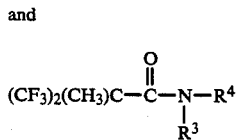

III wherein
$R^0$ represents
  bromo,
  chloro, or
  fluoro;
$R^1$ represents
  $CF_3$,
  $C_2F_5$,
  $C_3F_7$, or
  a n-, iso-, or sec-$C_4F_9$;
$R^2$ represents
  $CF_3$, $C_2F_5$, $C_3F_7$, or,
  when $R^0$ represents fluoro, $R^2$ can additionally represent
  —$OR_f$,
  —$N(R_f)_2$,
  —CN,
  —$CF_2$—$OR_f$, or
  —$CF_2$—$N(R_f)_2$
  and each $R_f$ independently represents perfluoroloweralkyl of $C_1$–$C_4$ or, in —$N(R_f)_2$ both $R_f$ groups can be taken together with the N and constitute perfluoropyrrolidino, perfluoropiperidino, perfluoromorpholino, or N-(trifluoromethyl)perfluoropiperazino;
$R^3$ represents
  hydrogen, or
  methyl; and
$R^4$ represents
  5-nitro-2-pyridyl,
  thiocyanatophenyl bearing a single additional substituent which is fluoro, chloro, bromo, iodo, or nitro, or
  substituted aryl of the formula

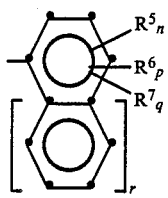

wherein each $R^5$ independently represents
  bromo,
  chloro, or
  fluoro;
each $R^6$ independently represents
  iodo,
  nitro,
  cyano,
  trifluoromethyl,
  fluorosulfonyl,
  methylsulfonyl,
  ethylsulfonyl,
  carbomethoxy, or
  carboethoxy;
$R^7$ represents
  methyl, or,
  when two $R^6$ moieties represent nitro at the 2- and 4-positions, $R^7$ can additionally represent $C_1$–$C_4$ alkoxy or $C_1$–$C_4$ alkylthio located at only the 3- or 5-position;
n represents 0–5; p represents 0–2 except that p can additionally represent 3 but only where two $R^6$ moieties represent nitro and a third $R^6$ moiety represents trifluoromethyl; q represents 0, or, when at least one $R^5$, nitro, or fluorosulfonyl group is present, 1;
r represents 0 or 1; and the sum of n, p, and q is:
  2–5 when each of p, q, and r is 0;
  2–3 when any one of p, q, or r is at least 1, except that when p is one and $R^6$ is 4-nitro, the sum of n and p can additionally be 1;
or a sodium, potassium, or ammonium salt of a foregoing compound, wherein ammonium is of the following formula

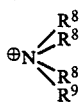

wherein each $R^8$ independently represents alkyl of $C_1$–$C_{20}$, benzyl, 2-hydroxyethyl, 2-hydroxypropyl, or 3-hydroxypropyl; and $R^9$ represents hydrogen or $R^8$, the total number of carbon atoms in all $R^8$ and $R^9$ moieties being from 12 to 60, except that when one or more $R^8$ groups are 2-hydroxyethyl, 2-hydroxypropyl, or 3-hydroxypropyl, the total number of carbon atoms in all $R^8$ and $R^9$ moieties can be from 6 to 60.

DETAILED DESCRIPTION OF THE INVENTION

Synthesis

The present compounds are prepared in conventional procedures for the preparation of carboxanilides. A preferred method is the reaction of the appropriate alkanoyl halide:

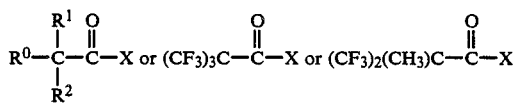

with the desired aniline, 1-aminonaphthalene, or 2-amino-5-nitropyridine, of the formula

Preferably the halide is fluoride. In carrying out this reaction, the reactants are combined in a reaction solvent. Various solvents can be employed, including toluene, acetonitrile, diethyl ether, tetrahydrofuran, and halogenated solvents such as methylene chloride. In general, diethyl ether and halogenated solvents are preferred. A halogenated solvent can sometimes serve as the solvent in a "one-pot" reaction to make the aniline starting material which is thereafter converted to the final product of the invention. In other particulars, the reaction is conventional. An HF acceptor is provided to the reaction mixture; typically triethylamine is used. The reaction consumes the reactants and the HF acceptor in equimolar amounts. The reaction goes forward over a wide temperature range, such as from 10° to 110° C.; however, the reaction is most conveniently carried out at temperatures of about 20° to 70° C. Workup of the reaction mixture to isolate the product is carried out in conventional procedures.

The alkanoyl halides employed as starting materials in this reaction route are generally prepared by electrochemical fluorination and therefore often contain isomers. In view of the requirement of the present invention for branching alpha to the carbonyl, it is often desirable to purify the anilide products to remove straight-chain isomers. It has been found that this can generally be achieved by selective hydrolysis of the straight-chain carboxanilides, and separation of the water soluble K or Na salt of the branched chain carboxanilide from the precipitated aniline. This is illustrated by Examples 2, 3, 8, and 13 below.

An alternate procedure is available for the preparation of those compounds of formula I wherein $R^0$ represents fluoro, both $R^1$ and $R^2$ represent trifluoromethyl, and $R^3$ represents hydrogen; however, this procedure is less favored than the proceding one. The procedure involves the reaction of an olefin, hexafluoropropene, and an isocyanate in the presence of a fluoride such as KF, NaF, or cesium fluoride:

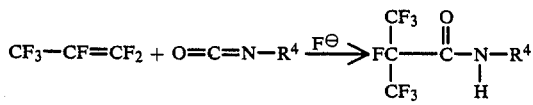

The reaction is carried out in a reaction solvent such as DMF, DMSO, or diglyme, under pressure of 5–40 psig. The reaction goes forward over a range of temperatures, such as from 30° to 70° C. The reaction requires one mole of isocyanate, three or more moles of KF, NaF, or cesium fluoride, and three to ten or more moles of hexafluoropropene. Workup is conventional.

Those compounds of the present invention in which $R^3$ represents methyl are preferably prepared from the corresponding $R^3$=hydrogen compounds. This methylation reaction is carried out in any of the known conventional methods for methylation. Typically, methyl iodide is employed as the reagent, and the reaction is carried out in a suitable solvent, such as acetone, with a base such as potassium carbonate. Equimolar amounts of the reactants are consumed, but the ethyl iodide is preferably used in excess. The reaction goes forward over a wide range of temperatures, but is most conveniently carried out at room temperatures of about 25° to 35° C. Workup is by conventional procedures.

The present invention also includes salts of the parent compounds. These salts are prepared in entirely conventional methods. The sodium and potassium salts are prepared by reacting the corresponding parent compounds with sodium or potassium hydroxide; the ammonium salts can be obtained by reacting the parent compound with a compound of the formula

or by reacting a sodium salt of a present compound with

(where X=Br, Cl, or F).

The synthesis of the present compounds is further taught by the following illustrative examples.

EXAMPLE 1

2'-Bromo-4'-nitro-2,3,3,3-tetrafluoro-2-(trifluoromethyl)propionanilide (olefin process).

Potassium fluoride (23 grams; 0.4 mole) which was dried by heating strongly with a bunsen burner in a porcelain crucible and subsequently powdered, was added to 200 ml of a DMF solution of 2-bromo-4-nitrophenyl isocyanate (6 grams; 0.025 mole). The mixture was placed in a pressure vessel, purged with a small stream of hexafluoropropene, and heated to 70° C. while adding hexafluoropropene from a pre-weighed supply cylinder at 10–20 psig. A pressure drop occurred as the gas reacted, and the remaining hexafluoropropene was added intermittently until the supply cylinder was empty; heating was continued at 65°–70° C. for 2½ hours with pressure stabilized at 5 psig. The reaction vessel was then cooled and the solution poured off and extracted with hexane. The DMF solution was poured into water and filtered. The solid products were taken up in chloroform, dried over sodium sulfate, filtered, evaporated, and chromatographed on silica gel with ethyl acetate/hexane (1:5). The front-running product was collected; H-NMR of this product indicated the desired product. The material was then chromatographed on silica gel with gradient elution from 100% hexane to 100% ethyl acetate.

The foregoing procedures yielded a waxy solid, m.p. 57°–59° C., yield 1.65 grams (16%). The identity of the product was confirmed by MS, H-NMR, and $F^{19}$-NMR.

Analysis calculated for $C_{10}H_4BrF_7N_2O_3$: Theory: C, 29.08; H, 0.98; N, 6.78; Found: C, 29.31; H, 0.83; N, 6.58.

EXAMPLE 2

2'-Bromo-4'-nitro-2,3,3,3-tetrafluoro-2-(trifluoromethyl)propionanilide (alkanoyl fluoride process, with isomer purification).

2-Bromo-4-nitroaniline (141 grams; 0.65 mole) was dissolved in 3.5 liters of diethyl ether, dried over sodium sulfate, and filtered. Triethylamine (71 grams; 0.070 mole) was added with stirring. A mixture of 2,2,3,3,4,4,4-heptafluorobutyryl fluoride, 2,3,3,3-tetrafluoro-2-(trifluoromethyl)propionyl fluoride, HF, and inert gases were employed. The mixture was believed to contain 70% of chemically active acyl fluorides; 100 grams of this mixture were add under a dry ice/acetone condensor. The reaction mixture was left to stand overnight (about 17 hours) and an additional amount of the mixture was added to a total of 210 grams (0.70 mole).

Water was added to the reaction mixture, then dilute ice/HCl until the pH of the aqueous layer was acidic. The water layer was decanted off. The diethyl ether layer was dried over magnesium sulfate and the solvent evaporated under vacuum.

The solid residue was taken up in 800 ml of ethanol, and treated with potassium carbonate at room temperature, with magnetic stirring. Sixty-eight grams of $K_2CO_3$ was added initially, followed by 23 g more after 24 hours and 12 g more after 48 hours and stirred for a total of 64 hours. The ethanol was evaporated under vacuum, and the solids were triturated three times with aqueous potassium carbonate. The solution was filtered and the filtrate was acidified below 25° C. with HCl. The product was filtered, washed with water, dissolved in methylene chloride, dried, and evaporated. The gas chromatogram of the product indicated less than 1% straight-chain isomer, m.p., 66° C., yield, 178 grams (66%).

Analysis calculated for $C_{10}H_4BrF_7N_2O_3$: Theory: C, 29.08; H, 0.98; N, 6.78; Found: C, 29.30; H, 0.92; N, 6.99.

EXAMPLE 3

2'-Bromo-4'-nitro-2,3,3,3-tetrafluoro-2-(trifluoromethyl)propionanilide (alkanoyl fluoride process, with isomer purification).

2-Bromo-4-nitroaniline (35.84 grams; 0.16 mole), triethylamine (21.15 grams; 0.21 mole), and 250 ml of tetrahydrofuran were added to a 500 ml roundbottom flask equipped with a dry ice/acetone reflux condenser and a gas inlet. The vessel was purged with nitrogen. The same mixture of acyl fluorides used in Example 2 was employed as the reactant in the present example (54.60 grams; 0.18 mole). This mixture was added at a rate allowing a slow reflux. The addition required approximately 90 minutes and the resulting brown solution was stirred for about an hour after the addition was complete.

The reaction mixture was then washed with 60 ml of a 50/50 mixture of water/saturated sodium chloride solution and 40 ml of saturated sodium chloride solution. The aqueous layers were discarded.

One hundred fifty milliliters of 1N sodium hydroxide was then added to the organic layer and 90 ml of volatile material was distilled off at atmospheric pressure. Another 100 ml of 1N sodium hydroxide was added to the solution, and the resulting solution was distilled until the head temperature rose above the boiling point of tetrahydrofuran, 66° C. The pot temperature was held constant until HPLC confirmed the hydrolysis of the straight-chain product by the basic solution. The resulting aniline precipitated out at this time and was removed by filtration.

The filtrate was allowed to cool, then washed twice, with 150 ml and 100 ml of methylene chloride. The aqueous layer was separated and placed under vacuum to remove any residual organic solvents. The solution was then placed in an ice bath and the pH was lowered to 7 with concentrated hydrochloric acid. The desired 2'-bromo-4'-nitro-2,3,3,3-tetrafluoro-2-(trifluoromethyl)propionanilide precipitated and was separated by filtration, washed with distilled water, and dried overnight in vacuo at room temperature, 42.95 grams (86.0%) in 99.5% purity by HPLC.

Other compounds of the present invention were prepared by the alkanoyl fluoride procedure except where noted otherwise. Preparations by the alkanoyl fluoride process were isolated as isomer mixtures except as noted in Examples 8 and 13.

These other compounds of the present invention are listed in the following Examples. In each example, the identity of the product was confirmed by H-NMR. The percentage of the desired branched chain isomer in the product, as determined by $F^{19}$-NMR, is also reported.

EXAMPLE 4

2'-Cyano-4'-nitro-2,3,3,3-tetrafluoro-2-(trifluoromethyl)propionanilide, m.p., 100°–101° C., yield 50% (72% branched isomer).

Analysis calculated for $C_{11}H_4F_7N_3O_3$: Theory: C, 36.79; H, 1.12; N, 11.70; Found: C, 37.05; H, 1.22; N, 11.89.

EXAMPLE 5

2'-Methyl-4'-nitro-2,3,3,3-tetrafluoro-2-(trifluoromethyl)propionanilide, m.p., 120°–122° C., yield 22% (93% branched isomer).

Analysis calculated for $C_{11}H_7F_7N_2O_3$: Theory: C, 37.95; H, 2.03; N, 8.05; Found: C, 38.10; H, 1.95; N, 8.26.

EXAMPLE 6

2'-(trifluoromethyl)-4'-nitro-2,3,3,3-tetrafluoro-2-(trifluoromethyl)propionanilide, m.p., 53°–54° C., yield 15% (>95% branched isomer).

Analysis calculated for $C_{11}H_4F_{10}N_2O_3$: Theory: C, 32.85; H, 1.00; N, 6.97; Found: C, 32.79; H, 1.15; N, 7.01.

EXAMPLE 7

2',3',4',5',6',2,3,3,3-Nonafluoro-2-(trifluoromethyl)-propionanilide, m.p., 137°–142° C., yield 85% (60% branched isomer).

Analysis calculated for $C_{10}HF_{12}NO$: Theory: C, 31.68; H, 0.27; N, 3.69; Found: C, 31.42; H, 0.23; N, 3.89.

EXAMPLE 8

2'-Chloro-4'-nitro-2,3,3,3-tetrafluoro-2-(trifluoromethyl)propionanilide, m.p., 52°–53° C., yield 94% (86% branched isomer).

Analysis calculated for $C_{10}H_4ClF_7N_2O_3$: Theory: C, 32.59; H, 1.09; N, 7.60; Found: C, 32.82; H, 0.97; N, 7.63.

This product was purified by treatment with potassium carbonate ethanol, as follows. The product (4 grams; 0.0108 mole) was dissolved in 20 ml of 95% ethanol and potassium carbonate (1.1 gram; 0.008 mole) was added. The mixture was maintained for 5 days at room temperature. The ethanol was then evaporated off at room temperature. Potassium carbonate (1.1 gram) in 50 ml of water was added at 40° C. with vigorous stirring. The mixture was filtered and washed with 40° C. water. The filtrate was cooled, acidified with HCl, filtered, and air dried, yielding 2.8 grams (70% yield) of purified product melting at 67° C. The gas chromatogram and $F^{19}$-NMR confirmed that the product was >99% branched isomer.

EXAMPLE 9

2',3',4',6',2,3,3,3-Octafluoro-2-(trifluoromethyl)propionanilide, m.p., 104°–108° C., yield 31% (78% branched isomer).

Analysis calculated for $C_{10}H_2F_{11}NO$: Theory: C, 33.26; H, 0.56; N, 3.88; Found: C, 33.54; H, 0.78; N, 3.94.

EXAMPLE 10

2',4',5'-Trichloro-2,3,3,3-tetrafluoro-2-(trifluoromethyl)propionanilide, m.p., 69°–72° C., yield 55% (87% branched isomer).

Analysis calculated for $C_{10}H_3Cl_3F_7NO$: Theory: C, 30.60; H, 0.77; N, 3.57; Found: C, 30.69; H, 1.01; N, 3.62.

Another preparation of the same compound was made, m.p., 80°–81° C., yield 67% (91% branched isomer).

Found: C, 30.47; H, 1.04; N, 3.43.

EXAMPLE 11

2',3',5',6',2,3,3,3-Octafluoro-2-(trifluoromethyl)propionanilide, m.p., 94°–99° C., yield 69% (82% branched isomer).

Analysis calculated for $C_{10}H_2F_{11}NO$: Theory: C, 33.26; H, 0.56; N, 3.88; Found: C, 33.06; H, 0.34; N, 4.00.

EXAMPLE 12

2',3',4',5'-Tetrachloro-2,3,3,3-tetrafluoro-2-(trifluoromethyl)propionanilide, m.p., 82°–83° C., yield 18% (95% branched isomer).

Analysis calculated for $C_{10}H_2Cl_4F_7NO$: Theory: C, 28.13; H, 0.47; N, 3.28; Found: C, 28.35; H, 0.52; N, 3.30.

EXAMPLE 13

Preparation #1

2',5'-Dichloro-4'-nitro-2,3,3,3-tetrafluoro-2-(trifluoromethyl)propionanilide was prepared by the olefin procedure, m.p. 80°–82° C., yield 12% (>99% branched isomer).

Analysis calculated for $C_{10}H_3Cl_2F_7N_2O_3$: Theory: C, 29.80; H, 0.75; N, 6.95; Found: C, 29.90; H, 0.53; N, 6.98.

Preparation #2

2',5'-Dichloro-4'-nitro-2,3,3,3-tetrafluoro-2-(trifluoromethyl)propionanilide was also prepared by the alkanoyl fluoride procedure, m.p., 81°–83° C., yield 47% (94% branched isomer). Microanalysis showed Found: C, 30.07; H, 0.53; N, 6.92.

This product was purified by treatment with potassium carbonate, as described above in Example 8, m.p. 83°–85° C., yield 82% of >99% branched isomer.

EXAMPLE 14

2',3'-Dichloro-2,3,3,3-tetrafluoro-2-(trifluoromethyl)propionanilide, m.p., 71°–73° C., yield 32% (99.4% branched isomer).

Analysis calculated for $C_{10}H_4Cl_2F_7NO$: Theory: C, 33.55; H, 1.13; N, 3.91; Found: C, 33.59; H, 1.25; N, 3.95.

EXAMPLE 15

N-(5-Nitro-2-pyridyl)-2,3,3,3-tetrafluoro-2-(trifluoromethyl)propionamide, m.p., 75°–77° C., yield 42% (97% branched isomer).

Analysis calculated for $C_9H_4F_7N_3O_3$: Theory: C, 32.26; H, 1.20; N, 12.54; Found: C, 32.19; H, 1.00; N, 12.45.

EXAMPLE 16

2',6'-Dichloro-4'-nitro-2,3,3,3-tetrafluoro-2-(trifluoromethyl)propionanilide, m.p., 128°–134° C., yield 13% (59% branched isomer).

Analysis calculated for $C_{10}H_3Cl_2F_7N_2O_3$: Theory: C, 29.80; H, 0.75; N, 6.95; Found: C, 29.84; H, 0.97; N, 7.09.

EXAMPLE 17

2'-Methyl-4'-nitro-5'-chloro-2,3,3,3-tetrafluoro-2-(trifluoromethyl)propionanilide, m.p., 114°–116° C., yield 53% (91% branched isomer).

Analysis calculated for $C_{11}H_6ClF_7N_2O_3$: Theory: C, 34.53; H, 1.58; N, 7.32; Found: C, 34.40; H, 1.61; N, 7.31.

EXAMPLE 18

2',4',6'-Trichloro-2,3,3,3-tetrafluoro-2-(trifluoromethyl)propionanilide, m.p., 133°–135° C., yield 33% (87% branched isomer).

Analysis calculated for $C_{10}H_3Cl_3F_7NO$: Theory: C, 30.60; H, 0.77; N, 3.57; Found: C, 30.47; H, 0.92; N, 3.47.

EXAMPLE 19

3,',4',5'-Trichloro-2,3,3,3-tetrafluoro-2-(trifluoromethyl)propionanilide, m.p., 145°–146° C., yield 38% (95% branched isomer).

Analysis calculated for $C_{10}H_3Cl_3F_7NO$: Theory: C, 30.60; H, 0.77; N, 3.57; Found: C, 30.82; H, 1.06; N, 3.50.

EXAMPLE 20

2'-Chloro-5'-nitro-2,3,3,3-tetrafluoro-2-(trifluoromethyl)propionanilide, m.p., 68°–70° C., yield 35% (84% branched isomer).

Analysis calculated for $C_{10}H_4ClF_7N_2O_3$: Theory: C, 32.59; H, 1.09; N, 7.60; Found: C, 32.64; H, 1.33; N, 7.49.

EXAMPLE 21

2',4'-Dinitro-2,3,3,3-tetrafluoro-2-(trifluoromethyl)propionanilide, m.p., 50°–51° C., yield 21% (85% branched isomer).

Analysis calculated for $C_{10}H_4F_7N_3O_5$: Theory: C, 31.68; H, 1.06; N, 11.08; Found: C, 31.42; H, 1.15; N, 10.84.

EXAMPLE 22

2'-Iodo-4'-nitro-2,3,3,3-tetrafluoro-2-(trifluoromethyl)propionanilide, m.p., 107°–110° C., yield 8% (39% branched isomer).

Analysis calculated for $C_{10}H_4IF_7N_2O_3$: Theory: C, 26.11; H, 0.88; N, 6.09; Found: C, 26.28; H, 1.11; N, 5.90.

EXAMPLE 23

2'-Cyano-4'-chloro-2,3,3,3-tetrafluoro-2-(trifluoromethyl)propionanilide, m.p., 90°–91° C., yield 5% (91% branched isomer).

Analysis calculated for $C_{11}H_4ClF_7N_2O$: Theory: C, 37.90; H, 1.16; N, 8.04; Found: C, 38.08; H, 1.10; N, 7.84.

EXAMPLE 24

2'-Bromo-4'-nitro-2,3,3,3-tetrafluoro-2-(trifluoromethyl)propionanilide, tetra-n-propylammonium salt.

2'-Bromo-4'-nitro-2,3,3,3-tetrafluoro-2-(trifluoromethyl)propionanilide, (20 grams of material free of straight-chain isomer; 0.048 mole) was dissolved in 200 ml of acetone. The solution was maintained at room temperature while 2N sodium hydroxide (25 ml; 0.05 mole) and tetra-n-propylammonium bromide (13.5 grams; 0.051 mole) were added. The reaction mixture was stirred for 45 minutes, evaporated at room temperature, and partitioned between methylene chloride/water. The organic phase was washed twice with water, dried over sodium sulfate, and evaporated to dryness, yielding 28.7 grams of the intended salt (99% yield). The identity of the product was confirmed by H-NMR. The product solidified upon standing, m.p., 57°–65° C.

Analysis calculated for $C_{22}H_{31}BrF_7N_3O_3$: Theory: C, 44.16; H, 5.22; N, 7.02; Found: C, 44.14; H, 5.05; N, 6.80.

A second preparation was conducted similarly, and the identity of the product was confirmed by H-NMR. The yield was 9.2 grams (91%), m.p. 72°–75° C.

Found: C, 43.88; H, 4.50; N, 6.83.

A third preparation was similarly conducted, except the starting anilide was only 86% of the desired 2'-bromo-4'-nitro-2,3,3,3-tetrafluoro-2-(trifluoromethyl)propionanilide, the remaining 14% being the corresponding straight-chain isomer. The product of this reaction was an oil. The identity was confirmed by H-NMR.

Found: C, 44.02; H, 5.07; N, 7.02.

Other salts were prepared in similar manner and are reported below. In each preparation, the identity of the product was confirmed by H-NMR. The starting anilide in these preparations, and therefore the corresponding salt as well, was either essentially pure 2'-bromo-4'-nitro-2,3,3,3-tetrafluoro-2-(trifluoromethyl)propionanilide (referred to as "isomer pure") or a mixture of 86% of this compound and 14% of the corresponding straight-chain isomer (referred to as "86% isomer").

EXAMPLE 25

2'-Bromo-4'-nitro-2,3,3,3-tetrafluoro-2-(trifluoromethyl)propionanilide, tetraethylammonium salt, monohydrate, m.p., 112° C., yield 60% (isomer pure).

Analysis calculated for $C_{18}H_{25}BrF_7N_3O_4$: Theory: C, 38.59; H, 4.50; N, 7.50; Found: C, 38.85; H, 4.25; N, 7.48.

EXAMPLE 26

2'-Bromo-4'-nitro-2,3,3,3-tetrafluoro-2-(trifluoromethyl)propionanilide, tetra-n-butylammonium salt, monohydrate, m.p., 78°–80° C., yield 66% (isomer pure).

Analysis calculated for $C_{26}H_{41}BrF_7N_3O_4$: Theory: C, 46.44; H, 6.14; N, 6.25; Found: C, 46.66; H, 6.29; N, 6.12.

EXAMPLE 27

2'-Bromo-4'-nitro-2,3,3,3-tetrafluoro-2-(trifluoromethyl)propionanilide, tetra-n-pentylammonium salt, monohydrate.

Preparation #1, m.p., 55°–57° C., yield 80% (isomer pure).

Analysis calculated for $C_{30}H_{49}BrF_7N_3O_4$: Theory: C, 49.45; H, 6.73; N, 5.77; Found: C, 50.80; H, 6.93; N, 5.69.

F84-1N9-277

Preparation #2, m.p., 54°–56° C., yield 76% (86% isomer).

EXAMPLE 28

2'-Bromo-4'-nitro-2,3,3,3-tetrafluoro-2-(trifluoromethyl)propionanilide, tetra-n-heptylammonium salt, monohydrate, an oil, yield 50% (isomer pure).

Analysis calculated for $C_{38}H_{65}BrF_7N_3O_4$: Theory: C, 54.28; H, 7.79; N, 5.00; Theory*: C, 54.47; H, 7.66; N, 5.11; Found: C, 56.27; H, 8.68; N, 4.59.

*=non hydrate

EXAMPLE 29

2'-Bromo-4'-nitro-2,3,3,3-tetrafluoro-2-(trifluoromethyl)propionanilide, methyltri-n-octylammonium salt, monohydrate, an oil, yield 70% (86% isomer).

Analysis calculated for $C_{35}H_{59}BrF_7N_3O_4$: Theory: C, 52.11; H, 7.20; N, 5.36; Found: C, 52.63; H, 7.39; N, 5.26.

EXAMPLE 30

2'-Bromo-4'-nitro-2,3,3,3-tetrafluoro-2-(trifluoromethyl)propionanilide, methyltris($C_8$–$C_{10}$)ammonium salt, monohydrate, an oil, yield 60% (86% isomer).

EXAMPLE 31

2'-Bromo-4'-nitro-2,3,3,3-tetrafluoro-2-(trifluoromethyl)propionanilide, hexadecyltrimethylammonium salt, monohydrate.

Preparation #1, an oil, yield 48% (isomer pure).

Analysis calculated for $C_{29}H_{47}BrF_7N_3O_4$: Theory: C, 48.74; H, 6.63; N, 5.88; Found: C, 49.03; H, 6.39; N, 5.78.

Preparation #2, an oil, yield 6% (86% isomer).

Found: C, 47.54; H, 6.09; N, 5.90.

EXAMPLE 32

2'-Bromo-4'-nitro-2,3,3,3-tetrafluoro-2-(trifluoromethyl)propionanilide, octadecyltrimethylammonium salt, m.p., 45°–48° C., yield 52% (86% isomer).

Analysis calculated for $C_{31}H_{49}BrF_7N_3O_3$: Theory: C, 51.38; H, 6.76; N, 5.80; Found: C, 52.03; H, 6.67; N, 5.67.

EXAMPLE 33

2'-Bromo-4'-nitro-2,3,3,3-tetrafluoro-2-(trifluoromethyl)propionanilide, benzyltri-n-butylammonium salt, monohydrate, an oil, yield 14% (86% isomer).

Analysis calculated for $C_{29}H_{39}BrF_7N_3O_4$: Theory: C, 49.30; H, 5.56; N, 5.95; Found: C, 50.21; H, 5.96; N, 5.64.

EXAMPLE 34

2'-Bromo-4'-nitro-2,3,3,3-tetrafluoro-2-(trifluoromethyl)propionanilide, dimethylbis($C_{18}$–$C_{22}$)ammonium salt, monohydrate, m.p., 65°–70° C., yield 48% (86% isomer).

EXAMPLE 35

2'-Bromo-4'-nitro-2,3,3,3-tetrafluoro-2-(trifluoromethyl)propionanilide, dimethylbis($C_{10}$–$C_{18}$)ammonium salt, an oil, yield 42% (isomer pure).

EXAMPLE 36

2'-Bromo-4'-nitro-2,3,3,3-tetrafluoro-2-(trifluoromethyl)propionanilide, dimethylbis($C_{14}$-$C_{18}$)ammonium salt, monohydrate, an oil, yield 45% (86% isomer).

EXAMPLE 37

2'-Bromo-4'-nitro-2,3,3,3-tetrafluoro-2-(trifluoromethyl)propionanilide, tributylammonium salt, m.p., 58°-60° C., yield 87% (isomer pure).

Analysis calculated for $C_{22}H_{31}BrF_7N_2O_3$: Theory: C, 44.15; H, 5.18; N, 7.02; Found: C, 43.27; H, 3.47; N, 6.96.

Except where noted otherwise, the following additional examples were prepared by the foregoing procedures.

EXAMPLE 38

4'-Nitro-2,3,3,3-tetrafluoro-2-(trifluoromethyl)propionanilide, m.p., 112°-115° C., yield 60% (85% branched isomer).

Analysis calculated for $C_{10}H_5F_7N_2O_3$: Theory: C, 35.95; H, 1.51; N, 8.38; Found: C, 36.21; H, 1.50; N, 8.39.

EXAMPLE 39

2'-Chloro-5'-(fluorosulfonyl)-2,3,3,3-tetrafluoro-2-(trifluoromethyl)propionanilide, m.p., 63°-65° C., yield 33% (87% branched isomer).

Analysis calculated for $C_{10}H_4ClF_8NO_3S$: Theory: C, 29.61; H, 0.99; N, 3.45; Found: C, 29.88; H, 0.98; N, 3.27.

EXAMPLE 40

N-(4-Nitro-1-naphthyl)-2,3,3,3-tetrafluoro-2-(trifluoromethyl)propionamide, m.p., 127°-128° C., yield 5% (80% branched isomer).

Analysis calculated for $C_{14}H_7F_7N_2O_3$: Theory: C, 43.77; H, 1.84; N, 7.29; Found: C, 43.96; H, 1.82; N, 7.52.

EXAMPLE 41

2'-Bromo-4'-chloro-6'-cyano-2,3,3,3-tetrafluoro-2-(trifluoromethyl)propionanilide, an oil, yield 45% (53% branched isomer).

Analysis calculated for $C_{11}H_3BrClF_7N_2O$: Theory: C, 30.91; H, 0.71; N, 6.55; Found: C, 31.15; H, 0.99; N, 6.30.

EXAMPLE 42

3'-Chloro-4'-nitro-2,3,3,3-tetrafluoro-2-(trifluoromethyl)propionanilide, m.p., 55°-57° C., yield 9% (73% branched isomer).

Analysis calculated for $C_{10}H_4ClF_7N_2O_3$: Theory: C, 32.59; H, 1.09; N, 7.60; Found: C, 32.55; H, 1.34; N, 7.30.

EXAMPLE 43

2'-Bromo-4'-nitro-2,3,3,3-tetrafluoro-2-(trifluoromethyl)propionanilide was reacted with methyl iodide, in acetone and in the presence of potassium carbonate, yielding N-methyl-2'-bromo-4'-nitro-2,3,3,3-tetrafluoro-2-(trifluoromethyl)propionanilide, an oil, yield 70% (>99% branched isomer).

Analysis calculated for $C_{11}H_6BrF_7N_2O_3$: Theory: C, 30.94; H, 1.42; N, 6.56; Found: C, 31.01; H, 1.28; N, 6.77.

EXAMPLE 44

2'-Bromo-4'-nitro-6'-cyano-2,3,3,3-tetrafluoro-2-(trifluoromethyl)propionanilide, m.p., 109°-111° C., yield 10% (30% branched isomer).

Analysis calculated for $C_{11}H_3BrF_7N_3O_3$: Theory: C, 30.16; H, 0.69; N, 9.59; Found: C, 30.41; H, 0.62; N, 9.81.

EXAMPLE 45

2'-Methyl-3'-nitro-2,3,3,3-tetrafluoro-2-(trifluoromethyl)propionanilide, m.p., 100°-102° C., yield 55% (82% branched isomer).

Analysis calculated for $C_{11}H_7F_7N_2O_3$: Theory: C, 37.95; H, 2.03; N, 8.05; Found: C, 37.68; H, 2.01; N, 8.01.

EXAMPLE 46

2',4'-Dinitro-5'-ethoxy-2,3,3,3-tetrafluoro-2-(trifluoromethyl)propionanilide, m.p., 117°-119° C., was obtained in 10% yield from the attempted purification of crude 2',4'-dinitro-5'-fluoro-2,3,3,3-tetrafluoro-2-(trifluoromethyl)propionanilide with $K_2CO_3$ in ethanol (>99% branched isomer).

Analysis calculated for $C_{12}H_8F_7N_3O_6$: Theory: C, 34.04; H, 1.89; N, 9.93; Found: C, 34.19; H, 1.80; N, 10.15.

EXAMPLE 47

2'-bromo-4'-nitro-2,3,3,3-tetrafluoro-2-(pentafluoroethoxy)propionanilide, yield 51%, in mixture with 2'-bromo-4'-nitro-2,3,3,3-tetrafluoro-3-(pentafluoroethoxy)propionanilide and an unidentified third component.

Analysis calculated for $C_{11}H_4BrF_9N_2O_4$: Theory: C, 27.56; H, 0.84; N, 5.85; Found: C, 27.46; H, 0.91; N, 5.75.

EXAMPLE 48

The mixture from the preceding example was purified by treatment with $K_2CO_3$/ethanol, yielding 2'-bromo-4'-nitro-2,3,3,3-tetrafluoro-2-(pentafluoroethoxy)propionanilide, m.p., 49° C., yield 50% (14% unidentified third component).

Analysis calculated for $C_{11}H_4BrF_9N_2O_4$: Theory: C, 27.58; H, 0.84; N, 5.85; Found: C, 27.80; H, 1.04; N, 6.08.

EXAMPLE 49

2'-Bromo-4'-nitro-2,3,3,3-tetrafluoro-2-(octafluoromorpholino)propionanilide, m.p., 50°-52° C., yield 74% (>99% branched isomer).

Analysis calculated for $C_{13}H_4BrF_{12}N_3O_4$: Theory: C, 27.20; H, 0.70; N, 7.32; Found: C, 27.42; H, 0.75; N, 7.32.

EXAMPLE 50

2'-Bromo-4'-nitro-2,3,3,3-tetrafluoro-2-(heptafluoro-n-propoxy)propionanilide, m.p., 49°-51° C., yield 35%. A minor component of 2'-bromo-4'-nitro-2,3,3,3-tetrafluoro-2-(nonafluoro-n-butoxy)propionanilide was detected by $F^{19}$-NMR.

Analysis calculated for $C_{12}H_4BrF_{11}N_2O_4$: Theory: C, 27.22; H, 0.76; N, 5.29; Found: C, 26.99; H, 0.72; N, 5.55.

EXAMPLE 51

2',4'-Dinitro-2,3,3,3-tetrafluoro-2-(heptafluoro-n-propoxy)propionanilide, an oil, yield 50%. A minor component of 2',4'-dinitro-2,3,3,3-tetrafluoro-2-(nonafluoro-n-butoxy)propionanilide was detected by $F^{19}$-NMR.

Analysis calculated for $C_{12}H_4F_{11}N_3O_6$: Theory: C, 29.11; H, 0.81; N, 8.49; Found: C, 29.31; H, 1.05; N, 8.56.

EXAMPLE 52

2'-Bromo-4'-nitro-2-(trifluoromethyl)-2,3,3,4,4,5,5,5-octafluorovaleranilide, m.p., 39°-40° C., yield 44% (isomer pure).

Analysis calculated for $C_{12}H_4BrF_{11}N_2O_3$: Theory: C, 28.07; H, 0.78; N, 5.46; Found: C, 28.42; H, 0.96; N, 5.67.

EXAMPLE 53

2'-(Trifluoromethyl)-4'-bromo-2,3,3,3-tetrafluoro-2-(trifluoromethyl)propionanilide, m.p., 37°–40° C., yield 49% (81% branched isomer).

Analysis calculated for $C_{11}H_4BrF_{10}NO$: Theory: C, 30.30; H, 0.92; N, 3.21; Found: C, 30.07; H, 1.02; N, 3.20.

EXAMPLE 54

2',5'-Dichloro-4'-nitro-2,3,3,3-tetrafluoro-2-(trifluoromethyl)propionanilide, octadecyltrimethylammonium salt monohydrate, m.p., 80°–82° C., yield 99% (96% branched isomer).

Analysis calculated for $C_{31}H_{50}Cl_2F_7N_3O_4$: Theory: C, 51.81; H, 7.01; N, 5.74; Found: C, 49.75; H, 5.56; N, 5.42.

EXAMPLE 55

2',5'-Dichloro-4'-nitro-2,3,3,3-tetrafluoro-2-(trifluoromethyl)propionanilide, hexadecyltrimethylammonium salt, monohydrate, m.p., 79°–81° C., yield 99% (94% branched isomer).

Analysis calculated for $C_{29}H_{46}Cl_2F_7N_3O_4$: Theory: C, 49.43; H, 6.53; N, 5.96; Found: C, 47.65; H, 6.11; N, 7.16.

EXAMPLE 56

2'-Cyano-4'-nitro-2,3,3,3-tetrafluoro-2-(heptafluoro-n-propoxy)propionanilide, m.p. 96° C., yield 17%. A minor component of 2'-cyano-4'-nitro-2,3,3,3-tetrafluoro-2-(nonafluoro-n-butoxy)propionanilide was detected by $F^{19}$-NMR.

Analysis calculated for $C_{13}H_4F_{11}N_3O_4$: Theory: C, 32.86; H, 0.85; N, 8.84; Found: C, 33.06; H, 1.14; N, 8.69.

EXAMPLE 57

2',4'-Dinitro-5'-fluoro-2,3,3,3-tetrafluoro-2-(heptafluoro-n-propoxy)propionanilide, an oil, yield 62%. A minor component of 2',4'-dinitro-5'-fluoro-2,3,3,3-tetrafluoro-2-(nonafluoro-n-butoxy)propionanilide was detected by $F^{19}$-NMR.

Analysis calculated for $C_{12}H_3F_{12}N_3O_6$: Theory: C, 28.09; H, 0.59; N, 8.19; Found: C, 27.99; H, 0.75; N, 8.27.

EXAMPLE 58

2',4'-Dinitro-2-(trifluoromethyl)-2,3,3,4,4,5,5,5-octafluorovaleranilide, an oil, yield 13%.

Analysis calculated for $C_{12}H_4F_{11}N_3O_5$: Theory: C, 36.08; H, 0.84; N, 8.77; Found: C, 30.36; H, 0.88; N, 8.98.

EXAMPLE 59

2',4'-Dinitro-5'-fluoro-2-(trifluoromethyl)-2,3,3,4,4,5,5,5-octafluorovaleranilide, an oil, yield 58%.

Analysis calculated for $C_{12}H_3F_{12}N_3O_5$: Theory: C, 28.99; H, 0.61; N, 8.45; Found: C, 29.20; H, 0.84; N, 8.71.

EXAMPLE 60

2'-Bromo-4'-chloro-6'-cyano-2,3,3,3-tetrafluoro-2-(heptafluoro-n-propoxy)propionanilide, an oil, yield 51%. A minor component of 2'-bromo-4'-chloro-6'-cyano-2,3,3,3-tetrafluoro-2-(nonafluoro-n-butoxy)propionanilide was detected by $F^{19}$-NMR.

Analysis calculated for $C_{13}H_3BrClF_{11}N_2O_2$: Theory: C, 29.21; H, 0.61; N, 5.68; Found: C, 29.41; H, 0.87; N, 5.48.

EXAMPLE 61

2'-Bromo-4'-nitro-2,3,3,4,4,5,5,6,6,6-decafluoro-2-(pentafluoroethyl)hexananilide.

This compound was prepared from 2,3,3,4,4,5,5,6,6,6-decafluoro-2-(pentafluoroethyl)hexanoic acid by conversion to the acid fluoride by electrochemical fluorination as follows:

In a Teflon jar equipped with a stainless steel condensor maintained at from −40° to −50° C., approximately 80 cc of commercial anhydrous HF underwent a preelectrolysis to remove the last traces of water. An electrode pack of about 2 in$^3$ in size consisting of alternating nickel and carbon steel plates was used under a nitrogen atmosphere at a maximum current density of about 20 ma/cm$^2$ and at or below a cell voltage of 5.2 volts relative to a copper reference electrode. 4.1 g of the acid was added and approximately 0.5 amp hrs was passed. The reaction mixture was extracted with four 20 cc portions of CFCl$_3$, and the extracts were added to 1.6 g of 2-bromo-4-nitroaniline and 1.5 g of triethylamine in 25 cc of methylene chloride. The organic layer was washed with dilute HCl, dried over magnesium sulfate, evaporated, and the residue was chromatographed on silica gel with toluene to give a crude mixture whose $F^{19}$-NMR spectrum was consistent with the desired product. The crude mixture was chromatographed again with ethylacetate/hexane (1:5) to produce 100 mg of the desired anilide, an oil, in 1.6% yield.

Analysis calculated for $C_{14}H_4BrF_{15}N_2O_3$; Theory: C, 27.43; H, 0.66; N, 4.57; Found: C, 27.56; H, 0.73; N, 4.75.

Representative other examples of the present invention include the following compounds:

2'-bromo-4'-nitro-2-chloro-3,3,3-trifluoro-2-(trifluoromethyl)propionanilide

2'-bromo-4'-nitro-2-bromo-3,3,3-trifluoro-2-(trifluoromethyl)propionanilide

2'-bromo-4'-nitro-3,3,3-trifluoro-2,2-bis(trifluoromethyl)propionanilide

2'-bromo-4'-nitro-2,3,3,4,4,4-hexafluoro-2-(trifluoromethyl)butyranilide

2'-bromo-4'-nitro-2,3,3,3-tetrafluoro-2-(trifluoromethoxy)propionanilide

2'-bromo-4'-nitro-2-cyano-2,3,3,3-tetrafluoropropionanilide

2'-bromo-4'-nitro-2,3,3,3-tetrafluoro-2-(bis(pentafluoroethyl)amino)propionanilide 2'-bromo-4'-nitro-2,2-bis(trifluoromethyl)propionanilide 2'-bromo-4'-nitro-2,3,3,3-tetrafluoro-2-(trifluoromethyl)propionanilide, sodium salt 2'-bromo-4'-nitro-2,3,3,3-tetrafluoro-2-(trifluoromethyl)propionanilide, tris(2-hydroxyethyl)ammonium salt 2'-bromo-4'-nitro-2-chloro-3,3,3-trifluoro-2-(trifluoromethyl)propionanilide, tris(2-hydroxypropyl)ammonium salt 2'-bromo-4'-nitro-3,3,3-trifluoro-2,2-bis(trifluoromethyl)propionanilide, tetra(3-hydroxypropyl)ammonium salt 2,3,3,3-tetrafluoro-2-(trifluoromethyl)-N-(2-bromo-4-nitro-1-naphthyl)propionamide 2,3,3-tetrafluoro-2-(trifluoromethyl)-N-(2-bromo-4-nitro-1-naphthyl)propionamide, tetra-n-propylammonium salt

Insecticidal Utility

As noted above, the compounds of the present invention exhibit excellent insecticidal and arachnicidal activity. This activity is illustrated by the following tests.

Mite-Insect Screen

Various representative compounds were evaluated in the mite-insect screen. This screen was conducted with four insect and mite species; the compound of Example 1 was additionally evaluated in a separate test against three species. Each compound was formulated in the following procedure: the compound sample was dissolved in a suitable solvent, typically a 50/50 mixture of reagent grade acetone and 95% ethyl alcohol containing Toximul R and Toximul S (each of these is a sulfonate-nonionic blend of emulsifiers produced by Stepan Chemical Co.), and the solution was thereafter diluted with deionized water to the desired concentration. Specific test methods for various species in the mite-insect screen are set forth below.

Southern Armyworm

Young squash plants (*Cucurbita maxima*, var. Blue Hubbard) were sprayed with a formulation containing the test compound; the spraying was of both the tops and bottoms of the leaves, about 8–10 ml per plant. The plants were then allowed to dry and the leaves removed.

The leaves were placed in 100×20 mm plastic petri dishes containing third-instar larvae of southern armyworm (*Spodoptera eridania* (Cramer), Order Lepidoptera, Family Noctuidae). Two replicates were carried out.

Mortality counts were made four days after the larvae were placed on the treated leaves. Observations were also made to determine any inhibition of feeding.

Twospotted Spider Mite & Melon Aphid

Young squash plants (*Cucurbita maxima*, var. Blue Hubbard) were infested by placing on each cotyledon a bean leaf infested with twospotted spider mite (*Tetranychus urticae* (Koch), Order Acarina, Family Tetranychidae). The plants were held for a day, then sprayed to wetting with a formulation containing the test compound, with one infested cotyledon per treatment. Mortality was determined one day after treatment.

Another cotyledon was similarly infested with approximately 100 nymphs and adults of melon aphid (*Aphis gossypii* Glover, Order Homoptera, Family Aphididae). Mortality was determined one day after spraying.

Corn Rootworm

A presoaked corn seed, 15 grams of dry sandy soil, and 2 ml of tap water were mixed in a one-ounce plastic container. The mixture was then treated with 1 ml of a formulation containing the test compound and subsequently permitted to dry for 6–12 hours. The concentration of each test compound in the soil was 12 ppm. Five larvae of southern corn rootworm (*Diabrotica undecimpunctata howardi* Barber, Order Coleoptera, Family Chrysomelidae) were added to each container, which was then capped and held at 23° C. Mortality to southern corn rootworm and phytotoxicity to the corn seedling were recorded at four days posttreatment.

The compound of Example 1 was tested in the mite-insect screen against only three organisms, southern armyworm, twospotted spider mite, and melon aphid, at test concentrations of 100 ppm and 50 ppm. Employing a scale of 0=no control, to 3=complete control, the compound was rated 0 on southern armyworm at both concentrations, 3 on twospotted spider mite at both test concentrations, and 3 on melon aphid at both concentrations.

Other compounds of the present invention were tested against all four organisms with a formulation containing 200 ppm of the test compound; in the case of corn rootworm test, the resulting concentration of the test compound in the soil was 12 ppm. Results were recorded as percent control. Any inhibition of feed intake was noted as an "X". The results of these tests are recorded in the following table.

TABLE 1
MITE-INSECT SCREEN

| EX. NO. | CORN ROOTWORM PERCENT MORT. | SO.ARMYWORM % CONT. | FEED. IN. | 2SSMITE PERCENT CONT. | MELON APHID PERCENT CONT. |
|---|---|---|---|---|---|
| 1 | 100 | 0 | | 100 | 100 |
| 4 | 60 | 0 | | 100 | 100 |
| 5 | 100 | 0 | | 100 | 20 |
| 6 | 100 | 0 | | 100 | 100 |
| 7 | 100 | 0 | | 0 | 0 |
| 8 | 100 | 0 | | 100 | 70 |
| 9 | 100 | 0 | | 0 | 0 |
| 10 | 100 | 0 | | 0 | 80 |
| 11 | 100 | 0 | | 40 | 0 |
| 12 | 100 | 100 | X | 90 | 90 |
| 13 | 100 | 0 | | 100 | 100 |
| 14 | 0 | 0 | | 40 | 40 |
| 15 | 100 | 0 | | 20 | 0 |
| 16 | 100 | 0 | | 100 | 100 |
| 17 | 100 | 80 | X | 100 | 90 |
| 18 | 100 | 0 | | 40 | 0 |
| 19 | 100 | 100 | X | 60 | 0 |
| 20 | 20 | 0 | | 20 | 30 |
| 21 | 100 | 0 | | 100 | 100 |
| 22 | 100 | 0 | | 100 | 100 |
| 23 | 60 | 0 | | 70 | 30 |
| 24 | 100 | 0 | | 100 | 90 |
| 25 | 100 | 0 | | 100 | 100 |
| 26 | 100 | 0 | | 100 | 100 |
| 27 | 100 | 0 | | 90 | 90 |
| 27 | 100 | 0 | | 100 | 100 |
| 28 | 100 | 0 | | 90 | 90 |
| 29 | 100 | 0 | | 100 | 100 |
| 30 | 100 | 0 | | 100 | 100 |
| 31 | 100 | 0 | | 100 | 100 |
| 31 | 100 | 0 | | 0 | 0 |
| 32 | 100 | 0 | | 100 | 100 |
| 33 | 100 | 60 | | 100 | 100 |
| 34 | 100 | 0 | | 100 | 50 |
| 35 | 100 | 0 | | 0 | 20 |
| 36 | 100 | 0 | | 100 | 90 |
| 37 | 100 | 0 | | 90 | 90 |
| 38 | 0 | 0 | | 0 | 0 |
| 39 | 40 | 0 | | 0 | 0 |
| 40 | 40 | 100 | X | 100 | 50 |
| 41 | 0 | 0 | | 80 | 0 |
| 41 | 100 | 0 | | 80 | 0 |
| 42 | 0 | 0 | | 0 | 0 |
| 43 | 0 | 0 | | 40 | 10 |
| 44 | 0 | 0 | | 100 | 50 |
| 44 | 0 | 0 | | 0 | 0 |
| 45 | 0 | 0 | | 0 | 0 |
| 47 | 100 | 0 | | 80 | 80 |
| 48 | 100 | 0 | | 50 | 50 |
| 49 | 100 | 0 | | 0 | 0 |
| 50 | 100 | 0 | | 100 | 100 |
| 51 | 100 | 0 | | 100 | 100 |
| 51 | 60 | 0 | | 100 | 100 |
| 52 | 100 | 0 | | 100 | 100 |
| 53 | 100 | 0 | | 0 | 0 |
| 54 | 100 | 0 | | 100 | 100 |

TABLE 1-continued

MITE-INSECT SCREEN

| EX. NO. | CORN ROOT-WORM PERCENT MORT. | SO.ARMYWORM % CONT. | SO.ARMYWORM FEED. IN. | 2SSMITE PERCENT CONT. | MELON APHID PERCENT CONT. |
|---|---|---|---|---|---|
| 55 | 100 | 100 | | 100 | 100 |
| 56 | 100 | 0 | | 0 | 0 |

Twospotted Spider Mite

Selected compounds of the present invention were evaluated against twospotted spider mite in a secondary test. For this test, each compound was formulated using the solvent/emulsifier described above for the mite-insect screen. The test procedure was essentially the same as that described above as part of the mite-insect screen.

TABLE II

| Example No. | Twospotted Spider Mite | | | | | | |
|---|---|---|---|---|---|---|---|
| | 500 | 100 | 50 | 10 | 5 | 2.5 | 1.0 ppm |
| 1 | 100 | 89 | | 48 | | | |
| 4 | 100 | 100 | | | | | |
| 4 | 100 | 100 | | 100 | | | |
| 5 | 100 | 100 | | | | | |
| 5 | 100 | 100 | | 75 | | | |
| 5 | 100 | 100 | | 9 | | | |
| 6 | 100 | 100 | | | | | |
| 6 | 100 | 100 | | 91 | | | |
| 6 | 100 | 90 | | 1 | | | |
| 8 | 100 | 92 | | 96 | | | |
| 8 | 30 | 17 | | 2 | | | |
| 11 | 100 | 100 | | 83 | | | |
| 13 | 100 | 100 | | 83 | | | |
| 16 | 100 | 100 | | 40 | | | |
| 17 | 100 | 100 | | 100 | | | |
| 19 | 100 | | | | | | |
| 19 | 100 | | 63 | 3 | | | |
| 21 | 100 | 100 | | 100 | | | |
| 22 | 100 | 100 | | 71 | | | |
| 24 | 100 | 100 | | 94 | | | |
| 24 | 100 | 100 | | 53 | | | |
| 24 | | | | 95 | 32 | | 0 |
| 24 | | | | 23 | 10 | | 0 |
| 25 | 100 | 100 | | | | | |
| 25 | 100 | 99 | | | | | |
| 25 | | | | 100 | 72 | 76 | 0 |
| 25 | | 88 | | 12 | 3 | | 0 |
| 26 | 100 | 100 | | 92 | | | |
| 26 | 100 | 64 | | 65 | | | |
| 26 | | | | 85 | 18 | | 0 |
| 26 | | | | 66 | 5 | | 2 |
| 27 | 100 | 100 | | | | | |
| 27 | 100 | | | | | | |
| 27 | 100 | | | | | | |
| 27 | | 100 | | 27 | 13 | | 3 |
| 27 | | 86 | | 8 | 5 | | 2 |
| 28 | 100 | 100 | | | | | |
| 28 | 96 | 100 | | | | | |
| 28 | | 100 | | 76 | 2 | | 0 |
| 28 | | 100 | | 59 | 9 | | 0 |
| 29 | 100 | 100 | | | | | |
| 29 | | 100 | | 39 | | | 6 |
| 30 | 100 | 96 | | | | | |
| 30 | | 99 | 85 | 12 | | | 1 |
| 31 | 100 | 100 | | 51 | | | |
| 32 | 100 | 100 | | | | | |
| 32 | | 100 | 100 | 56 | | | 0 |
| 33 | 100 | 96 | | 49 | | | |
| 34 | 99 | 100 | | 91 | | | |
| 34 | 100 | 98 | | 13 | | | |
| 34 | 100 | 100 | | | | | |
| 36 | 100 | 100 | | 100 | | | |
| 36 | 100 | 63 | | 13 | | | |
| 37 | 100 | 92 | | 63 | | | |

TABLE II-continued

| Example No. | Twospotted Spider Mite | | | | | | |
|---|---|---|---|---|---|---|---|
| | 500 | 100 | 50 | 10 | 5 | 2.5 | 1.0 ppm |
| 52 | 100 | 15 | 0* | 0 | 0 | | 0 |

*25 ppm, also 0.

Twospotted Spider Mite Pre and Post Application

Two compounds of the present invention were tested further against twospotted spider mite on squash. The formulation and test procedures were as described above except that in some treatments, the formulation containing the test compound was applied to the foliage prior to introduction of the mites ("pre") whereas in other treatments, the formulation containing the test compound was applied to the foliage after the introduction of the mites ("post"). Results were as set forth in the following table.

TABLE III

| Example No. | Twospotted Spider Mite Pre and Post Application | | |
|---|---|---|---|
| | Treatment Rate (ppm) | Applied Before | Applied After |
| 34 | 10 | 94 | 31 |
| | 5 | 45 | 9 |
| | 2.5 | 8 | 4 |
| | 1.0 | 3 | 3 |
| 36 | 10 | 100 | 13 |
| | 5 | 70 | 17 |
| | 2.5 | 14 | 14 |
| | 1.0 | 6 | 0 |

Cotton Bollworm

In another secondary test, selected compounds of the present invention were evaluated against cotton bollworm (*Heliothis zea* Boddie). Each compound undergoing test was formulated using the solvent/emulsifier described above in the mite-insect screen.

Twenty first-instar cotton bollworms were placed in a petri dish containing filter paper, then treated with 2 ml of test compound solution. Bollworms were allowed to remain in the dish for 1 hour, then transferred to media cups.

Twenty-four hours after treatment, the bollworms were observed and the percent mortality determined. Compounds active in an initial test were tested at lower concentrations, by the same procedure. Results were as set forth in the following table.

TABLE IV

| Example No. | Cotton Bollworm | | |
|---|---|---|---|
| | 500 | 100 | 10 ppm |
| 12 | 18 | 8 | |
| 17 | 100 | 100 | |
| 19 | 100 | 80 | |
| 24 | 100 | 100 | 0 |
| 24 | 100 | 87 | 63 |
| 25 | 90 | | |
| 25 | 100 | 100 | 0 |
| 26 | 100 | | |
| 26 | 100 | 90 | 0 |
| 27 | 90 | | |
| 28 | 100 | | |
| 28 | 70 | 40 | 0 |
| 33 | 100 | 100 | |

Corn Leafhopper-Contact

In yet another secondary test, selected compounds were evaluated for their ability to control leafhopper (*Dalbulus maidis* Delong and Wolcott Order Homoptera, Family Cicadellidae) on corn (*Zea mays* Linne). Each compound was dissolved in acetone to produce varying concentration solutions of the compound.

A total of two ml of each solution was then applied to a filter paper in a petri dish lid. After the compound saturated the filter paper, a dental wick moistened with deionized water and a kernel of corn were placed on the filter paper. Ten leafhoppers which had been anesthetized with $CO_2$ were then placed in the dish. Each treated filter paper was covered with a petri dish bottom, ventilated by a 1 cm hole covered with fine mesh screen.

Observations were made 24 hours later to determine percent mortality. Compounds exhibiting activity in the initial test were tested in the same procedures but at lower concentrations. Results were as set forth in the following table.

TABLE V

Corn Leafhopper-Contact

| Example No. | 500 | 200 | 100 | 50 | 25 | 12.5 | 10 | 6.25 | 3.125 | 1 ppm |
|---|---|---|---|---|---|---|---|---|---|---|
| 1 | | 100 | 100 | | | | 90 | | | |
| 4 | | 100 | | | | | | | | |
| 4 | | | 10 | | | | 0 | | | |
| 8 | | | 100 | | | | | | | |
| 8 | | | 100 | 100 | | | 60 | | | |
| 10 | | 100 | | | | | | | | |
| 13 | | 100 | 100 | | | | 70 | | | |
| 16 | 100 | | 80 | | | | 0 | | | |
| 17 | 80 | | 80 | | | | 40 | | | |
| 21 | 100 | | 100 | | | | 80 | | | |
| 22 | 100 | | 100 | | | | 90 | | | |
| 24 | | | 100 | 100 | | | 70 | | | |
| 25 | | | 100 | 100 | | | 80 | | | 30 |
| 25 | | | | 100 | 100 | 100 | | 60 | 60 | |
| 26 | | 100 | 100 | | | | 70 | | | 50 |
| 26 | | | | 100 | 100 | 80 | | 70 | 40 | |
| 27 | | 100 | 100 | | | | 50 | | | 30 |
| 27 | | | | 100 | 80 | 70 | | 60 | 70 | |
| 28 | | | 50 | 70 | | | 40 | | | 0 |
| 29 | | | 100 | | | | 44 | | | 0 |
| 30 | | | 100 | | | | | | | |
| 30 | | | 90 | 90 | | | 60 | | | |
| 31 | | | 100 | | | | | | | |
| 31 | | | 100 | 100 | | | 80 | | | |
| 32 | | | 100 | | | | | | | |
| 32 | | | 100 | 100 | | | 80 | | | |
| 33 | 100 | | 100 | | | | 20 | | | |
| 36 | | | 100 | | | | | | | |
| 36 | | | 100 | 70 | | | 40 | | | |
| 37 | | 100 | 100 | | | | 90 | | | |

Corn Leafhopper-on Corn

Three compounds of the present invention were evaluated for the control of corn leafhopper on corn. Each compound was formulated essentially as described above for the mite-insect screen. The testing procedure was the same as described for the twospotted spider mite except that the host plant was corn. The concentration of each compound in its treating formulation was 200 ppm. The results were as set forth in the following table.

TABLE VI

| Corn Leafhopper - on Corn | |
|---|---|
| Example No. | Percent Control |
| 4 | 100 |
| 6 | 80 |
| 10 | 50 |

Southern Corn Rootworm

In a secondary test, selected compounds were reevaluated against southern corn rootworm. The test method was the same as described above as part of the mite-insect screen, with the exception that the compounds were tested at differing concentrations, that two replicates per treatment were carried out, and that mortality ratings were made at differing numbers of days after treatment. The results were as set forth in the following table.

TABLE VII

Corn Rootworm

| Example No. | PPM of Compound in soil | Percent Control of Corn Rootworm | Days Post-Treatment |
|---|---|---|---|
| 1 | 3.0 | 100 | 2 |
| | 1.5 | 100 | 2 |
| | 0.75 | 100 | 2 |
| | 0.38 | 100 | 2 |
| | 0.19 | 30 | 2 |
| | 0.09 | 40 | 2 |
| | 3.0 | 100 | 4 |
| | 1.5 | 100 | 4 |
| | 0.75 | 100 | 4 |
| | 0.38 | 100 | 4 |
| | 0.19 | 90 | 4 |
| | 0.09 | 60 | 4 |
| | 0.75* | 100 | 1 |
| | 0.38* | 100 | 1 |
| | 0.19* | 85 | 1 |
| | 0.09* | 0 | 1 |

TABLE VII-continued

| Example No. | PPM of Compound in soil | Percent Control of Corn Rootworm | Days Post-Treatment |
|---|---|---|---|
|  | 0.75* | 100 | 3 |
|  | 0.38* | 100 | 3 |
|  | 0.19* | 90 | 3 |
|  | 0.09* | 35 | 3 |
| 5 | 0.75 | 30 | 3 |
|  | 0.38 | 0 | 3 |
|  | 0.19 | 0 | 3 |
|  | 0.09 | 0 | 3 |
| 6 | 0.75 | 100 | 3 |
|  | 0.38 | 70 | 3 |
|  | 0.19 | 50 | 3 |
|  | 0.09 | 30 | 3 |
| 7 | 0.75 | 50 | 3 |
|  | 0.38 | 20 | 3 |
|  | 0.19 | 0 | 3 |
|  | 0.09 | 0 | 3 |
| 8 | 12.0 | 100 | 4 |
|  | 6.0 | 100 | 4 |
|  | 3.0 | 100 | 4 |
|  | 1.5 | 100 | 4 |
|  | 0.75 | 100 | 4 |
|  | 0.38 | 100 | 4 |
|  | 0.19 | 40 | 4 |
|  | 0.09 | 0 | 4 |
|  | 0.75 | 100 | 3 |
|  | 0.38 | 100 | 3 |
|  | 0.19 | 50 | 3 |
|  | 0.09 | 10 | 3 |
| 9 | 0.75 | 0 | 3 |
|  | 0.38 | 0 | 3 |
|  | 0.19 | 0 | 3 |
|  | 0.09 | 0 | 3 |
| 10 | 0.75 | 0 | 3 |
|  | 0.38 | 0 | 3 |
|  | 0.19 | 0 | 3 |
|  | 0.09 | 0 | 3 |
| 11 | 0.75 | 50 | 3 |
|  | 0.38 | 10 | 3 |
|  | 0.19 | 0 | 3 |
|  | 0.09 | 0 | 3 |
| 12 | 6.0 | 100 | 3 |
|  | 3.0 | 100 | 3 |
|  | 1.5 | 100 | 3 |
|  | 0.75 | 60 | 3 |
|  | 0.38 | 10 | 3 |
|  | 0.19 | 0 | 3 |
|  | 3.0 | 100 | 3 |
|  | 1.5 | 100 | 3 |
|  | 0.75 | 100 | 3 |
|  | 0.38 | 70 | 3 |
|  | 0.19 | 60 | 3 |
| 13 | 12.0 | 100 | 4 |
|  | 6.0 | 100 | 4 |
|  | 3.0 | 100 | 4 |
|  | 1.5 | 100 | 4 |
|  | 0.75 | 100 | 4 |
|  | 0.38 | 80 | 4 |
| 14 | 48.0 | 80 | 3 |
|  | 24.0 | 50 | 3 |
|  | 12.0 | 10 | 3 |
| 15 | 6.0 | 30 | 3 |
|  | 3.0 | 0 | 3 |
|  | 1.5 | 0 | 3 |
|  | 0.75 | 0 | 3 |
|  | 0.38 | 0 | 3 |
|  | 0.19 | 0 | 3 |
|  | 6.0 | 100 | 4 |
|  | 3.0 | 100 | 4 |
|  | 1.5 | 40 | 4 |
|  | 0.75 | 0 | 4 |
|  | 0.38 | 0 | 4 |
| 16 | 6.0 | 100 | 3 |
|  | 3.0 | 100 | 3 |
|  | 1.5 | 60 | 3 |
|  | 0.75 | 0 | 3 |
|  | 0.38 | 0 | 3 |
|  | 6.0 | 20 | 3 |
|  | 3.0 | 0 | 3 |
|  | 1.5 | 0 | 3 |
|  | 0.75 | 0 | 3 |
|  | 0.38 | 0 | 3 |
|  | 0.19 | 0 | 3 |
| 17 | 6.0 | 100 | 3 |
|  | 3.0 | 100 | 3 |
|  | 1.5 | 100 | 3 |
|  | 0.75 | 60 | 3 |
|  | 0.38 | 0 | 3 |
| 18 | 6.0 | 20 | 3 |
|  | 3.0 | 0 | 3 |
|  | 1.5 | 0 | 3 |
|  | 0.75 | 0 | 3 |
|  | 0.38 | 0 | 3 |
|  | 0.19 | 0 | 3 |
|  | 6.0 | 80 | 4 |
|  | 3.0 | 0 | 4 |
|  | 1.5 | 0 | 4 |
|  | 0.75 | 0 | 4 |
|  | 0.38 | 0 | 4 |
| 19 | 6.0 | 60 | 3 |
|  | 3.0 | 0 | 3 |
|  | 1.5 | 0 | 3 |
|  | 0.75 | 0 | 3 |
|  | 0.38 | 0 | 3 |
|  | 6.0 | 30 | 4 |
|  | 3.0 | 10 | 4 |
|  | 1.5 | 0 | 4 |
|  | 0.75 | 0 | 4 |
|  | 0.38 | 0 | 4 |
|  | 0.19 | 0 | 4 |
|  | 0.09 | 0 | 4 |
| 21 | 6.0 | 90 | 3 |
|  | 3.0 | 30 | 3 |
|  | 1.5 | 0 | 3 |
|  | 0.75 | 0 | 3 |
|  | 0.38 | 0 | 3 |
| 22 | 6.0 | 40 | 3 |
|  | 3.0 | 0 | 3 |
|  | 1.5 | 0 | 3 |
|  | 0.75 | 0 | 3 |
|  | 0.38 | 0 | 3 |
| 24 | 0.75* | 100 | 1 |
|  | 0.38* | 100 | 1 |
|  | 0.19* | 90 | 1 |
|  | 0.09* | 35 | 1 |
|  | 0.75* | 100 | 3 |
|  | 0.19* | 100 | 3 |
|  | 0.09* | 50 | 3 |
| 25 | 3.0 | 100 | 2 |
|  | 1.5 | 100 | 2 |
|  | 0.75 | 100 | 2 |
|  | 0.38 | 100 | 2 |
|  | 0.75 | 100 | 2 |
|  | 0.38 | 100 | 2 |
|  | 0.19 | 70 | 2 |
|  | 0.09 | 30 | 2 |
|  | 0.75 | 100 | 3 |
|  | 0.38 | 80 | 3 |
|  | 0.09 | 40 | 3 |
| 26 | 3.0 | 100 | 2 |
|  | 1.5 | 100 | 2 |
|  | 0.75 | 100 | 2 |
|  | 0.38 | 100 | 2 |
|  | 0.75 | 80 | 2 |
|  | 0.38 | 30 | 2 |
|  | 0.19 | 10 | 2 |
|  | 0.09 | 0 | 2 |
|  | 0.75 | 100 | 3 |
|  | 0.38 | 60 | 3 |
|  | 0.19 | 30 | 3 |
|  | 0.09 | 0 | 3 |
|  | 1.5 | 100 | 3 |
|  | 0.75 | 100 | 3 |
|  | 0.38 | 40 | 3 |
|  | 0.19 | 40 | 3 |

TABLE VII-continued

| Example No. | PPM of Compound in soil | Percent Control of Corn Rootworm | Days Post-Treatment |
|---|---|---|---|
| | 0.09 | 0 | 3 |
| 27 | 6.0 | 100 | 3 |
| | 3.0 | 100 | 3 |
| | 1.5 | 100 | 3 |
| | 0.75 | 100 | 3 |
| | 0.38 | 40 | 3 |
| | 0.19 | 0 | 3 |
| 28 | 3.0 | 100 | 2 |
| | 1.5 | 100 | 2 |
| | 0.75 | 100 | 2 |
| | 0.38 | 100 | 2 |
| | 1.5 | 100 | 3 |
| | 0.75 | 100 | 3 |
| | 0.38 | 60 | 3 |
| | 0.19 | 20 | 3 |
| | 0.09 | 10 | 2 |
| | 0.75 | 100 | 2 |
| | 0.38 | 100 | 2 |
| | 0.19 | 50 | 2 |
| | 0.09 | 0 | 2 |
| | 0.75 | 100 | 3 |
| | 0.38 | 100 | 3 |
| | 0.19 | 60 | 3 |
| | 0.09 | 10 | 3 |
| 29 | 6.0 | 100 | 3 |
| | 3.0 | 100 | 3 |
| | 1.5 | 100 | 3 |
| | 0.75 | 80 | 3 |
| | 0.38 | 40 | 3 |
| | 0.19 | 20 | 3 |
| 30 | 6.0 | 100 | 3 |
| | 3.0 | 100 | 3 |
| | 1.5 | 100 | 3 |
| | 0.75 | 100 | 3 |
| | 0.38 | 60 | 3 |
| | 0.19 | 0 | 3 |
| 31 | 6.0 | 100 | 4 |
| | 3.0 | 100 | 4 |
| | 1.5 | 100 | 4 |
| | 0.75 | 100 | 4 |
| | 0.38 | 100 | 4 |
| | 0.19 | 20 | 4 |
| | 0.09 | 0 | 4 |
| | 6.0 | 100 | 3 |
| | 3.0 | 100 | 3 |
| | 1.5 | 100 | 3 |
| | 0.75 | 100 | 3 |
| | 0.38 | 80 | 3 |
| | 0.19 | 40 | 3 |
| 32 | 6.0 | 100 | 3 |
| | 3.0 | 100 | 3 |
| | 1.5 | 100 | 3 |
| | 0.75 | 100 | 3 |
| | 0.38 | 40 | 3 |
| | 0.19 | 0 | 3 |
| 33 | 6.0 | 100 | 4 |
| | 3.0 | 100 | 4 |
| | 1.5 | 100 | 4 |
| | 0.75 | 100 | 4 |
| | 0.38 | 100 | 4 |
| | 0.19 | 60 | 4 |
| | 0.09 | 0 | 4 |
| 33 | 3.0 | 100 | 3 |
| | 1.5 | 100 | 3 |
| | 0.75 | 80 | 3 |
| | 0.38 | 40 | 3 |
| | 0.19 | 0 | 3 |
| | 0.09 | 0 | 3 |
| 34 | 0.75 | 50 | 3 |
| | 0.38 | 30 | 3 |
| | 0.19 | 10 | 3 |
| | 0.09 | 0 | 3 |
| 35 | 6.0 | 100 | 4 |
| | 3.0 | 100 | 4 |
| | 1.5 | 100 | 4 |
| | 0.75 | 100 | 4 |
| | 0.38 | 80 | 4 |
| | 0.19 | 40 | 4 |
| | 0.09 | 0 | 4 |
| 36 | 5.0 | 100 | 4 |
| | 5.0 | 100 | 4 |
| | 5.0 | 100 | 4 |
| | 5.0 | 100 | 4 |
| | 5.0 | 100 | 4 |
| | 5.0 | 100 | 4 |
| | 5.0 | 100 | 4 |
| | 5.0 | 100 | 4 |
| | 5.0 | 100 | 4 |
| | 0.75 | 100 | 3 |
| | 0.38 | 70 | 3 |
| | 0.19 | 10 | 3 |
| | 0.09 | 0 | 3 |
| 37 | 6.0 | 100 | 3 |
| | 3.0 | 100 | 3 |
| | 1.5 | 100 | 3 |
| | 0.75 | 100 | 3 |
| | 0.38 | 100 | 3 |
| | 0.19 | 50 | 3 |
| 40 | 12.0 | 90 | 3 |
| | 6.0 | 80 | 3 |
| | 3.0 | 40 | 3 |
| 41 | 12.0 | 100 | 3 |
| | 12.0 | 100 | 3 |
| | 6.0 | 90 | 3 |
| | 6.0 | 50 | 3 |
| | 6.0 | 30 | 3 |
| | 3.0 | 40 | 3 |
| | 3.0 | 0 | 3 |
| | 1.5 | 0 | 3 |
| | 1.5 | 0 | 3 |
| | 0.75 | 0 | 3 |
| | 0.75 | 0 | 3 |
| | 0.38 | 0 | 3 |
| | 0.19 | 0 | 3 |
| 48 | 12.0 | 100 | 4 |
| | 6.0 | 100 | 4 |
| | 3.0 | 100 | 4 |
| | 3.0 | 100 | 1 |
| | 3.0 | 100 | 2 |
| | 1.5 | 100 | 4 |
| | 1.5 | 100 | 1 |
| | 1.5 | 100 | 2 |
| | 0.75 | 100 | 4 |
| | 0.75 | 100 | 1 |
| | 0.75 | 100 | 2 |
| 48 | 0.38 | 40 | 1 |
| | 0.38 | 60 | 2 |
| | 0.19 | 0 | 1 |
| | 0.19 | 0 | 2 |
| | 0.09 | 0 | 1 |
| | 0.09 | 0 | 2 |
| 49 | 12.0 | 100 | 4 |
| | 6.0 | 100 | 4 |
| | 3.0 | 100 | 4 |
| | 3.0 | 100 | 1 |
| | 3.0 | 100 | 2 |
| | 1.5 | 100 | 4 |
| | 1.5 | 100 | 1 |
| | 1.5 | 100 | 2 |
| | 0.75 | 100 | 4 |
| | 0.75 | 100 | 1 |
| | 0.75 | 100 | 2 |
| | 0.38 | 100 | 1 |
| | 0.38 | 100 | 2 |
| | 0.19 | 30 | 1 |
| | 0.19 | 40 | 2 |
| | 0.09 | 0 | 1 |
| | 0.09 | 0 | 2 |
| 50 | 12.0 | 100 | 2 |
| | 6.0 | 100 | 2 |
| | 6.0 | 100 | 3 |
| | 3.0 | 100 | 2 |
| | 3.0 | 100 | 3 |
| | 1.5 | 100 | 2 |

TABLE VII-continued

| Example No. | PPM of Compound in soil | Percent Control of Corn Rootworm | Days Post-Treatment |
|---|---|---|---|
| | 1.5 | 100 | 3 |
| | 0.75 | 90 | 3 |
| | 0.38 | 50 | 3 |
| 51 | 12.0 | 100 | 2 |
| | 6.0 | 50 | 2 |
| | 3.0 | 0 | 2 |
| | 1.5 | 0 | 2 |
| | 0.75 | 0 | 2 |
| | 0.38 | 0 | 2 |
| | 0.19 | 0 | 2 |
| | 0.09 | 0 | 2 |
| | 0.04 | 0 | 2 |
| 52 | 12.0 | 100 | 5 |
| | 6.0 | 100 | 5 |
| | 3.0 | 100 | 5 |
| | 3.0 | 100 | 5 |
| | 1.5 | 100 | 5 |
| | 1.5 | 100 | 5 |
| | 0.75 | 90 | 5 |
| | 0.38 | 70 | 5 |
| | 0.19 | 40 | 5 |
| | 0.09 | 10 | 5 |
| | 0.04 | 0 | 5 |
| 56 | 12.0 | 100 | 4 |
| | 6.0 | 100 | 4 |
| | 3.0 | 90 | 4 |
| | 1.5 | 50 | 4 |
| | 0.75 | 0 | 4 |
| | 0.38 | 0 | 4 |
| | 0.19 | 0 | 4 |
| | 0.09 | 0 | 4 |
| | 0.04 | 0 | 4 |

*four replicates

Southern Corn Rootworm-Residual Test

Selected compounds were evaluated for residual control of southern corn rootworm. The test was conducted as follows. Each compound was dissolved in acetone, sprayed onto soil, and mixed well. The soil was added, in a 1" deep layer, to pots already containing 3" of untreated soil with 3 corn seeds on top. The pots were held under normal greenhouse conditions for 21 days, at which time average crown root length measurements were made, on a minimum of 9 plants per treatment. Additionally, all soil was removed from each pot, mixed well, and bioassayed with 3rd instar southern corn rootworm larvae (*Diabrotica undecimpunctata howardi* Barber, Order Coleoptera, Family Chrysomelidae). There were three replicates per treatment.

Phytotoxicity was evaluated in either of two methods. In a first method, used for most of the tests, the average crown root length was determined; crown root length in the controls varied from about 110 to about 150 mm and averaged about 120 mm. In the second method, crown root area was measured by a LI-COR Model LI-3000 portable area meter, with the controls regarded as 100 percent and other treatments reported as a percent of control.

Results were as set forth in the following table.

TABLE VIII

| Treatment, Example # | Corn Rootworm-Residual | | | | | |
|---|---|---|---|---|---|---|
| | Avg. Crown Root Length (mm) | | | Percent Mortality Corn Rootworm | | |
| | 8 | 4 | 2 | 8 | 4 | 2 PPM |
| 1 | 20 | 25 | 67 | 100 | 100 | 27 |
| 6 | 0 | 0 | 25 | 100 | 100 | 100 |
| 8 | 8 | 38 | 75 | 87 | 87 | 27 |
| 24 | 53 | 82 | 102 | 100 | 26 | 34 |
| 24 | 21 | 33 | 58 | 100 | 100 | 33 |
| 24 | 20 | 54 | 81 | 100 | 100 | 40 |
| 25 | 16 | 52 | 62 | 40 | 0 | 0 |
| 26 | 44 | 54 | 93 | 100 | 87 | 33 |
| 28 | 49 | 77 | 90 | 53 | 13 | 0 |
| 29 | 34 | 53 | 103 | 87 | 53 | 7 |
| 30 | 30 | 42 | 71 | 60 | 80 | 0 |
| 31 | 24 | 43 | 83 | 100 | 20 | 0 |
| 32 | 33 | 51 | 58 | 80 | 60 | 0 |
| 35 | 15 | 36 | 80 | 100 | 100 | 73 |
| 36 | 37 | 85 | 97 | 100 | 100 | 87 |
| 48 | 5* | 17* | 26* | 100 | 100 | 87 |
| 49 | 21* | 17* | 35* | 100 | 100 | 7 |
| 50 | 9* | 24* | 47* | 100 | 73 | 27 |

*Percent of crown roots

Corn Rootworm-Field Test

The compound of Example 24 was evaluated for the control of corn rootworm in the field, at a site known to be naturally infested with Diabrotica spp. The compound was formulated as a 10% granule, as described below in Example A. Field corn was planted and the granular formulation was applied two days later in a seven-inch band along the row. Ratings were made of various parameters:

Crop Emergence, 12 days=scale of 0-10, with 0=no effect on emergence and 10=no emergence
Crop Stand Count, 34 days=% of control
Crop Vigor Rating, 20 days=% of control
Root Injury Rating, 20 days=scale of 0-100, with 0=no injury and 100=maximum injury
Root Injury Rating, 42 days=scale of 0-100, with 0=no injury and 100=maximum injury
Rootworm Damage Rating, 42 days=1-6, with 1=no damage and 6=maximum damage Results are recorded in the following table.

TABLE IX

| Treatment* | Corn Rootworm - Field Test | | | | | |
|---|---|---|---|---|---|---|
| | Crop Emergence Rating (12 days) | Crop Stand Count (34 days) | Crop Vigor Rating (20 days) | Root Injury Rating (20 days) | Root Injury Rating (42 days) | Rootworm Damage Rating (42 days) |
| Compound of Example 24 | | | | | | |
| 0.5 lb/acre | 0 | 97.3 | 100 | 0 | 3 | 2.1 |
| 1.0 lb/acre | 0 | 86.3 | 100 | 0 | 12 | 1.8 |
| Fonofos | | | | | | |
| 0.5 lb/acre | 0 | 93.1 | 100 | 0 | 1 | 2.4 |
| 1.0 lb/acre | 0 | 91.8 | 100 | 0 | 0 | 3.0 |
| 2.0 lbs/acre | 0 | 91.8 | 100 | 0 | 0 | 2.1 |
| chlorpyrifos | | | | | | |
| 0.5 lb/acre | 0 | 101.4 | 100 | 0 | 0 | 2.3 |
| 1.0 lb/acre | 0 | 101.4 | 100 | 0 | 0 | 2.1 |
| 2.0 lbs/acre | 0 | 97.3 | 100 | 0 | 0 | 2.2 |

TABLE IX-continued

Corn Rootworm - Field Test

| Treatment* | Crop Emergence Rating (12 days) | Crop Stand Count (34 days) | Crop Vigor Rating (20 days) | Root Injury Rating (20 days) | Root Injury Rating (42 days) | Rootworm Damage Rating (42 days) |
|---|---|---|---|---|---|---|
| terbufos | | | | | | |
| 0.5 lb/acre | 0 | 91.8 | 100 | 0 | 0 | 2.0 |
| 1.0 lb/acre | 0 | 102.7 | 100 | 0 | 0 | 2.2 |
| 2.0 lbs/acre | 0 | 98.6 | 100 | 0 | 0 | 2.0 |
| phorate | | | | | | |
| 0.5 lb/acre | 0 | 104.1 | 100 | 0 | 0 | 2.3 |
| 1.0 lb/acre | 0 | 95.9 | 100 | 0 | 1 | 2.9 |
| 2.0 lbs/acre | 0 | 101.4 | 100 | 0 | 1.5 | 2.3 |
| carbofuran | | | | | | |
| 0.5 lb/acre | 0 | 102.7 | 100 | 0 | 0 | 2.0 |
| 1.0 lb/acre | 0 | 110.9 | 100 | 0 | 0 | 2.0 |
| 2.0 lbs/acre | 0 | 90.4 | 100 | 0 | 2.0 | 1.9 |
| trimethacarb | | | | | | |
| 0.5 lb/acre | 0 | 97.3 | 100 | 0 | 0 | 1.9 |
| 1.0 lb/acre | 0 | 94.5 | 100 | 0 | 0 | 2.1 |
| 2.0 lbs/acre | 0 | 95.9 | 100 | 0 | 0 | 2.0 |
| isofenphos | | | | | | |
| 0.5 lb/acre | 0 | 93.1 | 100 | 0 | 0 | 2.0 |
| 1.0 lb/acre | 0 | 97.3 | 100 | 0 | 0 | 1.8 |
| 2.0 lbs/acre | | 97.3 | 100 | 0 | 0 | 2.0 |
| control | 0 | 100 | 100 | 0 | 0 | 2.7 |

*0.5 lb/acre = 0.56 kg/ha
1.0 lb/acre = 1.12 kg/ha
2.0 lbs/acre = 2.24 kg/ha

Black Cutworm

The compounds of Examples 1 and 36 were evaluated for the control of black cutworm (*Agrotis ipsilon* (Hufnagel) Order Lepidoptera, Family Noctuidae). Each compound was dissolved in acetone and the solution was pipetted onto sandy loam soil to obtain the desired soil concentration. The treated soil was transferred onto a petri dish and allowed to air dry for 24 hours. Laboratory reared 3rd-4th-instar black cutworm larvae were then introduced into the treated soil; corn seedlings were supplied as a food source. There were two replicates per treatment. Mortality readings were made three days post treatment. Results were as set forth in the following table.

TABLE X

| Black Cutworm #1 | |
|---|---|
| Treatment | Percent Control |
| Compound of Example 1 | |
| 24.0 | 70 |
| 12.0 | 20 |
| 6.0 | 0 |
| 3.0 | 0 |
| 1.5 | 0 |
| Compound of Example 36 | |
| 24.0 | 40 |
| 12.0 | 0 |
| 6.0 | 0 |
| 3.0 | 0 |
| 1.5 | 0 |
| terbufos | |
| 24.0 | 100 |
| 12.0 | 100 |
| 6.0 | 50 |
| 3.0 | 0 |
| 1.5 | 0 |
| 0.75 | 0 |
| 0.38 | 0 |
| chlorpyrifos | |
| 24.0 | 100 |
| 12.0 | 100 |
| 6.0 | 100 |
| 3.0 | 100 |
| 1.5 | 10 |
| 0.75 | 0 |
| 0.38 | 0 |
| Control | 0 |

*Scale of
0 = none
1 = 1-50%
2 = 51-99%
3 = 100%

The same compounds were evaluated again for the control of black cutworm, employing the same procedures except that there were four replicates and that mortality readings were made four days post treatment. Results were as set forth in the following table.

TABLE XI

| Black Cutworm #2 | |
|---|---|
| Treatment | Percent Control |
| Compound of Example 1 | |
| 48 ppm | 100 |
| 24 ppm | 15 |
| 12 ppm | 10 |
| Compound of Example 36 | |
| 48 ppm | 65 |
| 24 ppm | 0 |
| 12 ppm | 0 |
| chlorpyrifos | |
| 12 ppm | 100 |
| 6 ppm | 100 |
| 3 ppm | 100 |
| 1.5 ppm | 100 |
| terbufos | |
| 12 ppm | 100 |
| 6 ppm | 100 |
| 3 ppm | 100 |
| 1.5 ppm | 100 |

TABLE XI-continued

| Black Cutworm #2 | |
|---|---|
| Treatment | Percent Control |
| control | 0 |

Diamondback Moth

Selected compounds of the present invention were evaluated for the control of the larval stage of the diamondback moth (*Plutella xylostella* (Linne) Order Lepidoptira, Family Plutellidae). For each test, a petri dish base and its lid were lined with filter paper, and both were placed in a cabinet and sprayed with a solution of the compound to supply 50 ml of solution per 0.5 square meter of surface area. The papers were allowed to dry for 3 hours at 25° C. Five 3-rd-4th-instar larvae were placed in each petri dish base and the lid placed on it. After one hour, and daily thereafter, an untreated Chinese cabbage leaf disc was supplied as food. After two days, the number of live larvae was determined and percent control was calculated. Tests were conducted with both a wild strain ("susceptible") and a strain resistant to carbamate, pyrethroid, organochlorides and organophosphate insecticides ("resistant"). Results were as set forth in the following table.

TABLE XII

| | Diamondback Moth | | | |
|---|---|---|---|---|
| | Percent Control | | | |
| Treatment | 12.5 ppm | 25 ppm | 50 ppm | 100 ppm |
| Compound of Example 1 | | | | |
| Resistant | 100 | 100 | 100 | 100 |
| Susceptible | 100 | 100 | 100 | 100 |
| Compound of Example 36 | | | | |
| Resistant | 67 | 78 | 89 | 100 |
| Susceptible | 31 | 100 | 93 | 100 |
| Cypermethrin | | | | |
| Resistant | — | 11 | 22 | 33 |
| Susceptible | — | 31 | 100 | 100 |

German Cockroach

The compounds of Examples 24–28 were evaluated for the control of German cockroach (*Blattella germanica* (Linne) Order Orthoptera, Family Blattellidae). The evaluation was carried out by dissolving the compound in the same solvent/emulsifier mixture employed in the mite-insect test above, and pouring 2 ml of the solution onto a filter paper in a petri dish. Ten German cockroaches were immediately placed in the petri dish and held there for 24 hours at which time the percent mortality was determined. Results were as set forth in the following table.

TABLE XIII

| | German Cockroach | | | |
|---|---|---|---|---|
| Example No. | 500 | 100 | 10 | PPM |
| 24 | 100 | 40 | 0 | |
| 25 | 100 | | | |
| 26 | 60 | | | |
| 27 | 80 | | | |
| 28 | 40 | | | |

Summary of Additional Trials

The compounds of Examples 1 and 36 were evaluated for the control of corn rootworm at numerous locations throughout the midwestern U.S. Observations were also made for various parameters of phytotoxicity. Each compound was formulated as a 10% granule; application rates were 0.85–3.4 grams/100 row feet. At most locations, each of the compounds controlled corn rootworm with no phytotoxicity. At some locations, phytotoxicity was observed, especially at higher rates. The phytotoxicity took the form of some delay in emergence, injury on emergence, early and midseason root injury, and midseason crop injury. The phytotoxicity was observed despite the fact that many of the trials employed post presswheel placement, therefore suggesting the need for even better separation of the present compounds from the corn seed or a safer formulation.

In European field trials at 1–4 kg/ha on wheat, potatoes, and sugar beets, each of the compounds controlled wireworm.

However, the compound of Example 1 exhibited crop injury to wheat and potatoes, and both compounds exhibited unacceptable crop injury to sugar beets.

Application of Example 36 to bluegrass showed no injury. Although no insecticidal efficacy data were obtained in the trial, the finding suggests that the present compounds can be used for the control of turf insects. Cf. Tables X and XI.

The foregoing illustrates that the compounds of the present invention are effective against a number of insects and arachnids, including organisms that attack foliage as well as organisms that live in the soil and attack roots and other underground parts of plants. Therefore, in another embodiment, the present invention is directed to a method of inactivating an insect or arachnid which comprises applying to a locus of the insect or arachnid an effective amount of one or more of the compounds of the present invention.

Insects and arachnids against which the present method can be practiced include the various species identified above as well as many others, including, among the insects, the following Coleoptera
  *Anthonomus grandis*—boll weevil
  *Conotrachelus nenuphar*—plum curculio
  *Curculio caryae*—pecan weevil
  *Diabrotica* spp.—rootworm and cucumber beetles
  *Echinocnemus squameus*—rice plant weevil
  *Epitrix hirtipennis*—tobacco flea beetle
  *Eutheola humilis rugiceps*—sugarcane beetle
  *Hypera postica*13 alfalfa weevil
  *Leptinotarsa decimlineata*—Colorado potato beetle
  *Lissorhoptrus oryzophilus*—rice water weevil
  *Oulema oryzae*—rice leaf beetle
  *Phyllotreta striolata*—striped flea beetle
  *Melanotus* spp. and *Agriotes* spp.—wireworms
  *Stenolophus lecontei*—seedcorn beetle
  *Popillia japonica*—Japanese beetle
  *Sphenophorus maidis*—maize billbug
  *Systena blanda*—palestriped flea beetle
Diptera
  *Contarinia sorghicola*—sorghum midge
  *Dacus dorsalis*—oriental fruit fly
  *Liriomyza* spp.—leaf miner
  *Rhagoletis pomonella*—apple maggot
  *Hylemia* spp. and *Delia* spp.—root and seed maggots Heteroptera
  *Anasa tristis*—squash bug
  *Blissus leucopterus leucopterus*—chinch bug
  *Euschistus servus*—brown stink bug
  *Lygus lineolaris*—tarnished plant bug
  *Nezara viridula*—southern green stink bug
  *Oebalus pugnax*—rice stink bug
  *Pseudatomoscelis seriatus*—cotton fleahopper
Homoptera
  *Clastoptera achatina*—pecan spittlebug
  *Empoasca fabae*—potato leafhopper
  *Eriosoma lanigerum*—wooly apple aphid
  *Fiorinia theae*—tea scale
  *Graminella nigrifrons*—blackfaced leafhopper
  *Icerya purchasi*—cottony cushion scale
  *Laodelphax striatellus*—small brown planthopper
  *Lepidosaphes ulmi*—oystershell scale
  *Myzus persicae*—green peach aphid
  *Nephotettix cincticeps*—green rice leafhopper
  *Niloparvata lugens*—brown rice planthopper
  *Phylloxera devastatrix*—pecan phylloxera
  *Planococcus citri*—citrus mealybug
  *Psylla pyricola*—pear psylla
  *Quadraspidiotus perniciosus*—San Jose scale
  *Rhopalosiphum maidis*—corn leaf aphid
  *Sipha flava*—yellow sugarcane aphid
  *Sogatella furcifera*—whitebacked planthopper
  *Spissistilus festinus*—threecornered alfalfa hopper
  *Trialeurodes vaporariorum*—greenhouse whitefly
  *Anuraphis maidiradicis*—corn root aphid
Hymenoptera
  Atta spp.—leafcutter ants
  Camponotus spp.—carpenter ants
  Dolichovespula spp.—yellowjackets
  *Solenopsis invicta*—red imported fire ant
  *Tetramorium caespitum*—pavement ant
  Vespidae spp.—hornets, wasps
Isoptera
  *Coptotermes formosanus*—Formosan subterranean termite
  *Reticulitermes flavipes*—eastern subterranean termite
Lepidoptera
  Agrotis spp. and other genera—cutworms
  *Alabama argillacea*—cotton leafworm
  *Anticarsia gemmatalis*—velvetbean caterpillar
  *Buccalatrix thurberiella*—cotton leafperforator
  *Chilo suppressalis*—rice stem borer
  *Choristoneura fumiferana*—spruce budworm
  *Cydia pomonella*—codling moth
  *Elasmopalpus lignosellus*—lesser cornstalk borer
  *Grapholita molesta*—oriental fruitmoth
  *Heliothis virescens*—tobacco budworm
  *Heliothis zea*—cotton bollworm
  *Keiferia lycopersicella*—tomato pinworm
  *Ostrinia nubilalis*—European corn borer
  *Parnara guttata*—rice skipper
  *Pectinophora gossypiella*—pink bollworm
  *Pieris rapae*—imported cabbageworm
  *Plutella xylostella*—diamondback moth
  *Pseudoplusia includens*—soybean looper
  *Sesamia inferens*—rice swarming caterpillar
  *Spodoptera littoralis*—Egyptian cotton leafworm
  Spodoptera spp.—armyworms
  Synanthedon spp.—clearwing moths
  *Trichoplusia ni*—cabbage looper
  *Tryporyza incertula*—yellow rice borer
  Crambus spp.—webworms
Orthoptera
  Blatella spp.—cockroaches
  Gryllus spp.—field crickets
  Melanoplus spp.—grasshoppers
  Periplaneta spp.—cockroaches
  *Scapteriscus acletus*—southern mole cricket
Thysanoptera
  *Frankliniella tritici*—flower thrips
  *Sericothrips variabilis*—soybean thrips
  *Thrips simplex*—gladiolus thrips
  *Thrips tabaci*—onion thrips
and among the arachnids, the following:

| Family | Scientific Name | Common Name |
|---|---|---|
| ACARIDAE | *Aleurobius farinae* | Flour mite |
| | *Rhizoglyphus echinopus* | Bulb mite |
| | *Rhizoglyphus elongatus* | Elongate mite |
| | *Rhizoglyphus rhizophagus* | Root mite |
| | *Rhizoglyphus sagittatae* | Balsam root mite |
| | *Rhizoglyphus tarsalis* | Beet mite |
| ERIOPHYIDAE | *Abacarus hystrix* | |
| | *Aceria brachytarsus* | |
| | *Aceria essigi* | Redberry mite |
| | *Aceria ficus* | |
| | *Aceria fraxinivorus* | |
| | *Aceria granati* | |
| | *Aceria parapopuli* | Cottonwood mite |
| | *Aceria sheldoni* | Citrus bud mite |
| | *Aceria tulipae* | Wheat curl mite |
| | *Aceria schlechtendali* | Apple rust mite |
| | *Eriophyes convolvens* | |
| | *Eriophyes insidiosus* | |
| | *Eriophyes malifoliae* | Apple leaf mite |
| | *Eriophyes padi* | Plum twig gall mite |
| | *Eriophyes pruni* | Plum leaf gall mite |
| | *Eriophyes pyri* | Pear leaf blister mite |
| | *Eriophyes ramosus* | Juniper mite |
| | *Eriophyes ribis* | Currant gall mite |
| | *Eriophyes vitis* | Grape erineum mite |
| | *Phyllocoptes gracilis* | Blackberry mite |
| | *Phyllocoptruta oleivora* | Citrus rust mite |
| | *Phytoptus ribis* | |

| Family | Scientific Name | Common Name |
| --- | --- | --- |
| | *Trisetacus pini* | Pine needle mite |
| | *Vasates amygdalina* | David peach mite |
| | *Vasates cornutus* | Peach silver mite |
| | *Vasates eurynotus* | Celery rust mite |
| | *Vasates schlechtendali* | Rusty leaf mite |
| EUPODIDAE | *Linopodes* spp. | |
| PENTHALEIDAE | *Halotydeus destrustor* | Redlegged earth mite |
| | | Black sand mite |
| | *Penthaleus major* | Winter grain mite |
| | | Blue oat mite |
| PYEMOTIDAE | *Siteroptes cerealium* | |
| TARSONEMIDAE | *Polyphagotarsonemus latus* | Broad mite |
| | *Steneotarsonemus pallidus* | Cyclamen mite |
| TENUIPALPIDAE | *Brevipalpus californicus* | California citrus mite |
| | *Brevipalpus obovatus* | |
| | *Brevipalpus lewisi* | Flat mite |
| | *Tenuipalpes granati* | |
| | *Tenuipalpes pacificus* | |
| TETRANYCHIDAE | *Bryobia arborea* | Brown mite |
| | *Bryobia rubrioculus* | |
| | *Eotetranychus coryli* | |
| | *Eotetranychus lewisi* | Lewis spider mite |
| | *Eotetranychus sexmaculatus* | Sixspotted spider mite |
| | *Eotetranychus weldoni* | Weldon's mite |
| | *Eotetranychus willametti* | |
| | *Eutetranychus banksi* | Texas citrus mite |
| | *Mediolata mali* | Apple mite |
| | *Oligonychus ilicis* | Southern red mite |
| | *Oligonychus pratensis* | Banks grass mite |
| | *Oligonychus ununguis* | Spruce tree spider mite |
| | *Panonychus citri* | Citrus red mite |
| | *Panonychus ulmi* | European red mite |
| | *Paratetranychus modestus* | Corn mite |
| | *Paratetranychus pratensis* | Date mite |
| | *Paratetranychus viridis* | Green mite |
| | *Petrobia decepta* | Barley mite |
| | *Schizotetranychus celarius* | Bamboo mite |
| | *Schizotetranychus pratensis* | Alfalfa mite |
| | *Tetranychus canadensis* | Fourspotted mite |
| | *Tetranychus cinnabarinus* | |
| | *Tetranychus mcdanieli* | McDaniel mite |
| | *Tetranychus pacificus* | Pacific mite |
| | *Tetranychus schoenei* | Schoene mite |
| | *Tetranychus telarius* | Common red spider |
| | *Tetranychus urticae* | Twospotted spider mite |
| | *Tetranychus turkestani* | Strawberry mite |
| | *Tetranychus desertorum* | Desert mite |

The present compounds are employed for the control of insects and arachnids in accordance with standard practices of the agricultural chemical industry. Thus, the compounds, while they can be employed alone, are preferably formulated with conventional adjuvants, as described in more detail in the section below concerning Formulations. The amount of the present compounds which will provide insecticidal and/or arachnicidal activity is not critical and will vary widely, depending on the locus (foliage, soil, etc.), the susceptibility of the particular insect or arachnid, the particular compound chosen, weather and soil conditions, and the like. In general, when employing the compounds in spray formulations to be applied to foliage, concentrations of from 1 to 5000 ppm are efficacious; however, lesser concentrations such as from 1 to 100 ppm are often equally efficacious. In the case of application to soil to control soil-dwelling organisms, concentrations in the soil of from 1 ppm or less to as much as 50 ppm provide good activity. With the more active members of the series, lesser concentrations of from 1 to 10 ppm provide good activity.

Application of the compounds of the present invention is by conventional practices. Where the compounds are employed for the control of corn rootworm and other soil dwelling organisms that attack roots of plants, it is often preferred to apply a compound in a band along and including the crop row. This maximizes the protection of the crop, while minimizing the total amount of compound applied. Also, since the compounds of the present invention exhibit some phytotoxicity, it is preferred that the compounds be employed in a technique by which a pesticide is prevented from contacting seeds, for example, post presswheel placement.

PREFERRED EMBODIMENTS

Although the compounds of the present invention are generally effective for the control of numerous insect and arachnid species, they have been found to be exceptionally effective for the control of the larval stage of corn rootworm (Diabrotica spp.) Therefore, a preferred embodiment of the present invention is a method of inactivating a corn rootworm larva which comprises applying to a locus of the larva an effective amount of a present compound.

In addition to this preferred embodiment in the identity of the insects or arachnids controlled by the present invention, there are preferred embodiments among the compounds of the present invention.

The preferences among compounds of all of formulae I, II, and III are (1) a preference for $R^3$=hydrogen,
(2) a preference for $R^4$=substituted aryl as defined, more particularly, for $R^4$=substituted phenyl as defined, and especially for the following substituted phenyl groups:

(a) 2,4-disubstituted phenyl of the formula

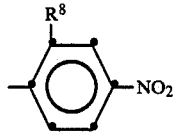

wherein $R^8$=chloro, bromo, iodo, cyano, methyl, trifluoromethyl, or nitro; and (b) 2,4,5(or 2,4,6)-trisubstituted phenyl of the formula

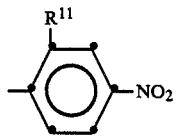

wherein $R^{11}$=bromo, chloro, or methyl. The preferences among compounds of formula I are (1) $R^0$=fluoro and
(2) each of $R^1$ and $R^2$=$CF_3$, $C_2F_5$, or $C_3F_7$.

Among the salts of the present invention, it has been found that the ammonium salts are preferred, and among the ammonium salts, the following particular salts are especially advantageous: hexadecyltrimethylammonium, octadecyltrimethylammonium, tributylammonium, tris(2-hydroxyethyl)ammonium, tris(2 or 3-hydroxypropyl)ammonium, and dimethylbis($C_{10}$–$C_{18}$)ammonium.

HERBICIDAL ACTIVITY

In addition to exhibiting activity against insects and arachnids, the present compounds also exhibit some herbicidal activity. In general, the herbicidal activity is expressed at rates higher than those at which insecticidal and arachnicidal activity is exhibited. Therefore, the preferred insecticidal/arachnicidal utility of the present invention can generally be practiced with minimal or no phytotoxicity.

Representative compounds of the present invention were evaluated for herbicidal efficacy in standard screening tests. In these tests, each compound was evaluated against a number of crop and weed species, for both preemergent and postemergent effect. Each compound was formulated by dissolving it in the acetone/emulsifier composition described in the mite-insect screen above. It was then sprayed onto flats within one day after they had been seeded to various plant species (the preemergent test) or onto young plants about 9 days after planting (the postemergent test). Throughout the test, the pots were maintained under good greenhouse growing conditions. Ratings were made 18 days after compound application in the preemergence test, and 14 days after compound application in the postemergent test, employing a scale of 1–5, with 1=no injury and 5=death. Results were as set forth in the following tables of preemergent data (Table XIV) and postemergent data (Table XV).

The following code was used in Tables XIV and XV:

A = Corn
B = Cotton
C = Soybean
D = Wheat
E = Alfalfa
F = Sugar Beet
G = Rice
H = Cucumber
I = Tomato
J = Barley
K = Barnyard Grass
L = Lambsquarter
M = Cocklebur
N = Large Crabgrass
O = Mustard
P = Pigweed
Q = Ryegrass
R = Small Crabgrass
S = Foxtail Millet
T = Bindweed
U = Wild Oat
V = Nutgrass
W = Velvetleaf
X = Jimsonweed
Y = Smartweed
Z = Morningglory
a = Zinnia Note:
8 lb/A = 8.96 kilograms per hectare (kg/ha)
4 lb/A = 4.48 kg/ha
2 lb/A = 2.24 kg/ha
1 lb/A = 1.12 kg/ha
0.5 lb/A = 0.56 kg/ha
0.25 lb/A = 0.28 kg/ha
0.125 lb/A = 0.14 kg/ha
0.625 lb/A = 0.07 kg/ha.

TABLE XIV

| EX. NO. | Rate lbs/A | A | B | C | D | E | F | G | H | I | J | K | L | M | N | O | P | Q | R | S | T | U | V | W | X | Y | Z | a |
|---|---|---|---|---|---|---|---|---|---|---|---|---|---|---|---|---|---|---|---|---|---|---|---|---|---|---|---|---|
| 1 | 8 | | | | | | | | | 5 | | 5 | | | 5 | 5 | 5 | | 5 | | 5 | | 5 | | | 5 | 5 | |
|   | 4 | 1 | 1 | 1 | 3 | 5 | 5 | 2 | 3 | 3 | | 3 | 4 | | 4 | 3 | 4 | | 4 | | 3 | | 5 | 3 | | 3 | 4 | |
|   | 2 | 1 | 1 | 1 | 1 | 5 | 5 | 1 | 1 | 2 | | 3 | 4 | | 3 | 1 | 4 | | 3 | | 2 | | 2 | 2 | | 1 | 2 | |
|   | 1 | 1 | 1 | 1 | 1 | 3 | 2 | 1 | 1 | 1 | | 1 | 3 | | 2 | 1 | 3 | | 1 | | 1 | | 1 | 1 | | 1 | 1 | |
| 4 | 8 | | | | | | | | | 5 | | 5 | | | 5 | 5 | 5 | | 5 | | 5 | | 5 | | | 5 | 5 | |
|   | 4 | 5 | 4 | 5 | 5 | | 5 | 5 | | 5 | | 5 | | | 5 | 5 | 5 | | 5 | | 5 | | 5 | 5 | | 5 | 5 | |
|   | 2 | 5 | 4 | 5 | 5 | | 5 | 4 | | 5 | | 5 | | | 5 | 4 | 5 | | 5 | | 5 | | 5 | 4 | | 5 | 4 | |

TABLE XIV-continued

PLANT SPECIES
Pre-emergence

| EX. NO. | Rate lbs/A | A | B | C | D | E | F | G | H | I | J | K | L | M | N | O | P | Q | R | S | T | U | V | W | X | Y | Z | a |
|---|---|---|---|---|---|---|---|---|---|---|---|---|---|---|---|---|---|---|---|---|---|---|---|---|---|---|---|---|
| | 1 | 4 | 3 | 4 | 4 | | 5 | 4 | | | | 5 | | | 5 | 3 | 5 | | | 4 | | 3 | | 4 | 3 | | 5 | 3 |
| | .5 | 2 | 3 | 4 | 1 | | 3 | 1 | | 2 | 1 | | 2 | | 2 | 2 | 4 | | | 3 | | 1 | | 2 | 2 | | 4 | |
| | .25 | 2 | 2 | 3 | 1 | | 4 | 1 | | 1 | 1 | | 2 | | 1 | 2 | 3 | | | 3 | | 1 | | 2 | 2 | | 3 | |
| | .125 | 1 | 1 | 3 | 1 | | 2 | 1 | | 1 | 1 | | 1 | | 1 | 1 | 2 | | | 1 | | 1 | | 1 | 1 | | 2 | |
| | .0625 | 1 | 1 | 1 | 1 | | 2 | 1 | | 1 | 1 | | 1 | | 1 | 1 | 1 | | | 1 | | 1 | | 1 | 1 | | 1 | |
| 5 | 8 | | | | | | | | | 5 | | 4 | | | 5 | 5 | 5 | | | 5 | | 5 | | 5 | | | 3 | 3 |
| | 4 | 1 | 1 | 2 | 3 | | 5 | 3 | | | | 2 | | | 5 | 3 | 5 | | | 4 | | 3 | | 2 | 4 | | 2 | 3 |
| | 2 | 1 | 1 | 1 | 1 | | 3 | 1 | | | | 1 | | | 1 | 1 | 3 | | | 1 | | 1 | | 1 | 1 | | 1 | 1 |
| | 1 | 1 | 1 | 1 | 1 | | 1 | 1 | | | | 1 | | | 1 | 1 | 3 | | | 1 | | 1 | | 1 | 1 | | 1 | 1 |
| 6 | 8 | | | | | | | | | 4 | | 5 | | | 5 | 4 | 5 | | | 5 | | 5 | | 5 | | | 5 | 4 |
| | 4 | 5 | 5 | 5 | 5 | | 5 | 5 | | | | 5 | | | 5 | 5 | 5 | | | 5 | | 5 | | 5 | 5 | | 5 | 5 |
| | 2 | 5 | 5 | 5 | 5 | | 5 | 5 | | | | 5 | | | 5 | 5 | 5 | | | 5 | | 5 | | 5 | 5 | | 5 | 5 |
| | 1 | 5 | 3 | 5 | 5 | | 5 | 5 | | | | 5 | | | 5 | 4 | 5 | | | 5 | | 5 | | 5 | 4 | | 5 | 5 |
| | .5 | 3 | 1 | 4 | 1 | | 3 | 1 | | 2 | 1 | | 3 | | 3 | 2 | 3 | | | 4 | | 1 | | 3 | 1 | | 4 | |
| | .25 | 2 | 1 | 4 | 1 | | 3 | 1 | | 2 | 1 | | 3 | | 3 | 1 | 3 | | | 3 | | 1 | | 2 | 1 | | 4 | |
| | .125 | 1 | 1 | 3 | 1 | | 1 | 1 | | 1 | 1 | | 1 | | 1 | 1 | 2 | | | 3 | | 1 | | 1 | 1 | | 4 | |
| | .0625 | 1 | 1 | 2 | 1 | | 1 | 1 | | 1 | 1 | | 1 | | 1 | 1 | 1 | | | 1 | | 1 | | 1 | 1 | | 2 | |
| 7 | 8 | | | | | | | | | 3 | | 5 | | | 3 | 3 | 4 | | | 5 | | 3 | | 5 | | | 5 | 3 |
| | 4 | 3 | 2 | 4 | 2 | | 4 | 4 | | | | 3 | | | 4 | 3 | 4 | | | 3 | | 4 | | 5 | 2 | | 4 | 4 |
| | 2 | 2 | 1 | 4 | 1 | | 3 | 3 | | | | 1 | | | 3 | 1 | 4 | | | 2 | | 1 | | 1 | 1 | | 3 | 2 |
| | 1 | 1 | 1 | 1 | 1 | | 1 | 1 | | | | 1 | | | 2 | 1 | 3 | | | 2 | | 1 | | 1 | 1 | | 1 | 1 |
| 8 | 8 | | | | | | | | | 5 | | 5 | | | 5 | 5 | 5 | | | 5 | | 5 | | 5 | | | 5 | 5 |
| | 4 | 4 | 3 | 5 | 5 | | 5 | 5 | | | | 4 | | | 5 | 5 | 5 | | | 5 | | 4 | | 5 | 4 | | 4 | 5 |
| | 2 | 3 | 3 | 5 | 4 | | 5 | 5 | | | | 4 | | | 5 | 5 | 5 | | | 5 | | 4 | | 5 | 4 | | 4 | 5 |
| | 1 | 2 | 2 | 4 | 2 | | 5 | 4 | | | | 3 | | | 5 | 5 | 5 | | | 4 | | 5 | | 3 | 2 | | 3 | 2 |
| | .5 | 1 | 3 | 2 | 2 | | 3 | 2 | | 2 | 1 | | 1 | | 3 | 2 | 2 | | | 1 | | 1 | | 2 | 1 | | 4 | |
| | .25 | 1 | 1 | 1 | 1 | | 2 | 1 | | 1 | 1 | | 1 | | 1 | 1 | 1 | | | 1 | | 1 | | 1 | 1 | | 1 | |
| | .125 | 1 | 1 | 1 | 1 | | 1 | 1 | | 1 | 1 | | 1 | | 1 | 1 | 1 | | | 1 | | 1 | | 1 | 1 | | 1 | |
| | .0625 | 1 | 1 | 1 | 1 | | 1 | 1 | | 1 | 1 | | 1 | | 1 | 1 | 1 | | | 1 | | 1 | | 1 | 1 | | 1 | |
| 9 | 8 | | | | | | | | | 1 | | 1 | | | 3 | 1 | 1 | | | 1 | | 1 | | 1 | | | 1 | 1 |
| 10 | 8 | | | | | | | | | 1 | | 1 | | | 5 | 1 | 5 | | | 4 | | 1 | | 1 | | | 1 | 1 |
| | 4 | 1 | 1 | 1 | 1 | | 1 | 1 | | | | 1 | | | 1 | 1 | 4 | | | 3 | | 1 | | 1 | 1 | | 1 | 1 |
| | 2 | 1 | 1 | 1 | 1 | | 1 | 1 | | | | 1 | | | 1 | 1 | 3 | | | 1 | | 1 | | 1 | 1 | | 1 | 1 |
| | 1 | 1 | 1 | 1 | 1 | | 1 | 1 | | | | 1 | | | 1 | 1 | 3 | | | 1 | | 1 | | 1 | 1 | | 1 | 1 |
| 11 | 8 | | | | | | | | | 1 | | 1 | | | 1 | 1 | 1 | | | 1 | | 1 | | 1 | | | 1 | |
| 13 | 8 | | | | | | | | | 5 | | 5 | | | 5 | 5 | 5 | | | 5 | | 5 | | 5 | | | 5 | 5 |
| | 4 | 1 | 1 | 3 | 3 | 5 | 5 | 3 | 4 | 2 | | 3 | 5 | | 4 | 3 | 4 | | | 5 | | 3 | | 4 | 2 | | 2 | 2 |
| | 2 | 1 | 2 | 3 | 4 | 5 | 4 | 2 | 3 | 2 | | 3 | 5 | | 4 | 3 | 4 | | | 4 | | 1 | | 3 | 2 | | 3 | 2 |
| | 1 | 1 | 1 | 3 | 3 | 5 | 4 | 2 | 3 | 1 | | 2 | 5 | | 4 | 3 | 3 | | | 4 | | 2 | | 3 | 1 | | 2 | 1 |
| | .5 | 1 | 1 | 2 | 1 | | 3 | 1 | | 2 | 1 | | 5 | | 3 | 1 | 4 | | | 3 | | 2 | | 1 | 1 | | 2 | |
| | .25 | 1 | 1 | 1 | 1 | | 4 | 1 | | 1 | 1 | | 2 | | 3 | 1 | 4 | | | 3 | | 1 | | 1 | 1 | | 1 | |
| | .125 | 1 | 1 | 1 | 1 | | 1 | 1 | | 1 | 1 | | 1 | | 1 | 1 | 1 | | | 1 | | 1 | | 1 | 1 | | 1 | |
| | .0625 | 1 | 1 | 1 | 1 | | 1 | 1 | | 1 | 1 | | 1 | | 1 | 1 | 1 | | | 1 | | 1 | | 1 | 1 | | 1 | |
| 14 | 8 | | | | 1 | | | | | 1 | 1 | | | | 1 | 1 | 1 | | | 1 | | | | | | | 1 | |
| 15 | 8 | | | | 1 | | | | | 2 | 1 | | | | 4 | 3 | 5 | | | 2 | | ° | | | | | 3 | |
| | 4 | 1 | 1 | 1 | 1 | | 1 | 1 | | 2 | 1 | | 2 | | 1 | 2 | 2 | | | 1 | | 1 | | 1 | 2 | | 1 | |
| | 2 | 1 | 1 | 1 | 1 | | 1 | 1 | | 1 | 1 | | 1 | | 1 | 1 | 1 | | | 1 | | 1 | | 1 | 1 | | 1 | |
| | 1 | 1 | 1 | 1 | 1 | | 1 | 1 | | 1 | 1 | | 1 | | 1 | 1 | 1 | | | 1 | | 1 | | 1 | 1 | | 1 | |
| | .5 | 1 | 1 | 1 | 1 | | 1 | 1 | | 1 | 1 | | 1 | | 1 | 1 | 1 | | | 1 | | 1 | | 1 | 1 | | 1 | |
| 16 | 8 | | | 5 | | | | | | 5 | 4 | | | | 4 | 5 | 5 | | | 5 | | | | | | | 5 | |
| | 4 | 3 | 2 | 4 | 2 | | 5 | 3 | | 4 | 2 | | 5 | | 5 | 5 | 5 | | | 5 | | 4 | | 4 | 3 | | 5 | |
| | 2 | 3 | 2 | 4 | 2 | | 5 | 3 | | 4 | 2 | | 5 | | 3 | 5 | 5 | | | 5 | | 2 | | 4 | 2 | | 5 | |
| | 1 | 2 | 1 | 3 | 1 | | 5 | 2 | | 4 | 1 | | 5 | | 4 | 2 | 5 | | | 5 | | | | 5 | 2 | | 4 | |
| | .5 | 1 | 1 | 1 | 1 | | 1 | 1 | | 1 | 1 | | 5 | | 1 | 1 | 1 | | | 1 | | 1 | | 1 | 1 | | 1 | |
| 17 | 8 | | | | 4 | | | | | 5 | 4 | | | | 5 | 5 | 5 | | | 5 | | | | | | | 5 | |
| | 4 | 3 | 3 | 3 | 2 | | 5 | 3 | | 5 | 3 | | 5 | | 5 | 5 | 5 | | | 5 | | 5 | | 5 | 5 | | 4 | |
| | 2 | 2 | 2 | 3 | 2 | | 5 | 3 | | 5 | 3 | | 5 | | 5 | 4 | 5 | | | 5 | | 4 | | 4 | 4 | | 3 | |
| | 1 | 1 | 1 | 2 | 2 | | 5 | 2 | | 4 | 2 | | 5 | | 4 | 2 | 5 | | | 5 | | 3 | | 4 | 1 | | 2 | |
| | .5 | 1 | 1 | 1 | 1 | | 4 | 1 | | 3 | 1 | | 4 | | 4 | 1 | 4 | | | 1 | | 1 | | 1 | 1 | | 1 | |
| 18 | 8 | | | | 1 | | | | | 4 | 2 | | | | 5 | 4 | 5 | | | 5 | | | | | | | 2 | |
| | 4 | 1 | 2 | 1 | 1 | | 4 | 4 | | 1 | 1 | | 3 | | 2 | 4 | 3 | | | 2 | | 1 | | 1 | 1 | | 3 | |
| | 2 | 1 | 1 | 1 | 1 | | 4 | 3 | | 1 | 1 | | 3 | | 2 | 1 | 1 | | | 1 | | 1 | | 1 | 1 | | 1 | |
| | 1 | 1 | 1 | 1 | 1 | | 1 | 1 | | 1 | 1 | | 1 | | 1 | 1 | 1 | | | 1 | | 1 | | 1 | 1 | | 1 | |
| | .5 | 1 | 1 | 1 | 1 | | 1 | 1 | | 1 | 1 | | 1 | | 1 | 1 | 1 | | | 1 | | 1 | | 1 | 1 | | 1 | |
| 19 | 8 | | | | 1 | | | | | 1 | 1 | | | | 5 | 3 | 5 | | | 5 | | | | | | | 2 | |
| | 4 | 1 | 1 | 1 | 1 | | 4 | 1 | | 3 | 1 | | 3 | | 3 | 1 | 5 | | | 1 | | 1 | | 1 | 1 | | 1 | |
| | 2 | 1 | 1 | 1 | 1 | | 3 | 1 | | 3 | 1 | | 3 | | 3 | 1 | 5 | | | 1 | | 1 | | 1 | 1 | | 1 | |
| | 1 | 1 | 1 | 1 | 1 | | 2 | 1 | | 2 | 1 | | 1 | | 3 | 1 | 4 | | | 1 | | 1 | | 1 | 1 | | 1 | |
| | .5 | 1 | 1 | 1 | 1 | | 2 | 1 | | 1 | 1 | | 1 | | 1 | 1 | 2 | | | 1 | | 1 | | 1 | 1 | | 1 | |
| 20 | 8 | | | | 1 | | | | | 4 | 1 | | | | 2 | 2 | 3 | | | 5 | | | | | | | 3 | |
| | 4 | 1 | 1 | 1 | 1 | | 5 | 1 | | 2 | 1 | | 2 | | 2 | 4 | 3 | | | 3 | | 1 | | 2 | 3 | | 1 | |
| | 2 | 1 | 1 | 1 | 1 | | 1 | 1 | | 1 | 1 | | 1 | | 1 | 1 | 1 | | | 1 | | 1 | | 1 | 1 | | 1 | |
| | 1 | 1 | 1 | 1 | 1 | | 1 | 1 | | 1 | 1 | | 1 | | 1 | 1 | 1 | | | 1 | | 1 | | 1 | 1 | | 1 | |
| | .5 | 1 | 1 | 1 | 1 | | 1 | 1 | | 1 | 1 | | 1 | | 1 | 1 | 1 | | | 1 | | 1 | | 1 | 1 | | 1 | |
| 21 | 8 | | | 5 | | | | | | 5 | 5 | | | | 5 | 5 | 5 | | | 5 | | | | | | | 5 | |
| | 8 | | | 2 | | | | | | 5 | 3 | | | | 5 | 5 | 5 | | | 5 | | | | | | | 4 | |
| | 4 | 2 | 1 | 2 | 2 | | 5 | 3 | | 5 | 3 | | 5 | | 5 | 4 | 5 | | | 5 | | 4 | | 5 | 4 | | 5 | |
| | 4 | 1 | 1 | 2 | 1 | | 5 | 1 | | 4 | 1 | | 5 | | 1 | 4 | 4 | | | 1 | | 1 | | 3 | 1 | | 1 | |

TABLE XIV-continued

PLANT SPECIES
Pre-emergence

| EX. NO. | Rate lbs/A | A | B | C | D | E | F | G | H | I | J | K | L | M | N | O | P | Q | R | S | T | U | V | W | X | Y | Z | a |
|---|---|---|---|---|---|---|---|---|---|---|---|---|---|---|---|---|---|---|---|---|---|---|---|---|---|---|---|---|
| | 2 | 1 | 1 | 4 | 3 | | 5 | 3 | | 4 | 3 | | 5 | | 4 | 2 | 4 | | | 5 | 3 | 3 | | 4 | | 4 | | |
| | 2 | 1 | 1 | 1 | 1 | | 3 | 1 | | 3 | 1 | | 2 | | 1 | 3 | 2 | | | 1 | 1 | 1 | | 1 | | 1 | | |
| | 1 | 1 | 1 | 2 | 1 | | 5 | 1 | | 2 | 2 | | 3 | | 4 | 1 | 4 | | | 3 | 2 | 3 | | 2 | | 3 | | |
| | 1 | 1 | 1 | 1 | 1 | | 1 | 1 | | 1 | 1 | | 1 | | 1 | 1 | 1 | | | 1 | 1 | 1 | | 1 | | 1 | | |
| | .5 | 1 | 1 | 1 | 1 | | 4 | 1 | | 2 | 1 | | 3 | | 1 | 1 | 3 | | | 1 | 1 | 1 | | 1 | | 1 | | |
| | .5 | 1 | 1 | 1 | 1 | | 1 | 1 | | 1 | 1 | | 1 | | 1 | 1 | 1 | | | 1 | 1 | 1 | | 1 | | 1 | | |
| 22 | 8 | | | 5 | | | | | | 5 | 5 | | | | 5 | 5 | 5 | | | 5 | | | | | | 5 | | |
| | 4 | 2 | 2 | 4 | 3 | | 5 | 3 | | 5 | 3 | | 5 | | 5 | 5 | 5 | | | 5 | 5 | | | 5 | | 4 | 5 | |
| | 2 | 1 | 1 | 3 | 2 | | 5 | 3 | | 4 | 3 | | 5 | | 4 | 4 | 5 | | | 5 | 5 | | | 5 | | 3 | 4 | |
| | 1 | 1 | 1 | 2 | 2 | | 5 | 3 | | 3 | 2 | | 5 | | 3 | 2 | 5 | | | 3 | 2 | | | 4 | | 2 | 4 | |
| | .5 | 1 | 1 | 1 | 1 | | 5 | 3 | | 3 | 2 | | 4 | | 2 | 1 | 4 | | | 4 | 2 | | | 2 | | 1 | 2 | |
| 23 | | | | 2 | | | | | | 2 | 1 | | | | 2 | 3 | 3 | | | 4 | | | | | | | 1 | |
| 24 | 8 | | | | | | | | | 5 | | 5 | | | 5 | 5 | 5 | | | 5 | 5 | 5 | | | | 5 | 5 | 5 |
| | 4 | 1 | 3 | 4 | 4 | 5 | 5 | 4 | 5 | 5 | | 2 | 4 | | 4 | 4 | 4 | | | 5 | 4 | 5 | 3 | | | 4 | 3 | 3 |
| | 2 | 1 | 2 | 3 | 3 | 5 | 5 | 3 | 3 | 5 | | 2 | 4 | | 5 | 5 | 4 | | | 4 | 3 | 4 | 2 | | | 2 | 2 | 2 |
| | 1 | 1 | 1 | 1 | 1 | 4 | 3 | 2 | 2 | 1 | | 1 | 4 | | 4 | 4 | 4 | | | 4 | 1 | 2 | 1 | | | 2 | 1 | 1 |
| | 1 | 1 | 1 | 1 | 1 | 3 | 3 | 1 | 2 | 1 | | 1 | 4 | | 2 | 4 | 5 | | | 1 | 1 | 1 | 1 | | | 1 | 1 | 1 |
| | .5 | 1 | 1 | 1 | 1 | 2 | 1 | 1 | 2 | 1 | | 1 | 3 | | 1 | 1 | 1 | | | 1 | 1 | 1 | 1 | | | 1 | 1 | 1 |
| | .25 | 1 | 1 | 1 | 1 | 2 | 1 | 1 | 1 | 1 | | 1 | 3 | | 1 | 1 | 1 | | | 1 | 1 | 1 | 1 | | | 1 | 1 | 1 |
| 25 | 8 | | | | | | | | | 5 | | 5 | | | 5 | 5 | 5 | | | 5 | 5 | 5 | | | | 5 | 5 | 5 |
| | 4 | 3 | 3 | 3 | 5 | 5 | 5 | 4 | 5 | 4 | | 3 | 5 | | 4 | 5 | 5 | | | 5 | 3 | 5 | 5 | | | 5 | 5 | 5 |
| | 2 | 1 | 2 | 3 | 3 | 5 | 5 | 4 | 4 | 3 | | 5 | 5 | | 3 | 3 | 4 | | | 5 | 2 | 5 | 3 | | | 5 | 3 | 3 |
| | 1 | 2 | 1 | 2 | 5 | 5 | 5 | 3 | 3 | 4 | | 3 | 5 | | 1 | 2 | 5 | | | 5 | 2 | 3 | 3 | | | 3 | 2 | 2 |
| | 1 | 1 | 1 | 1 | 1 | 4 | 5 | 3 | 3 | 2 | | 1 | 5 | | 2 | 4 | 4 | | | 5 | 2 | 4 | 3 | | | 4 | 3 | 1 |
| | .5 | 1 | 1 | 1 | 3 | 3 | 1 | 1 | | 1 | | 1 | 4 | | 1 | 3 | 3 | | | 1 | 1 | 1 | 1 | | | 1 | 1 | 1 |
| | .2 | 1 | 1 | 1 | 1 | 1 | 1 | 1 | 1 | 1 | | 1 | 2 | | 1 | 2 | 2 | | | 1 | 1 | 1 | 1 | | | 1 | 1 | 1 |
| 26 | 8 | | | | | | | | | 5 | | | | | 5 | 5 | 5 | | | 5 | 5 | 5 | | | | 5 | 5 | 5 |
| | 4 | 3 | 5 | 5 | 5 | 5 | 5 | 5 | 5 | 5 | | 4 | 5 | | 5 | 5 | 5 | | | 5 | 5 | 5 | 5 | | | 5 | 5 | 5 |
| | 2 | 2 | 3 | 5 | 4 | 5 | 5 | 3 | 3 | 2 | | 3 | 5 | | 4 | 5 | 5 | | | 5 | 3 | 5 | 4 | | | 3 | 2 | 2 |
| | 1 | 2 | 2 | 1 | 4 | 4 | 5 | 3 | 3 | 2 | | 2 | 4 | | 1 | 3 | 4 | | | 2 | 3 | 3 | 3 | | | 1 | 4 | |
| | 1 | 1 | 2 | 4 | 3 | 5 | 5 | 2 | 3 | 2 | | 2 | 5 | | 3 | 4 | 5 | | | 5 | 3 | 4 | 2 | | | 4 | 2 | |
| | .5 | 1 | 1 | 1 | 3 | 2 | 1 | 1 | 1 | 1 | | 1 | 4 | | 1 | 2 | 3 | | | 1 | 1 | 1 | 1 | | | 1 | 1 | |
| | .25 | 1 | 1 | 1 | 1 | 1 | 1 | 1 | 1 | 1 | | 1 | 4 | | 1 | 1 | 1 | | | 1 | 1 | 1 | 1 | | | 1 | 1 | |
| 27 | 8 | | | | | | | | | 5 | | 5 | | | 5 | 5 | 5 | | | 5 | 5 | 5 | | | | 5 | 5 | |
| | 8 | | | | | | | | | 5 | | 5 | | | 5 | 5 | 5 | | | 5 | 5 | 5 | | | | 5 | 5 | |
| | 8 | | | | | | | | | 5 | | 4 | | | 5 | 5 | 5 | | | 5 | 5 | 5 | | | | 5 | 5 | |
| | 4 | 2 | 3 | 4 | 5 | 5 | 5 | 5 | 5 | 4 | | 3 | 5 | | 4 | 5 | 5 | | | 5 | 5 | 5 | 5 | | | 5 | 5 | |
| | 4 | 1 | 1 | 1 | 2 | 5 | 5 | 2 | 2 | 2 | | 3 | 4 | | 3 | 5 | 4 | | | 5 | 4 | 3 | 3 | | | 2 | 4 | |
| | 2 | 1 | 1 | 2 | 5 | 5 | 5 | 5 | 5 | 4 | | 2 | 5 | | 3 | 4 | 5 | | | 5 | 2 | 5 | 2 | | | 5 | 4 | |
| | 2 | 1 | 1 | 1 | 5 | 5 | 5 | 2 | 4 | 2 | | 2 | 4 | | 3 | 4 | 4 | | | 4 | 2 | 2 | 2 | | | 4 | 1 | |
| | 1 | 1 | 1 | 2 | 3 | 3 | 5 | 1 | 4 | 3 | | 1 | 4 | | 3 | 3 | 5 | | | 4 | 2 | 3 | 1 | | | 3 | 2 | |
| | 1 | 1 | 1 | 1 | 1 | 2 | 4 | 1 | 2 | 2 | | 2 | 5 | | 1 | 1 | 4 | | | 1 | 1 | 1 | 1 | | | 2 | 1 | |
| 28 | 8 | | | | | | | | | 5 | | 4 | | | 5 | 5 | 5 | | | 5 | 5 | 4 | | | | 5 | 4 | |
| | 4 | 1 | 1 | 1 | 1 | 5 | 5 | 3 | 3 | 3 | | 2 | 5 | | 3 | 4 | 5 | | | 5 | 4 | 5 | 4 | | | 4 | 4 | |
| | 2 | 1 | 1 | 1 | 2 | 5 | 5 | 2 | 2 | 2 | | 2 | 5 | | 3 | 2 | 4 | | | 3 | 3 | 4 | 4 | | | 5 | 2 | |
| | 1 | 1 | 1 | 1 | 1 | 5 | 4 | 1 | 2 | 1 | | 1 | 5 | | 1 | 3 | 4 | | | 3 | 1 | 3 | 2 | | | 1 | 1 | |
| 29 | 8 | | | | | | | | | 4 | | 4 | | | 4 | 5 | 4 | | | 5 | 4 | 5 | | | | 4 | 4 | |
| | 8 | | | 3 | | | | | | 5 | 4 | | | | 5 | 5 | 5 | | | 5 | | | | | | 5 | | |
| | 4 | 1 | 1 | 1 | 4 | 5 | 5 | 3 | 3 | 4 | | 3 | 5 | | 3 | 5 | 4 | | | 5 | 3 | 3 | 5 | | | 2 | 3 | |
| | 2 | 1 | 1 | 1 | 2 | 2 | 5 | 2 | 2 | 3 | | 3 | 4 | | 1 | 3 | 4 | | | 4 | 2 | 2 | 4 | | | 2 | 2 | |
| | 1 | 1 | 1 | 1 | 1 | 1 | 3 | 1 | 1 | 1 | | 1 | 1 | | 1 | 1 | 4 | | | 1 | 1 | 1 | 1 | | | 1 | 1 | |
| 30 | 8 | | | | | | | | | 5 | | 3 | | | 4 | 4 | 5 | | | 5 | 4 | 5 | | | | 5 | 4 | |
| | 4 | 2 | 1 | 1 | 2 | 5 | 5 | 1 | 2 | 3 | | 3 | 4 | | 3 | 4 | 5 | | | 5 | 3 | 3 | 2 | | | 2 | 4 | |
| | 2 | 1 | 1 | 1 | 2 | 2 | 3 | 1 | 2 | 2 | | 2 | 5 | | 1 | 1 | 5 | | | 5 | 2 | 1 | 1 | | | 2 | 3 | |
| | 1 | 1 | 1 | 1 | 2 | 2 | 2 | 1 | 1 | 1 | | 2 | 1 | | 1 | 1 | 5 | | | 3 | 1 | 1 | 1 | | | 1 | 1 | |
| 32 | 8 | | | | | | | | | 5 | | 5 | | | 5 | 5 | 5 | | | 5 | 5 | 5 | | | | 5 | 5 | |
| | 4 | 2 | 2 | 3 | 4 | 5 | 5 | 5 | 4 | 5 | | 3 | 5 | | 4 | 5 | 4 | | | 5 | 5 | 5 | 5 | | | 4 | 3 | |
| | 2 | 1 | 1 | 1 | 4 | 5 | 5 | 3 | 4 | 4 | | 3 | 4 | | 3 | 4 | 4 | | | 4 | 4 | 4 | 3 | | | 3 | 2 | |
| | 1 | 1 | 1 | 1 | 1 | 1 | 3 | 3 | 3 | 2 | | 2 | 1 | | 1 | 1 | 5 | | | 2 | 1 | 1 | 2 | | | 1 | 1 | |
| 34 | 8 | | | | | | | | | 4 | | | 1 | | 4 | 2 | 5 | | | 4 | 2 | 2 | | | | 2 | 2 | |
| | 4 | 1 | 1 | 3 | 1 | | 5 | 3 | | | | | 3 | | 5 | 2 | 5 | | | 5 | 3 | 1 | 4 | | | 1 | 1 | |
| | 2 | 1 | 1 | 1 | 1 | | 5 | 3 | | | | | 3 | | 5 | 3 | 5 | | | 4 | 3 | 1 | 1 | | | 1 | 1 | |
| | 1 | 1 | 1 | 1 | 1 | | 5 | 2 | | | | | 3 | | 3 | 1 | 5 | | | 1 | 2 | 1 | 1 | | | 1 | 1 | |
| 36 | 8 | | | | | | | | | 5 | | | 5 | | 5 | 5 | 5 | | | 5 | 5 | 5 | | | | 4 | 3 | |
| | 4 | 4 | 3 | 5 | 4 | | 5 | 5 | | | | | 5 | | 5 | 5 | 5 | | | 5 | 5 | 5 | 5 | | | 5 | 4 | |
| | 2 | 3 | 1 | 3 | 2 | | 5 | 5 | | | | | 5 | | 5 | 4 | 5 | | | 5 | 5 | 4 | 5 | | | 3 | 3 | |
| | 1 | 1 | 1 | 3 | 1 | | 5 | 1 | | | | | 1 | | 4 | 1 | 4 | | | 3 | 1 | 2 | 2 | | | 1 | 1 | |
| 38 | 8 | | | 1 | | | | | | 2 | 1 | | | | 2 | 1 | 4 | | | 4 | | | | | | 1 | | |
| | 8 | | | 1 | | | | | | 2 | 1 | | | | 2 | 1 | 4 | | | 4 | | | | | | 1 | | |
| | 4 | 1 | 1 | 1 | 1 | | 1 | 1 | | 2 | 1 | | 5 | | 3 | 1 | 3 | | | 1 | 1 | 1 | 1 | | | 1 | 1 | |
| | 2 | 1 | 1 | 1 | 1 | | 1 | 1 | | 1 | 1 | | 1 | | 1 | 1 | 1 | | | 1 | 1 | 1 | 1 | | | 1 | 1 | |
| | 1 | 1 | 1 | 1 | 1 | | 1 | 1 | | 1 | 1 | | 1 | | 1 | 1 | 1 | | | 1 | 1 | 1 | 1 | | | 1 | 1 | |
| | .5 | 1 | 1 | 1 | 1 | | 1 | 1 | | 1 | 1 | | 1 | | 1 | 1 | 1 | | | 1 | 1 | 1 | 1 | | | 1 | 1 | |
| 39 | 8 | | | 1 | | | | | | 1 | 1 | | | | 1 | 1 | 1 | | | 1 | | | | | | 1 | | |
| | 8 | | | 1 | | | | | | 1 | 1 | | | | 1 | 1 | 1 | | | 1 | | | | | | 1 | | |
| 41 | 8 | | | | | | | | | 5 | 1 | | | | 2 | 5 | 5 | | | 3 | | | | | | 3 | | |
| | 4 | 1 | 1 | 1 | 1 | | 4 | 1 | | 5 | 2 | | 5 | | 1 | 5 | 5 | | | 1 | | 2 | | 4 | | 2 | 1 | |
| | 2 | 1 | 1 | 1 | 1 | | 5 | 1 | | 3 | 1 | | 4 | | 1 | 3 | 3 | | | 1 | | 1 | | 1 | | 1 | 1 | |

TABLE XIV-continued

| EX. NO. | Rate lbs/A | \multicolumn{27}{c}{PLANT SPECIES Pre-emergence} |
|---|---|---|---|---|---|---|---|---|---|---|---|---|---|---|---|---|---|---|---|---|---|---|---|---|---|---|---|
| | | A | B | C | D | E | F | G | H | I | J | K | L | M | N | O | P | Q | R | S | T | U | V | W | X | Y | Z | a |
| | 1 | 1 | 1 | 1 | 1 | | 1 | 1 | | 1 | 1 | | 1 | | 1 | 1 | 1 | | | 1 | | 1 | | 1 | 1 | | 1 | |
| | .5 | 1 | 1 | 1 | 1 | | 1 | 1 | | 1 | 1 | | 1 | | 1 | 1 | 1 | | | 1 | | 1 | | 1 | 1 | | 1 | |
| 43 | 8 | | | 3 | | | | | | 1 | 1 | | | | 1 | 1 | 1 | | | 1 | | | | | | | 1 | |
| 44 | 8 | | | 3 | | | | | | 1 | 1 | | | | 1 | 4 | 4 | | | 1 | | | | | | | 1 | |
| | 4 | 2 | 2 | 3 | 1 | | 2 | 2 | | 1 | 1 | | 5 | | 1 | 1 | 5 | | | 1 | | 1 | | 1 | 1 | | 1 | |
| | 2 | 1 | 1 | 2 | 1 | | 1 | 1 | | 1 | 1 | | 4 | | 1 | 1 | 2 | | | 1 | | 1 | | 1 | 1 | | 1 | |
| | 1 | 1 | 1 | 1 | 1 | | 1 | 1 | | 1 | 1 | | 1 | | 1 | 1 | 1 | | | 1 | | 1 | | 1 | 1 | | 1 | |
| | .5 | 1 | 1 | 1 | 1 | | 1 | 1 | | 1 | 1 | | 1 | | 1 | 1 | 1 | | | 1 | | 1 | | 1 | 1 | | 1 | |
| 45 | 8 | | | 1 | | | | | | 1 | 1 | | | | 1 | 1 | 1 | | | 1 | | | | | | | 1 | |
| 47 | 8 | | | 1 | | | | | | 5 | 2 | | | | 5 | 5 | 5 | | | 5 | | | | | | | 3 | |
| | 4 | 3 | 2 | 1 | 1 | | 5 | 2 | | 2 | 2 | | 5 | | 2 | 2 | 3 | | | 3 | | 3 | | 1 | 3 | | 1 | |
| | 2 | 1 | 1 | 1 | 1 | | 4 | 1 | | 3 | 1 | | 5 | | 2 | 1 | 5 | | | 2 | | 2 | | 1 | 1 | | 1 | |
| | 1 | 1 | 1 | 1 | 1 | | 1 | 1 | | 1 | 1 | | 1 | | 1 | 1 | 1 | | | 1 | | 1 | | 1 | 1 | | 1 | |
| | .5 | 1 | 1 | 1 | 1 | | 1 | 1 | | 1 | 1 | | 1 | | 1 | 1 | 1 | | | 1 | | 1 | | 1 | 1 | | 1 | |
| 49 | 8 | | | 2 | | | | | | 5 | 2 | | | | 5 | 4 | 5 | | | 5 | | | | | | | 5 | |
| | 4 | 3 | 1 | 1 | 3 | | 5 | 2 | | 5 | 3 | | 5 | | 2 | 5 | 5 | | | 5 | | 5 | | 4 | 5 | | 3 | |
| | 2 | 3 | 1 | 1 | 1 | | 5 | 2 | | 3 | 1 | | 5 | | 1 | 5 | 5 | | | 5 | | 3 | | 2 | 3 | | 1 | |
| | 1 | 2 | 1 | 1 | 1 | | 5 | 1 | | 1 | 1 | | 5 | | 2 | 1 | 3 | | | 4 | | 3 | | 1 | 1 | | 1 | |
| | .5 | 1 | 1 | 1 | 1 | | 4 | 1 | | 1 | 1 | | 5 | | 1 | 1 | 3 | | | 1 | | 1 | | 1 | 1 | | 1 | |
| 50 | 8 | | | 2 | | | | | | 5 | 2 | | | | 5 | 4 | 5 | | | 5 | | | | | | | 3 | |
| | 4 | 4 | 1 | 3 | 3 | | 5 | 2 | | 5 | 3 | | 5 | | 4 | 5 | 5 | | | 5 | | 3 | | 3 | 4 | | 3 | |
| | 2 | 3 | 1 | 2 | 3 | | 5 | 1 | | 3 | 2 | | 5 | | 3 | 3 | 3 | | | 3 | | 3 | | 2 | 3 | | 3 | |
| | 1 | 3 | 1 | 1 | 2 | | 3 | 1 | | 2 | 1 | | 5 | | 2 | 1 | 3 | | | 2 | | 2 | | 1 | 1 | | 2 | |
| | .5 | 1 | 1 | 1 | 1 | | 1 | 1 | | 1 | 1 | | 1 | | 1 | 1 | 1 | | | 1 | | 1 | | 1 | 1 | | 1 | |
| 51 | 8 | | | 1 | | | | | | 5 | 1 | | | | 5 | 4 | 5 | | | 5 | | | | | | | 3 | |
| | 4 | 2 | 1 | 3 | 3 | | 5 | 1 | | 4 | 2 | | 5 | | 5 | 4 | 5 | | | 5 | | 4 | | 4 | 3 | | 2 | |
| | 2 | 1 | 1 | 1 | 1 | | 3 | 1 | | 1 | 1 | | 2 | | 3 | 2 | 5 | | | 5 | | 4 | | 3 | 1 | | 3 | |
| | 1 | 1 | 1 | 1 | 1 | | 1 | 1 | | 1 | 1 | | 1 | | 1 | 1 | 3 | | | 4 | | 1 | | 2 | 1 | | 3 | |
| | .5 | 1 | 1 | 1 | 1 | | 1 | 1 | | 1 | 1 | | 1 | | 2 | 1 | 1 | | | 3 | | 1 | | 1 | 1 | | 1 | |

TABLE XV

| EX. NO. | Rate lbs/A | \multicolumn{27}{c}{PLANT SPECIES Post-emergence} |
|---|---|---|---|---|---|---|---|---|---|---|---|---|---|---|---|---|---|---|---|---|---|---|---|---|---|---|---|
| | | A | B | C | D | E | F | G | H | I | J | K | L | M | N | O | P | Q | R | S | T | U | V | W | X | Y | Z | a |
| 1 | 8 | | | | | | | | | 5 | | 5 | | | 5 | 5 | 5 | | | 5 | | 5 | | 5 | | | 5 | 5 |
| | 4 | | | | | | | | | 5 | | 5 | | | 5 | 5 | 5 | | | 5 | | 5 | | 5 | | | 5 | 5 |
| | 2 | | | | | | | | | 5 | | 3 | | | 2 | 5 | 4 | | | 4 | | 3 | | 4 | | | 4 | 5 |
| | 1 | | | | | | | | | 5 | | 4 | | | 3 | 5 | 4 | | | 4 | | 3 | | 5 | | | 4 | 5 |
| | 1 | | | | | | | | | 5 | | 1 | | | 1 | 5 | 4 | | | 3 | | 1 | | 4 | | | 2 | 5 |
| | .5 | | | | | | | | | 5 | | 1 | | | 1 | 5 | 3 | | | 3 | | 1 | | 2 | | | 1 | 5 |
| | .25 | | | | | | | | | 3 | | 1 | | | 1 | 4 | 3 | | | 2 | | 1 | | 1 | | | 1 | 3 |
| 4 | 8 | | | | | | | | | 5 | | 5 | | | 5 | 5 | 5 | | | 5 | | 5 | | 5 | | | 5 | 5 |
| | 4 | | | | | | | | | 5 | | 5 | | | 5 | 5 | 5 | | | 5 | | 4 | | 5 | | | 5 | 5 |
| | 2 | | | | | | | | | 5 | | 5 | | | 5 | 5 | 5 | | | 5 | | 4 | | 5 | | | 5 | 5 |
| | 1 | | | | | | | | | 5 | | 5 | | | 4 | 5 | 5 | | | 5 | | 4 | | 4 | | | 4 | 5 |
| | .5 | 3 | 2 | 3 | 3 | | 4 | 2 | | 5 | 2 | | 5 | | 5 | 5 | 5 | | | 5 | | 3 | | 2 | 5 | | 3 | |
| | .25 | 4 | 1 | 2 | 2 | | 3 | 1 | | 4 | 1 | | 5 | | 4 | 5 | 5 | | | 3 | | 2 | | 2 | 4 | | 1 | |
| | .125 | 4 | 1 | 2 | 1 | | 3 | 1 | | 2 | 1 | | 5 | | 3 | 4 | 4 | | | 3 | | 1 | | 1 | 2 | | 1 | |
| | .0625 | 2 | 1 | 2 | 1 | | 1 | 1 | | 1 | 1 | | 4 | | 1 | 4 | 3 | | | 1 | | 1 | | 1 | 1 | | 1 | |
| 5 | 8 | | | | | | | | | 5 | | 4 | | | 5 | 5 | 5 | | | 4 | | 2 | | 3 | | | 4 | 5 |
| | 4 | | | | | | | | | 5 | | 2 | | | 2 | 5 | 3 | | | 3 | | 2 | | 3 | | | 3 | 4 |
| | 2 | | | | | | | | | 5 | | 2 | | | 2 | 5 | 3 | | | 3 | | 1 | | 2 | | | 3 | 3 |
| | 1 | | | | | | | | | 3 | | 1 | | | 1 | 4 | 2 | | | 2 | | 1 | | 2 | | | 2 | 3 |
| 6 | 8 | | | | | | | | | 5 | | 5 | | | 5 | 5 | 5 | | | 5 | | 5 | | 5 | | | 5 | 5 |
| | 4 | | | | | | | | | 5 | | 5 | | | 5 | 5 | 5 | | | 5 | | 5 | | 5 | | | 4 | 5 |
| | 2 | | | | | | | | | 5 | | 5 | | | 5 | 5 | 5 | | | 5 | | 5 | | 5 | | | 4 | 5 |
| | 1 | | | | | | | | | 5 | | 5 | | | 5 | 5 | 4 | | | 5 | | 5 | | 5 | | | 4 | 5 |
| | .5 | 5 | 4 | 3 | 2 | | 3 | 2 | | 5 | 1 | | 5 | | 5 | 5 | 4 | | | 5 | | 3 | | 4 | 5 | | 2 | |
| | .25 | 4 | 1 | 2 | 2 | | 2 | 1 | | 5 | 1 | | 4 | | 5 | 4 | 4 | | | 5 | | 3 | | 3 | 5 | | 2 | |
| | .125 | 5 | 1 | 2 | 2 | | 2 | 1 | | 4 | 1 | | 4 | | 2 | 4 | 3 | | | 4 | | 2 | | 3 | 4 | | 2 | |
| | .0625 | 5 | 1 | 1 | 1 | | 1 | 2 | | 1 | 1 | | 4 | | 2 | 3 | 3 | | | 1 | | 1 | | 1 | 1 | | 1 | |
| 7 | 8 | | | | | | | | | 5 | | 3 | | | 3 | 4 | 3 | | | 5 | | 3 | | 5 | | | 4 | 4 |
| | 4 | | | | | | | | | 5 | | 5 | | | 3 | 5 | 3 | | | 3 | | 2 | | 3 | | | 3 | 4 |
| | 2 | | | | | | | | | 4 | | 3 | | | 2 | 5 | 3 | | | 3 | | 1 | | 3 | | | 2 | 3 |
| | 1 | | | | | | | | | 1 | | 1 | | | 1 | 3 | 2 | | | 3 | | 1 | | 1 | | | 1 | 1 |
| 8 | 8 | | | | | | | | | 5 | | 4 | | | 5 | 5 | 5 | | | 5 | | 5 | | 5 | | | 4 | 5 |
| | 4 | | | | | | | | | 5 | | 5 | | | 4 | 5 | 4 | | | 5 | | 3 | | 5 | | | 4 | 5 |
| | 2 | | | | | | | | | 5 | | 5 | | | 3 | 5 | 3 | | | 5 | | 4 | | 5 | | | 4 | 5 |
| | 1 | | | | | | | | | 5 | | 5 | | | 3 | 5 | 3 | | | 5 | | 4 | | 5 | | | 4 | 5 |
| | .5 | 2 | 1 | 3 | 2 | | 4 | 2 | | 5 | 2 | | 5 | | 1 | 5 | 1 | | | 2 | | 2 | | 3 | 5 | | 2 | |
| | .25 | 1 | 1 | 2 | 2 | | 1 | 1 | | 4 | 1 | | 5 | | 1 | 5 | 1 | | | 1 | | 1 | | 1 | 3 | | 1 | |
| | .125 | 1 | 1 | 2 | 1 | | 1 | 1 | | 1 | 1 | | 3 | | 1 | 4 | 1 | | | 1 | | 1 | | 1 | 1 | | 1 | |
| | .0625 | 1 | 1 | 1 | 1 | | 1 | 1 | | 1 | 1 | | 1 | | 1 | 1 | 1 | | | 1 | | 1 | | 1 | 1 | | 1 | |
| 9 | 8 | | | | | | | | | 5 | | 3 | | | 4 | 5 | 4 | | | 2 | | 4 | | 4 | | | 4 | 5 |
| | 4 | | | | | | | | | 1 | | 1 | | | 1 | 1 | 1 | | | 1 | | 1 | | 1 | | | 1 | 1 |

TABLE XV-continued

PLANT SPECIES
Post-emergence

| EX. NO. | Rate lbs/A | A | B | C | D | E | F | G | H | I | J | K | L | M | N | O | P | Q | R | S | T | U | V | W | X | Y | Z | a |
|---|---|---|---|---|---|---|---|---|---|---|---|---|---|---|---|---|---|---|---|---|---|---|---|---|---|---|---|---|
|  | 2 |   |   |   |   |   |   |   |   | 1 |   | 1 |   |   | 1 | 1 | 1 |   |   | 1 | 1 | 1 |   |   |   | 1 | 1 |
|  | 1 |   |   |   |   |   |   |   |   | 1 |   | 1 |   |   | 1 | 1 | 1 |   |   | 1 | 1 | 1 |   |   |   | 1 | 1 |
| 10 | 8 |   |   |   |   |   |   |   |   | 4 |   | 3 |   |   | 4 | 5 | 4 |   |   | 4 | 3 | 4 |   |   |   | 4 | 5 |
|  | 4 |   |   |   |   |   |   |   |   | 2 |   | 1 |   |   | 1 | 4 | 2 |   |   | 3 | 1 | 2 |   |   |   | 2 | 2 |
|  | 2 |   |   |   |   |   |   |   |   | 1 |   | 1 |   |   | 1 | 3 | 1 |   |   | 2 | 1 | 1 |   |   |   | 1 | 1 |
|  | 1 |   |   |   |   |   |   |   |   | 1 |   | 1 |   |   | 1 | 1 | 1 |   |   | 1 | 1 | 1 |   |   |   | 1 | 1 |
| 11 | 8 |   |   |   |   |   |   |   |   | 4 |   | 2 |   |   | 2 | 5 | 4 |   |   | 4 | 1 | 3 |   |   |   | 2 | 4 |
|  | 4 |   |   |   |   |   |   |   |   | 3 |   | 1 |   |   | 1 | 3 | 2 |   |   | 3 | 1 | 3 |   |   |   | 2 | 4 |
|  | 2 |   |   |   |   |   |   |   |   | 2 |   | 1 |   |   | 1 | 3 | 1 |   |   | 4 | 1 | 2 |   |   |   | 1 | 1 |
|  | 1 |   |   |   |   |   |   |   |   | 1 |   | 1 |   |   | 1 | 2 | 1 |   |   | 3 | 1 | 2 |   |   |   | 1 | 1 |
| 13 | 8 |   |   |   |   |   |   |   |   | 5 |   | 5 |   |   | 5 | 5 | 5 |   |   | 5 | 5 | 5 |   |   |   | 5 | 5 |
|  | 4 |   |   |   |   |   |   |   |   | 5 |   | 5 |   |   | 5 | 5 | 5 |   |   | 5 | 5 | 5 |   |   |   | 5 | 5 |
|  | 2 |   |   |   |   |   |   |   |   | 5 |   | 4 |   |   | 5 | 5 |   |   |   | 5 | 4 | 5 |   |   |   | 5 | 5 |
|  | 2 |   |   |   |   |   |   |   |   | 4 |   | 2 |   |   | 4 | 5 | 5 |   |   | 3 |   | 1 |   |   |   | 2 | 5 |
|  | 1 |   |   |   |   |   |   |   |   | 5 |   | 4 |   |   | 5 | 5 |   |   |   | 5 | 4 | 5 |   |   |   | 4 | 5 |
|  | 1 |   |   |   |   |   |   |   |   | 5 |   | 3 |   |   | 5 | 5 | 5 |   |   | 5 | 5 | 5 |   |   |   | 4 | 5 |
|  | .5 | 3 | 2 | 4 | 2 |   | 5 | 2 |   | 5 | 2 |   | 5 |   | 2 | 5 | 5 |   |   | 5 | 3 | 4 |   | 5 |   | 3 |   |
|  | .5 |   |   |   |   |   |   |   |   | 5 |   | 4 |   |   | 5 | 5 | 5 |   |   | 5 | 4 | 5 |   |   |   | 4 | 5 |
|  | .25 | 4 | 2 | 2 | 2 |   | 4 | 1 |   | 4 | 1 |   | 5 |   | 3 | 5 | 5 |   |   | 3 | 3 | 2 |   | 5 |   | 3 |   |
|  | .25 |   |   |   |   |   |   |   |   | 5 |   | 3 |   |   | 4 | 5 | 4 |   |   | 5 | 2 | 5 |   |   |   | 2 | 5 |
|  | .125 | 2 | 1 | 2 | 2 |   | 3 | 1 |   | 2 | 1 |   | 5 |   | 3 | 5 | 4 |   |   | 3 | 3 | 2 |   | 2 |   | 2 |   |
|  | .125 |   |   |   |   |   |   |   |   | 4 |   | 2 |   |   | 4 | 5 | 4 |   |   | 5 | 1 | 1 |   |   |   | 2 | 5 |
|  | .0625 | 1 | 1 | 2 | 1 |   |   | 1 |   | 1 | 1 |   | 5 |   | 4 | 3 | 4 |   |   | 2 | 2 | 1 |   | 1 |   | 1 |   |
|  | .0625 |   |   |   |   |   |   |   |   | 1 |   | 1 |   |   | 2 | 3 | 2 |   |   | 3 | 1 | 1 |   |   |   | 1 | 4 |
| 14 | 8 |   |   | 1 |   |   |   |   |   | 1 | 1 |   |   |   | 1 | 1 | 1 |   |   | 1 |   |   |   |   |   | 1 |   |
| 15 | 8 |   |   | 3 |   |   |   |   |   | 5 | 2 |   |   |   | 3 | 5 | 5 |   |   | 3 |   |   |   |   |   | 3 |   |
|  | 4 | 2 | 1 | 2 | 1 |   | 2 | 1 |   | 4 | 1 |   | 3 |   | 4 | 4 | 5 |   |   | 2 | 1 | 2 |   | 2 |   | 1 |   |
|  | 2 | 1 | 1 | 2 | 1 |   | 1 | 1 |   | 1 | 1 |   | 3 |   | 2 | 3 | 3 |   |   | 1 | 1 | 1 |   | 1 |   | 1 |   |
|  | 1 | 1 | 1 | 1 | 1 |   | 1 | 1 |   | 1 | 1 |   | 1 |   | 1 | 1 | 1 |   |   | 1 | 1 | 1 |   | 1 |   | 1 |   |
|  | .5 | 1 | 1 | 1 | 1 |   | 1 | 1 |   | 1 | 1 |   | 1 |   | 1 | 1 | 1 |   |   | 1 | 1 | 1 |   | 1 |   | 1 |   |
| 16 | 8 |   |   | 5 |   |   |   |   |   | 5 | 4 |   |   |   | 5 | 5 | 5 |   |   | 5 |   |   |   |   |   | 5 |   |
|  | 4 | 3 | 3 | 4 | 3 |   | 5 | 2 |   | 5 | 3 |   | 5 |   | 5 | 5 | 5 |   |   | 5 | 4 | 5 |   | 5 |   | 4 |   |
|  | 2 | 4 | 2 | 3 | 2 |   | 5 | 2 |   | 5 | 2 |   | 5 |   | 3 | 5 | 5 |   |   | 5 | 4 | 3 |   | 5 |   | 4 |   |
|  | 1 | 3 | 2 | 2 | 2 |   | 4 | 2 |   | 5 | 1 |   | 5 |   | 3 | 5 | 5 |   |   | 5 | 4 | 2 |   | 5 |   | 4 |   |
|  | .5 | 3 | 2 | 2 | 1 |   | 4 | 1 |   | 5 | 1 |   | 5 |   | 2 | 5 | 4 |   |   | 3 | 2 | 1 |   | 3 |   | 4 |   |
| 17 | 8 |   |   | 4 |   |   |   |   |   | 5 | 4 |   |   |   | 5 | 5 | 5 |   |   | 5 |   |   |   |   |   | 4 |   |
|  | 4 | 4 | 4 | 4 | 4 |   | 5 | 3 |   | 5 | 4 |   | 5 |   | 4 | 5 | 5 |   |   | 5 | 4 | 4 |   | 5 |   | 4 |   |
|  | 2 | 4 | 4 | 4 | 4 |   | 5 | 4 |   | 5 | 4 |   | 5 |   | 4 | 5 | 4 |   |   | 5 | 4 | 4 |   | 5 |   | 4 |   |
|  | 1 | 4 | 3 | 4 | 4 |   | 5 | 3 |   | 5 | 4 |   | 5 |   | 3 | 5 | 4 |   |   | 5 | 4 | 3 |   | 5 |   | 4 |   |
|  | .5 | 4 | 2 | 3 | 2 |   | 5 | 3 |   | 5 | 3 |   | 5 |   | 2 | 4 | 3 |   |   | 3 | 1 | 2 |   | 5 |   | 3 |   |
| 18 | 8 |   |   | 3 |   |   |   |   |   | 5 | 3 |   |   |   | 3 | 5 | 5 |   |   | 2 |   |   |   |   |   | 4 |   |
|  | 4 | 2 | 4 | 2 | 2 |   | 4 | 2 |   | 3 | 2 |   | 5 |   | 2 | 5 | 5 |   |   | 2 | 1 | 1 |   | 5 |   |   |   |
|  | 2 | 2 | 3 | 2 | 1 |   | 1 | 2 |   | 1 | 1 |   | 3 |   | 2 | 3 | 3 |   |   | 2 | 1 | 1 |   | 3 |   |   |   |
|  | 1 | 1 | 2 | 2 | 1 |   | 2 | 2 |   | 1 | 1 |   | 3 |   | 1 | 3 | 2 |   |   | 1 | 1 | 1 |   | 2 |   |   |   |
|  | .5 | 1 | 2 | 2 | 1 |   | 1 | 1 |   | 1 | 1 |   | 1 |   | 1 | 1 | 1 |   |   | 1 | 1 | 1 |   | 1 |   |   |   |
| 19 | 8 |   |   | 2 |   |   |   |   |   | 4 | 2 |   |   |   | 4 | 5 | 5 |   |   | 4 |   |   |   |   |   | 3 |   |
|  | 4 | 3 | 3 | 3 | 3 |   | 4 | 2 |   | 5 | 2 |   | 5 |   | 3 | 4 | 5 |   |   | 3 | 2 | 3 |   | 4 |   | 4 |   |
|  | 2 | 3 | 2 | 2 | 2 |   | 4 | 2 |   | 4 | 1 |   | 5 |   | 3 | 3 | 5 |   |   | 3 | 2 | 2 |   | 3 |   | 3 |   |
|  | 1 | 3 | 2 | 1 | 1 |   | 4 | 2 |   | 3 | 1 |   | 5 |   | 2 | 3 | 3 |   |   | 3 | 1 | 1 |   | 3 |   | 2 |   |
|  | .5 | 3 | 2 | 1 | 1 |   | 4 | 2 |   | 1 | 1 |   | 4 |   | 1 | 2 | 2 |   |   | 2 | 1 | 1 |   | 2 |   | 1 |   |
| 20 | 8 |   |   | 3 |   |   |   |   |   | 5 | 2 |   |   |   | 2 | 5 | 5 |   |   | 5 |   |   |   |   |   | 4 |   |
|  | 4 | 2 | 2 | 3 | 1 | - | 5 | 1 |   | 5 | 2 |   | 5 |   | 3 | 5 | 4 |   |   | 3 | 1 | 2 |   | 5 |   | 3 |   |
|  | 2 | 2 | 2 | 2 | 1 |   | 4 | 1 |   | 5 | 1 |   | 5 |   | 2 | 5 | 4 |   |   | 3 | 1 | 1 |   | 5 |   | 3 |   |
|  | 1 | 1 | 2 | 2 | 1 |   | 3 | 1 |   | 2 | 1 |   | 4 |   | 2 | 5 | 2 |   |   | 1 | 1 | 1 |   | 3 |   | 2 |   |
|  | .5 | 1 | 2 | 2 | 1 |   | 2 | 1 |   | 1 | 1 |   | 3 |   | 1 | 4 | 1 |   |   | 1 | 1 | 1 |   | 2 |   | 2 |   |
| 21 | 8 |   |   | 4 |   |   |   |   |   | 5 | 5 |   |   |   | 5 | 5 | 5 |   |   | 5 |   |   |   |   |   | 5 |   |
|  | 8 |   |   | 4 |   |   |   |   |   | 5 | 4 |   |   |   | 5 | 5 | 5 |   |   | 5 |   |   |   |   |   | 5 |   |
|  | 4 | 4 | 3 | 2 | 2 |   | 5 | 2 |   | 5 | 2 |   | 5 |   | 5 | 5 | 5 |   |   | 5 | 3 | 5 |   | 5 |   | 3 |   |
|  | 4 | 3 | 5 | 3 | 2 |   | 5 | 2 |   | 5 | 2 |   | 5 |   | 5 | 5 | 5 |   |   | 5 | 4 | 5 |   | 5 |   | 4 |   |
|  | 2 | 5 | 3 | 2 | 4 |   | 5 | 2 |   | 5 | 2 |   | 5 |   | 3 | 5 | 5 |   |   | 2 | 3 | 5 |   | 5 |   | 2 |   |
|  | 2 | 4 | 3 | 2 | 2 |   | 5 | 2 |   | 5 | 1 |   | 5 |   | 5 | 5 | 5 |   |   | 5 | 3 | 5 |   | 5 |   | 3 |   |
|  | 1 | 4 | 2 | 2 | 2 |   | 5 | 1 |   | 5 | 1 |   | 5 |   | 4 | 5 | 5 |   |   | 3 | 3 | 5 |   | 4 |   | 2 |   |
|  | 1 | 3 | 2 | 2 | 2 |   | 3 | 1 |   | 5 | 1 |   | 5 |   | 5 | 5 | 5 |   |   | 5 | 1 | 4 |   | 5 |   | 2 |   |
|  | .5 | 3 | 3 | 2 | 2 |   | 4 | 1 |   | 5 | 1 |   | 5 |   | 3 | 3 | 5 |   |   | 2 | 3 | 2 |   | 2 |   | 2 |   |
|  | .5 | 2 | 2 | 2 | 1 |   | 3 | 1 |   | 5 | 1 |   | 5 |   | 3 | 2 | 4 |   |   | 3 | 1 | 1 |   | 3 |   | 2 |   |
| 22 | 8 |   |   | 5 |   |   |   |   |   | 5 | 5 |   |   |   | 5 | 5 | 5 |   |   | 5 |   |   |   |   |   | 5 |   |
|  | 4 | 4 | 5 | 4 | 3 |   | 5 | 3 |   | 5 | 3 |   | 5 |   | 4 | 5 | 5 |   |   | 4 | 4 | 5 |   | 5 |   | 5 |   |
|  | 2 | 4 | 4 | 4 | 4 |   | 5 | 3 |   | 5 | 3 |   | 5 |   | 3 | 5 | 5 |   |   | 3 | 3 | 5 |   | 5 |   | 5 |   |
|  | 1 | 5 | 4 | 4 | 3 |   | 5 | 3 |   | 5 | 3 |   | 5 |   | 2 | 5 | 5 |   |   | 3 | 2 | 3 |   | 5 |   | 4 |   |
|  | .5 | 4 | 4 | 3 | 2 |   | 5 | 2 |   | 5 | 2 |   | 5 |   | 2 | 5 | 5 |   |   | 2 | 2 | 3 |   | 4 |   | 2 |   |
|  | .5 | 2 | 3 | 3 | 3 |   | 5 | 3 |   | 5 | 3 |   | 5 |   | 4 | 5 | 5 |   |   | 4 | 3 | 4 |   | 5 |   | 2 |   |
|  | .25 | 3 | 2 | 3 | 2 |   | 4 | 3 |   | 5 | 1 |   | 5 |   | 3 | 4 | 5 |   |   | 4 | 2 | 3 |   | 5 |   | 2 |   |
|  | .125 | 2 | 2 | 3 | 2 |   | 3 | 2 |   | 1 | 1 |   | 5 |   | 2 | 4 | 3 |   |   | 2 | 1 | 2 |   | 4 |   | 1 |   |
|  | .0625 | 1 | 1 | 2 | 2 |   | 2 | 2 |   | 1 | 1 |   | 3 |   | 1 | 3 | 2 |   |   | 1 | 1 | 1 |   | 1 |   | 1 |   |
| 23 | 8 |   |   | 4 |   |   |   |   |   | 5 | 3 |   |   |   | 5 | 5 | 5 |   |   | 5 |   |   |   |   |   | 4 |   |
|  | 4 | 2 | 4 | 3 | 2 |   | 5 | 2 |   | 5 | 2 |   | 5 |   | 2 | 4 | 4 |   |   | 2 | 2 | 2 |   | 4 |   | 3 |   |
|  | 2 | 1 | 2 | 2 | 1 |   | 4 | 1 |   | 4 | 1 |   | 5 |   | 2 | 4 | 3 |   |   | 1 | 1 | 2 |   | 3 |   | 2 |   |
|  | 1 | 1 | 2 | 1 | 1 |   | 3 | 1 |   | 3 | 1 |   | 5 |   | 3 | 3 | 3 |   |   | 1 | 1 | 2 |   | 3 |   | 2 |   |

TABLE XV-continued

| EX. NO. | Rate lbs/A | A | B | C | D | E | F | G | H | I | J | K | L | M | N | O | P | Q | R | S | T | U | V | W | X | Y | Z | a |
|---------|-----------|---|---|---|---|---|---|---|---|---|---|---|---|---|---|---|---|---|---|---|---|---|---|---|---|---|---|---|
| | | | | | | | | | | | | Post-emergence | | | | | | | | | | | | | | | | |
| 24 | .5 | 1 | 2 | 1 | 1 | | 3 | 1 | | 1 | 1 | | 3 | | 1 | 3 | 2 | | | 1 | | 1 | | 1 | 2 | | 1 | |
| | 8 | | | | | | | | | 5 | | | 5 | | 5 | 5 | 5 | | | 5 | | 5 | | 5 | | | 5 | 5 |
| | 4 | | | | | | | | | 5 | | | 3 | | 4 | 5 | 5 | | | 4 | | 5 | | 5 | | | 4 | 5 |
| | 2 | | | | | | | | | 5 | | | 2 | | 4 | 5 | 4 | | | 4 | | 2 | | 4 | | | 4 | 5 |
| | 1 | | | | | | | | | 5 | | | 2 | | 3 | 5 | 3 | | | 2 | | 3 | | 3 | | | 2 | 5 |
| | 1 | | | | | | | | | 5 | | | 1 | | 2 | 5 | 5 | | | 2 | | 2 | | 1 | | | 2 | 4 |
| | .5 | | | | | | | | | 3 | | | 1 | | 1 | 5 | 5 | | | 1 | | 3 | | 1 | | | 2 | 4 |
| | .25 | | | | | | | | | 2 | | | 1 | | 1 | 3 | 3 | | | 1 | | 1 | | 1 | | | 1 | 2 |
| 25 | 8 | | | | | | | | | 5 | | | 4 | | 5 | 5 | 5 | | | 5 | | 5 | | 5 | | | 5 | 5 |
| | 4 | | | | | | | | | 5 | | | 4 | | 5 | 5 | 5 | | | 5 | | 5 | | 5 | | | 4 | 5 |
| | 2 | | | | | | | | | 5 | | | 2 | | 5 | 5 | 5 | | | 5 | | 5 | | 5 | | | 4 | 5 |
| | 1 | | | | | | | | | 5 | | | 4 | | 4 | 5 | 4 | | | 4 | | 3 | | 4 | | | 3 | 5 |
| | 1 | | | | | | | | | 5 | | | 1 | | 5 | 5 | 5 | | | 5 | | 5 | | 5 | | | 2 | 5 |
| | .5 | | | | | | | | | 5 | | | 2 | | | 5 | 4 | | | 5 | | | | 5 | | | 3 | 5 |
| | .25 | | | | | | | | | 4 | | | 2 | | 1 | 5 | 1 | | | 3 | | 2 | | 4 | | | 1 | 4 |
| 26 | 8 | | | | | | | | | 5 | | | 5 | | 5 | 5 | 5 | | | 5 | | 5 | | 5 | | | 4 | 5 |
| | 4 | | | | | | | | | 5 | | | 3 | | 5 | 5 | 5 | | | 5 | | 5 | | 5 | | | 5 | 5 |
| | 2 | | | | | | | | | 5 | | | 2 | | 5 | 5 | 4 | | | 5 | | 5 | | 5 | | | 4 | 5 |
| | 1 | | | | | | | | | 5 | | | 3 | | 2 | 5 | 3 | | | 5 | | 4 | | 5 | | | 2 | 5 |
| | 1 | | | | | | | | | 5 | | | 1 | | 5 | 5 | 4 | | | 5 | | 5 | | 5 | | | 3 | 5 |
| | .5 | | | | | | | | | 5 | | | 2 | | 3 | 5 | | | | 2 | | 2 | | 4 | | | 2 | 5 |
| | .25 | | | | | | | | | 4 | | | 1 | | 1 | 4 | 2 | | | 2 | | 2 | | 2 | | | 1 | 3 |
| 27 | 8 | | | | | | | | | 5 | | | 5 | | 5 | 5 | 5 | | | 5 | | 5 | | 5 | | | 5 | 5 |
| | 8 | | | | | | | | | 5 | | | 5 | | 4 | 5 | 5 | | | 4 | | 3 | | 4 | | | 2 | 5 |
| | 8 | | | | | | | | | 5 | | | 4 | | 5 | 5 | 5 | | | 5 | | 5 | | 5 | | | 5 | 5 |
| | 4 | | | | | | | | | 5 | | | 3 | | 4 | 5 | 4 | | | 5 | | 5 | | 5 | | | 5 | 5 |
| | 4 | | | | | | | | | 5 | | | 3 | | 4 | 5 | 4 | | | 5 | | 2 | | 5 | | | 3 | 5 |
| | 2 | | | | | | | | | 5 | | | 2 | | 5 | 5 | 3 | | | 5 | | 5 | | 3 | | | 5 | 5 |
| | 2 | | | | | | | | | 4 | | | 4 | | 2 | 5 | 4 | | | 4 | | 2 | | 3 | | | 3 | 5 |
| | 1 | | | | | | | | | 5 | | | 2 | | 2 | 5 | 1 | | | 5 | | 5 | | 5 | | | 4 | 5 |
| | 1 | | | | | | | | | 5 | | | 3 | | 1 | 5 | 3 | | | 3 | | 2 | | 3 | | | 2 | 3 |
| | 1 | | | | | | | | | 5 | | | 2 | | 4 | 5 | 4 | | | 5 | | 4 | | 3 | | | 4 | 5 |
| | .5 | | | | | | | | | 3 | | | 2 | | 3 | 5 | 2 | | | 4 | | 4 | | 3 | | | 3 | 3 |
| | .25 | | | | | | | | | 2 | | | 1 | | 1 | 4 | 1 | | | 3 | | 4 | | 1 | | | 2 | 4 |
| 28 | 8 | | | | | | | | | 5 | | | 4 | | 4 | 5 | 5 | | | 4 | | 4 | | 5 | | | 5 | 5 |
| | 4 | | | | | | | | | 5 | | | 2 | | 4 | 5 | 5 | | | 5 | | 2 | | 5 | | | 4 | 5 |
| | 2 | | | | | | | | | 5 | | | 2 | | 4 | 5 | 5 | | | 5 | | 2 | | 3 | | | 3 | 5 |
| | 1 | | | | | | | | | 5 | | | 1 | | 3 | 5 | 4 | | | 5 | | 2 | | 3 | | | 2 | 5 |
| | 1 | | | | | | | | | 4 | | | 4 | | 2 | 5 | 4 | | | 5 | | 2 | | 4 | | | 3 | 5 |
| | .5 | | | | | | | | | 3 | | | 2 | | 1 | 5 | 4 | | | 4 | | 2 | | 3 | | | 2 | 5 |
| | .25 | | | | | | | | | 3 | | | 1 | | 1 | 5 | 1 | | | 4 | | 1 | | 2 | | | 2 | 2 |
| 29 | 8 | | | | | | | | | 4 | | | 4 | | 5 | 5 | 5 | | | 5 | | 5 | | 5 | | | 5 | 5 |
| | 8 | | | 4 | | | | | | 5 | 3 | | | | 5 | 5 | 5 | | | 5 | | | | | | | 4 | |
| | 4 | | | | | | | | | 5 | | | 4 | | 4 | 5 | 5 | | | 4 | | 2 | | 4 | | | 4 | 5 |
| | 2 | | | | | | | | | 1 | | | 4 | | 1 | 5 | 4 | | | 2 | | 2 | | 4 | | | 3 | 5 |
| | 1 | | | | | | | | | 4 | | | 2 | | 2 | 5 | 4 | | | 2 | | 2 | | 3 | | | 2 | 5 |
| 30 | 8 | | | | | | | | | 5 | | | 4 | | 5 | 5 | 5 | | | 5 | | 3 | | 5 | | | 5 | 5 |
| | 4 | | | | | | | | | 5 | | | 4 | | 5 | 5 | 5 | | | 4 | | 2 | | 3 | | | 3 | 5 |
| | 2 | | | | | | | | | 5 | | | 3 | | 3 | 5 | 4 | | | 2 | | 2 | | 5 | | | 3 | 5 |
| | 1 | | | | | | | | | 5 | | | 3 | | 2 | 5 | 4 | | | 3 | | 1 | | 3 | | | 3 | 4 |
| 32 | 8 | | | | | | | | | 5 | | | 5 | | 5 | 5 | 5 | | | 5 | | 5 | | 5 | | | 5 | 5 |
| | 4 | | | | | | | | | 5 | | | 4 | | 5 | 5 | 5 | | | 5 | | 5 | | 5 | | | 4 | 5 |
| | 2 | | | | | | | | | 5 | | | 3 | | 3 | 5 | 4 | | | 2 | | 1 | | 4 | | | 4 | 4 |
| | 1 | | | | | | | | | 5 | | | 3 | | 2 | 5 | 3 | | | 2 | | 2 | | 5 | | | 3 | 5 |
| 34 | 8 | | | | | | | | | 5 | | | 2 | | 4 | 5 | 5 | | | 2 | | 4 | | 5 | | | 4 | 5 |
| | 4 | | | | | | | | | 5 | | | 3 | | 2 | 5 | 4 | | | 3 | | 2 | | 4 | | | 3 | 5 |
| | 2 | | | | | | | | | 5 | | | 2 | | 1 | 5 | 3 | | | 4 | | 2 | | 2 | | | 3 | 5 |
| | 1 | | | | | | | | | 4 | | | 2 | | 1 | 5 | 3 | | | 3 | | 2 | | 2 | | | 1 | 3 |
| 36 | 8 | | | | | | | | | 5 | | | 4 | | 5 | 5 | 5 | | | 5 | | 5 | | 5 | | | 5 | 5 |
| | 4 | | | | | | | | | 5 | | | 4 | | 5 | 5 | 4 | | | 5 | | 4 | | 5 | | | 4 | 5 |
| | 2 | | | | | | | | | 5 | | | 5 | | 3 | 5 | 3 | | | 5 | | 3 | | 5 | | | 4 | 5 |
| | 1 | | | | | | | | | 5 | | | 4 | | 3 | 5 | 3 | | | 5 | | 2 | | 3 | | | 3 | 4 |
| 38 | 8 | | | 2 | | | | | | 3 | 2 | | | | 2 | 2 | 3 | | | 2 | | | | | | | 3 | |
| | 8 | | | 2 | | | | | | 3 | 2 | | | | 2 | 2 | 3 | | | 2 | | | | | | | 3 | |
| 39 | 8 | | | 2 | | | | | | 3 | 1 | | | | 3 | 4 | 2 | | | 1 | | | | | | | 2 | |
| 41 | 8 | | | 5 | | | | | | 5 | 3 | | | | | 5 | 4 | | | 3 | | | | | | | 3 | |
| | 4 | 3 | 3 | 3 | 3 | | 4 | 2 | | 5 | 3 | | 5 | | 5 | 5 | 5 | | | 2 | | 2 | | 4 | 5 | | 2 | |
| | 2 | 4 | 2 | 3 | 3 | | 4 | 2 | | 5 | 2 | | 5 | | 5 | 5 | 5 | | | 4 | | 2 | | 2 | 5 | | 2 | |
| | 1 | | 2 | 2 | 2 | | 4 | 1 | | 5 | 2 | | 5 | | 3 | 5 | 3 | | | 2 | | 2 | | 2 | 3 | | 2 | |
| | .5 | 3 | 2 | 2 | 1 | | 4 | 1 | | 3 | 1 | | 5 | | 2 | 5 | 3 | | | 1 | | 2 | | 1 | 3 | | 3 | |
| 43 | 8 | | | 2 | | | | | | 1 | 1 | | | | 1 | 1 | 1 | | | 1 | | | | | | | 1 | |
| 44 | 8 | | | 2 | | | | | | 2 | 1 | | | | 2 | 4 | 3 | | | 2 | | | | | | | 3 | |
| 45 | 8 | | | 2 | | | | | | 2 | 1 | | | | 1 | 4 | 1 | | | 1 | | | | | | | 2 | |
| 48 | 8 | | | 5 | | | | | | 5 | 5 | | | | 5 | 5 | 5 | | | 5 | | | | | | | 5 | |
| | 4 | 5 | 4 | 4 | 3 | | 5 | 3 | | 5 | 3 | | 5 | | 5 | 5 | 5 | | | 5 | | 4 | | 5 | | | 5 | |
| | 2 | 5 | 3 | 3 | 3 | | 5 | 3 | | 5 | 3 | | 5 | | 5 | 5 | 5 | | | 5 | | 3 | | 5 | | | 4 | |
| | 1 | 5 | 3 | 3 | 2 | | 5 | 2 | | 5 | 2 | | 5 | | 5 | 5 | 5 | | | 4 | | 2 | | 5 | | | 3 | |
| | .5 | 4 | 3 | 3 | 2 | | 5 | 1 | | 5 | 1 | | 5 | | 3 | 5 | 4 | | | 2 | | 2 | | 3 | | | 2 | |

TABLE XV-continued

| EX. NO. | Rate lbs/A | A | B | C | D | E | F | G | H | I | J | K | L | M | N | O | P | Q | R | S | T | U | V | W | X | Y | Z | a |
|---|---|---|---|---|---|---|---|---|---|---|---|---|---|---|---|---|---|---|---|---|---|---|---|---|---|---|---|---|
| 49 | 8 | | | 4 | | | | | | 5 | 4 | | 5 | 5 | 5 | | | | | 5 | | | | | | | 4 | |
|  | 4 | 5 | 4 | 3 | 3 | | 5 | 4 | | 5 | 3 | 5 | 5 | 5 | 5 | | | | | 5 | 4 | | 5 | 5 | | | 4 | |
|  | 2 | | 3 | 3 | 3 | | 5 | 4 | | 5 | 3 | 5 | 4 | 5 | 5 | | | | | 5 | 4 | | 5 | 5 | | | 3 | |
|  | 1 | | 3 | 3 | 4 | | 4 | 4 | | 5 | 3 | 5 | 4 | 5 | 5 | | | | | 4 | 3 | | 4 | 5 | | | 3 | |
|  | .5 | | 2 | 2 | 2 | | 3 | 2 | | 5 | 1 | 5 | 2 | 5 | 4 | | | | | 5 | 2 | | 3 | 4 | | | 2 | |
| 50 | 8 | | | 4 | | | | | | 5 | 4 | | 5 | 5 | 5 | | | | | 5 | | | | | | | 5 | |
|  | 4 | 4 | 3 | 3 | 3 | | 4 | 4 | | 5 | 3 | 5 | 5 | 5 | 5 | | | | | 5 | 5 | | 4 | 5 | | | 3 | |
|  | 2 | 4 | 3 | 2 | 2 | | 5 | 3 | | 5 | 3 | 5 | 5 | 5 | 5 | | | | | 3 | 4 | | 3 | 5 | | | 3 | |
|  | 1 | 5 | 2 | 2 | 2 | | 3 | 2 | | 5 | 2 | 5 | 3 | 5 | 4 | | | | | 4 | 2 | | 2 | 5 | | | 2 | |
|  | .5 | 4 | 1 | 2 | 1 | | 2 | 2 | | 3 | 1 | 4 | 1 | 3 | 3 | | | | | 2 | 1 | | 1 | 2 | | | 2 | |
| 54 | 8 | | | 3 | | | | | | 5 | 4 | | 5 | 5 | 5 | | | | | 5 | | | | | | | 4 | |
|  | 4 | 5 | 3 | 3 | 4 | | 4 | 3 | | 5 | 4 | 5 | 5 | 5 | 5 | | | | | 5 | 2 | | 4 | 5 | | | 3 | |
|  | 2 | 4 | 3 | 3 | 3 | | 5 | 3 | | 5 | 3 | 5 | 5 | 5 | 5 | | | | | 4 | 2 | | 4 | 5 | | | 2 | |
|  | 1 | | 2 | 3 | 3 | | 5 | 3 | | 5 | 3 | 5 | 4 | 5 | 5 | | | | | 4 | 3 | | 2 | 3 | | | 2 | |
|  | .5 | 4 | 2 | 2 | 2 | | 3 | 2 | | 2 | 2 | 4 | 3 | 5 | 5 | | | | | 3 | 2 | | 2 | 3 | | | 2 | |

As the foregoing illustrates, the compounds of the present invention exhibit herbicidal activity at rates of from 0.05 to 8 lbs/acre. Therefore, in another embodiment, the present invention is directed to a method for inhibiting the growth of a plant which comprises applying to the plant an effective amount of a compound of the present invention. The compounds can be applied pre-emergently for the comtrol of germinating seeds or post-emergently for the control of existing vegetation. The compounds are preferably formulated as described below.

Other Utilities

Compounds of the present invention have exhibited nematocidal, fungicidal, anthelmintic, and ectoparasiticidal activity. By appropriate selection of rates and methods of application, therefore, the present compounds can be employed for these other utilities. For all of these uses, the compounds are employed in conventional manners.

Nematocidal Activity

The compound of Example 36 was expressly evaluated for the control of various nematode species. The compound was dissolved in 50:50 acetone:ethanol and diluted with water to create solutions of varying compound concentration. A 10 ml. aliquot of each solution was mixed well with one kilogram of moist nematode-infested soil, and the soil was then placed in pots and planted with crop seeds. The pots were held for a number of weeks, then the soil and roots were evaluated for the control of the nematode species. The crop was also evaluated for various effects of nematode damage.

In a first trial, the crop seeds were 'Davis' soybean, the soil which was used was natural field soil heavily infested with two nematode species:
  root-knot nematode (*Meloidogyne incognita*)
  Race 3, cyst nematode (*Heterodera glycines*)
and also infested with three other nematode species:
  stubby root nematode (*Paratrichodorus christiei*)
  sprial nematode (*Helicotylenchus dihystera*)
  lesion nematode (*Pratylenchus brachyurus*)
and the plants were allowed to develop for 9 weeks prior to evaluating the nematode control and effect on crop.

In the second trial, the crop seeds were 'Rowden' cotton, the soil which was used was natural field soil infested with the following nematode species:
  lesion nematode (*Pratylenchus brachyurus*)
  stubby root nematode (*Paratrichldorus christiei*)
  spiral nematode (*Helicotylenchus dihystera*)
  lance nematode (*Hoplolaimus galeatus*)
and the plants were allowed to develop for 7 weeks prior to evaluating the nematode control and effect on crop.

In both tests, counts were also made of saprophagous nematodes.

Phenamiphos was employed as a reference standard in both trials. There were eight pots (replications) per treatment.

Results were as set forth in the following four tables.

TABLE XVI

| Treatment | Concentration Micrograms/ml | Nematode/Soybean Trial/Nematode Ratings | | | | | | | Lesion Nematodes From Roots |
|---|---|---|---|---|---|---|---|---|---|
| | | Number of Root Knot Nematodes | | Number of Stubby Root Nematodes In 100 cc Soil | Number of Spiral Nematodes | | Number of Saprophagous Nematodes | | |
| | | In 100 cc Soil | From Roots | | In 100 cc Soil | From Roots | In 100 cc Soil | From Roots | |
| Example 36 | 1000 | 0 | 349 | 0 | 0 | 0 | 241 | 118 | 0 |
|  | 500 | 1 | 98 | 0 | 0 | 1 | 174 | 143 | 5 |
|  | 100 | 117 | 104 | 1 | 0 | 10 | 177 | 115 | 5 |
|  | 50 | 87 | 213 | 14 | 6 | 25 | 180 | 199 | 35 |
|  | 25 | 69 | 72 | 17 | 25 | 83 | 182 | 214 | 20 |
|  | 0, 0 Controls | 62 | 134 | 53 | 31 | 129 | 216 | 245 | 20 |
| Phenamiphos | 1000 | 0 | 3 | 1 | 0 | 1 | 125 | 90 | 0 |
|  | 500 | 0 | 41 | 1 | 1 | 26 | 125 | 142 | 1 |
|  | 100 | 4 | 81 | 18 | 8 | 57 | 91 | 147 | 6 |
|  | 50 | 13 | 26 | 73 | 14 | 103 | 161 | 304 | 25 |
|  | 25 | 37 | 25 | 22 | 15 | 119 | 194 | 200 | 15 |

TABLE XVI-continued

| | | Nematode/Soybean Trial/Nematode Ratings | | | | | | | |
|---|---|---|---|---|---|---|---|---|---|
| | | Number of Root Knot Nematodes | | Number of Stubby Root Nematodes | Number of Spiral Nematodes | | Number of Saprophagous Nematodes | | Lesion Nematodes |
| Treatment | Concentration Micrograms/ml | In 100 cc Soil | From Roots | In 100 cc Soil | In 100 cc Soil | From Roots | In 100 cc Soil | From Roots | From Roots |
| | 0 } Controls 0 | 26 | 30 | 53 | 35 | 252 | 222 | 249 | 37 |

TABLE XVII

| | | Nematode/Soybean Trial/Crop Ratings | | | | | | |
|---|---|---|---|---|---|---|---|---|
| Treatment | Concentration Micrograms/ml | Top Height (cm) | Top Weight (gms) | Root Weight (gms) | Root Condition (1-5, 1 = Best, 5 = Worst) | Gall Number | Gall Rate (0-10, 0 = No Galls, 10 = Worst) | Cyst Number |
| Example 36 | 1000 | 22.3 | 4.45 | 7.08 | 2.0 | 40 | 4.0 | 5 |
| | 500 | 22.3 | 6.11 | 10.10 | 2.8 | 39 | 4.3 | 1 |
| | 100 | 17.1 | 2.58 | 3.90 | 4.1 | 57 | 6.3 | 1 |
| | 50 | 19.1 | 1.95 | 3.21 | 3.8 | 70 | 6.5 | 0 |
| | 25 | 19.5 | 2.45 | 3.34 | 4.5 | 64 | 7.0 | 0 |
| | 0 } Controls 0 | 19.1 | 2.06 | 3.06 | 4.8 | 70 | 6.6 | 0 |
| Phenamiphos | 1000 | 37.3 | 11.03 | 7.36 | 3.6 | 10 | 1.0 | 0 |
| | 500 | 46.7 | 7.01 | 3.69 | 3.6 | 9 | 1.0 | 1 |
| | 100 | 39.9 | 4.32 | 3.08 | 3.6 | 41 | 4.0 | 0 |
| | 50 | 34.7 | 3.22 | 2.30 | 3.7 | 41 | 4.7 | 1 |
| | 25 | 28.7 | 2.24 | 1.85 | 4.5 | 42 | 6.6 | 0 |
| | 0 } Controls 0 | 23.2 | 2.72 | 3.35 | 4.2 | 55 | 5.8 | 0 |

TABLE XVIII

| | Nematode/Cotton Trial/Nematode Ratings | | | | | | | | | |
|---|---|---|---|---|---|---|---|---|---|---|
| | Number of Lesion Nematodes | | Number of Stubby Root Nematodes In 100 cc Soil | Number of Spiral Nematodes | | Number of Lance Nematodes | | Number of Dorylaimoid Nematodes In 100 cc Soil | Number of Saprophagous Nematodes | |
| Treatment, Concentration Micrograms/ml | In 100 cc Soil | From Roots | | In 100 cc Soil | From Roots | In 100 cc Soil | From Roots | | In 100 cc Soil | From Roots |
| Example 36: | | | | | | | | | | |
| 1000 | 0 | 1 | 0 | 0 | 1 | 5 | — | 8 | 122 | 48 |
| 500 | 4 | 32 | 28 | 8 | 2 | 16 | 26 | 7 | 142 | 83 |
| 100 | 24 | 260 | 91 | 9 | 9 | 34 | 61 | 4 | 189 | 89 |
| 50 | 29 | 239 | 64 | 6 | 7 | 6 | 25 | 7 | 123 | 91 |
| 25 | 38 | 321 | 69 | 10 | 4 | 15 | 20 | 16 | 141 | 124 |
| 0 } Controls 0 | 12 | 261 | 96 | 5 | 21 | 15 | 39 | 12 | 160 | 100 |
| Phenamiphos: | | | | | | | | | | |
| 1000 | 0 | 4 | 12 | 2 | 5 | 3 | 6 | 3 | 71 | 25 |
| 500 | 0 | 16 | 27 | 7 | 68 | 9 | 20 | 3 | 66 | 52 |
| 100 | 4 | 61 | 55 | 16 | 202 | 23 | 33 | 3 | 133 | 148 |
| 50 | 13 | 101 | 41 | 13 | 226 | 20 | 48 | 6 | 121 | 170 |
| 25 | 19 | 181 | 65 | 17 | 217 | 33 | 57 | 9 | 137 | 204 |
| 0 } Controls 0 | 24 | 103 | 42 | 39 | 411 | 44 | 46 | 18 | 140 | 282 |

TABLE XIX

| | | Nematode/Cotton Trial/Crop Ratings | | | | | |
|---|---|---|---|---|---|---|---|
| Treatment | Concentration Micrograms/ml | Top Height (cm) | Top Weight (gms) | Root Weight (gms) | Root Condition (1-5, 1 = Best, 5 = Worst) | Gall Rate (0-10, 0 = No Galls, 10 = Worst) | Gall Number |
| Example 36 | 1000 | 10.7 | 1.33 | 0.91 | 3.5 | 0 | 0 |
| | 500 | 10.9 | 1.22 | 0.75 | 3.9 | 0 | 0 |
| | 100 | 11.6 | 1.27 | 0.76 | 3.3 | 0 | 0 |
| | 50 | 11.4 | 1.24 | 0.63 | 4.2 | 0 | 0 |
| | 25 | 11.3 | 1.26 | 0.78 | 4.0 | 0 | 0 |

TABLE XIX-continued

| Treatment | Concentration Micrograms/ml | | Top Height (cm) | Top Weight (gms) | Root Weight (gms) | Root Condition (1-5, 1 = Best, 5 = Worst) | Gall Rate (0-10, 0 = No Galls, 10 = Worst) | Gall Number |
|---|---|---|---|---|---|---|---|---|
| | 0 | Controls | 10.6 | 1.12 | 0.55 | 4.5 | 0 | 0 |
| | 0 | | | | | | | |
| Phenamiphos | 1000 | | 12.8 | 1.45 | 0.85 | 3.2 | 0 | 0 |
| | 500 | | 14.8 | 1.76 | 0.98 | 3.3 | 0 | 1 |
| | 100 | | 14.8 | 1.72 | 0.75 | 3.7 | 0 | 0 |
| | 50 | | 14.6 | 1.71 | 0.77 | 3.8 | 0 | 0 |
| | 25 | | 14.6 | 1.60 | 0.71 | 3.9 | 0 | 1 |
| | 0 | Controls | 12.8 | 1.41 | 0.69 | 4.0 | 0 | 0 |
| | 0 | | | | | | | |

Fungicidal Activity

Various of the compounds to be employed in accordance with the present invention were evaluated for the control of fungal and other plant pathogens. Each compound was formulated by dissolving it in a 1:1 mixture of acetone/ethanol with the aid of Tween 20 (an emulsifier sold by ICI Americas Inc.) and thereafter diluting the solution with water. The initial test concentration was 400 ppm; for some of the compounds, additional formulations were prepared containing lower concentrations of compound. A portion of the resulting formulation was sprayed onto the foliage of suitable plants, or onto a half of a grape in the case of Botrytis. The foliage or grape was subsequently infested with the pathogen, incubated where appropriate, and held for a period to permit expression of disease symptoms.

Activity against the pathogen was rated as follows:
1=0-19% disease control
2=20-29% disease control
3=30-39% disease control
4=40-59% disease control
5=60-74% disease control
6=75-89% disease control
7=90-96% disease control
8=97-99% disease control
9=100% disease control
0=no evaluation possible (too much injury)

Injury to plants was rated on a scale of 1-5, with 1=no injury and 5=death. However, this rating was recorded only when it was 2 or higher. The type of injury was additionally recorded in most ratings:
B=burning
C=chlorosis
G=general necrosis
S=stunting The results are set forth in the following tables. Abbreviations have the following meanings:
Powd Mdew=Powdery Mildew
Rice Blst=Rice Blast
Leaf Rust=Leaf Rust
Botr Ytis=Botrytis
Appl Scab=Apple Scab
Dwny Mdew=Downy Mildew
Sept Oria=Septoria
Cerc Beet=Cercospora on Beet

TABLE XX

| Ex. No. | ppm | Powd Mdew | Rice Blst | Leaf Rust | Botr Ytis | Dwny Mdew | Appl Scab | Sept Oria | Cerc Beet |
|---|---|---|---|---|---|---|---|---|---|
| 1 | 400.00 | 1(4G) | 0(4G) | 0(4G) | 8 | 0(5) | | | |
| | 400.00 | | | | 1 | | | | |
| | 100.00 | | | | 1 | | 0(4G) | 0(3G) | |
| | 25.00 | | | | 1 | | | | |
| 4 | 400.00 | 0(4G) | 0(4G) | 0(4G) | 9 | 0(5) | | | |
| | 400.00 | | | | 9 | | | | |
| | 100.00 | | | | 5 | | 0(5) | 0(3G) | 0(5) |
| | 25.00 | | | | 1 | | | | |
| 5 | 400.00 | 5(2G) | 0(3G) | 0(3G) | 1 | 8(3G) | | | |
| | 400.00 | | | | | 0(5) | | | |
| | 100.00 | | | | | 0(4G) | 5 | 5 | 5(2G) |
| | 25.00 | | | | | 1 | | | |
| 6 | 400.00 | 1(3G) | 0(5) | 0(4G) | 1 | 0(5) | | | |
| 7 | 400.00 | 1 | 1 | 1(2G) | 1 | 0(5) | | | |
| 9 | 400.00 | 1 | 1 | 1 | 1 | 1 | | | |
| 10 | 400.00 | 1 | 1 | 3(2G) | 1 | 1 | | | |
| 11 | 400.00 | 1 | 1 | 1 | 1 | 1 | | | |
| 13 | 400.00 | 0(4G) | 0(5) | 0(4G) | 9 | 0(5) | | | |
| | 100.00 | 1(3G) | 0(4G) | 0(3G) | 8 | 0(5) | 0(5) | 0(3G) | |
| | 100.00 | | | 0(4G) | 1 | | | | |
| | 25.00 | | | 9(3G) | 1 | | | | |
| | 25.00 | | | 7(2G) | 1 | | | | |
| | 6.25 | | | 3 | 1 | | | | |
| | 1.56 | | | 2 | 1 | | | | |
| | 400.00 | 0(5) | 0(5) | 0(4G) | 8 | 0(5) | | | |
| | 25.00 | 1(2G) | 0(4G) | 8(2G) | 1 | 0(5) | | | |
| | 6.25 | | | 8(2G) | 1 | | | | |
| 14 | 400.00 | 1 | 1 | 1 | 1 | 1 | | | |
| 15 | 400.00 | 1 | 1 | 1(2G) | 1 | 1(3G) | | | |

TABLE XX-continued

| | | Foliar Applications | | | | | | | |
|---|---|---|---|---|---|---|---|---|---|
| Ex. No. | ppm | Powd Mdew | Rice Blst | Leaf Rust | Botr Ytis | Dwny Mdew | Appl Scab | Sept Oria | Cerc Beet |
| 16 | 400.00 | 0(4G) | 0(4G) | 0(4G) | 9 | 0(5) | | | |
| | 400.00 | | | | 8 | | | | |
| | 100.00 | | | | 1 | | 0(4G) | 0(3G) | 0(4G) |
| | 25.00 | | | | 1 | | | | |
| 17 | 400.00 | 0(4G) | 0(4G) | 0(4G) | 9 | 0(5) | | | |
| | 400.00 | | | | 9 | | | | |
| | 100.00 | | | | 1 | | 0(4G) | 0(3G) | 0(5) |
| | 25.00 | | | | 1 | | | | |
| 18 | 400.00 | 3(2G) | 0(3G) | 7(3G) | 1 | 0(5) | | | |
| | 400.00 | | | 7(3G) | | | | | |
| | 100.00 | | | 1 | | | 1 | 1 | 1 |
| | 25.00 | | | 1 | | | | | |
| 19 | 400.00 | 5(2G) | 0(3G) | 0(3G) | 1 | 0(5) | | | |
| 20 | 400.00 | 1 | 1 | 1 | 1 | 0(5) | | | |
| 21 | 400.00 | 7(4G) | | 0(4G) | 7 | 0(5) | | | |
| | 100.00 | 6(3G) | | 0(3G) | 1 | 0(5) | 3 | 0(3G) | 0(4G) |
| | 100.00 | | | 0(4G) | | | | | |
| | 25.00 | | | 0(3G) | | | | | |
| | 6.25 | | | 2(2G) | | | | | |
| | 400.00 | | | | 1 | | | | |
| | 100.00 | | | | 1 | | 0(3G) | 0(3G) | 0(5) |
| | 25.00 | | | | 1 | | | | |
| | 400.00 | 8(3G) | 1 | 0(4G) | 9 | 0(5) | | | |
| | 25.00 | 4(2C) | | 7(2G) | 1 | 0(5) | | | |
| | 400.00 | 0(4G) | 0(5) | 0(4G) | 9 | 0(5) | | | |
| 23 | 400.00 | 1 | 1 | 1(2S) | 1 | 0(5) | | | |
| 25 | 400.00 | 0(3G) | 0(5) | 0(3G) | 3 | 0(5) | | | |
| 26 | 400.00 | 6(3G) | 0(5) | 0(4G) | 1 | 0(5) | | | |
| | 100.00 | 4(3G) | 0(4G) | 0(3G) | 1 | 0(5) | 0(4G) | 0(4G) | |
| | 100.00 | | | 8(3G) | | | | | |
| | 25.00 | | | 6(2G) | | | | | |
| | 6.25 | | | 2 | | | | | |
| | 400.00 | 0(3G) | 0(3G) | 0(3G) | 9 | 0(5) | | | |
| | 25.00 | 2(2G) | 0(4G) | 8(3G) | 1 | 0(5) | | | |
| 27 | 400.00 | 0(3G) | 0(5) | 0(4G) | | 0(5) | | | |
| | 100.00 | 2(2G) | 0(3G) | 0(3G) | | 0(5) | 1(3G) | 0(3G) | |
| | 25.00 | | | 7(3G) | | | | | |
| | 6.25 | | | 2(2G) | | | | | |
| | 1.56 | | | 1 | | | | | |
| | 400.00 | 8(3G) | 0(4G) | 0(4G) | 3 | 0(5) | | | |
| | 25.00 | 1 | 3(2G) | 8(3G) | | 0(5) | | | |
| 28 | 400.00 | 0(3G) | 0(3G) | 0(3G) | 1 | 0(5) | | | |
| 29 | 400.00 | 0(3G) | 0(4G) | 0(4G) | 1 | 0(5) | | | |
| 30 | 400.00 | 1(3G) | 0(4G) | 0(4G) | 9 | 0(5) | | | |
| | 25.00 | | | | 1 | | | | |
| | 400.00 | | | | 8 | | | | |
| | 100.00 | | | | 1 | | 7(2G) | 0(3G) | 0(5) |
| | 100.00 | | | | | | 5(2G) | | |
| | 25.00 | | | | | | 1 | | |
| | 6.25 | | | | | | 1 | | |
| 32 | 400.00 | 1(3G) | 0(5) | 0(4G) | 9 | 0(5) | | | |
| | 25.00 | | | | 1 | | | | |
| | 400.00 | | | | 9 | | | | |
| | 100.00 | | | | 3 | | 7(2G) | 0(3G) | 0(5) |
| | 100.00 | | | | | | 7(3G) | | |
| | 25.00 | | | | | | 2 | | |
| | 6.25 | | | | | | 1 | | |
| 34 | 400.00 | 4 | 1 | 7(3G) | 1 | 0(5) | | | |
| | 25.00 | | | 2 | | | | | |
| | 400.00 | | | 0(3G) | | | | | |
| | 100.00 | | | 8(3G) | | | | 0(3G) | |
| | 100.00 | | | 8(2G) | | | 1 | 7(3G) | 1(3G) |
| | 25.00 | | | 5(2G) | | | | 1 | |
| | 6.25 | | | 2 | | | | 1 | |
| 36 | 400.00 | 7(3G) | 0(4G) | 0(4G) | 7 | 0(5) | | | |
| | 25.00 | 1 | | | 1 | | | | |
| | 400.00 | 5(3G) | | | 8 | | | | |
| | 100.00 | 3(2G) | | | 2 | | 7(3G) | 3(2G) | 0(4G) |
| | 100.00 | | | | | | 0(3G) | | |
| | 25.00 | | | | | | 1 | | |
| | 6.25 | | | | | | 1 | | |
| 37 | 400.00 | 0(4G) | 0(5) | 0(5) | 9 | 0(5) | | | |
| | 400.00 | | | | 8 | | | | |
| | 100.00 | | | | 2 | | 0(4G) | 0(3G) | 0(5) |
| | 25.00 | | | | 1 | | | | |
| 38 | 400.00 | 3 | 0(3G) | 5(3G) | 4 | 0(5) | | | |
| 39 | 400.00 | 1 | 1 | 1 | 1 | 7(2G) | | | |
| 40 | 400.00 | 9(3G) | 0(4G) | 0(3G) | 1 | 0(5) | | | |
| | 100.00 | 8 | 0(3G) | 7(2G) | 1 | 0(5) | 7(3C) | 0(3G) | 0(5) |

TABLE XX-continued

| Ex. No. | ppm | Powd Mdew | Rice Blst | Leaf Rust | Botr Ytis | Dwny Mdew | Appl Scab | Sept Oria | Cerc Beet |
|---|---|---|---|---|---|---|---|---|---|
| | 100.00 | 7 | | 9(3G) | | | 0(3G) | | |
| | 25.00 | 6 | | 8(3G) | | | 9 | | |
| | 25.00 | 4 | | 8(2G) | | | 8(2G) | | |
| | 6.25 | 3 | | 6(2G) | | | 6 | | |
| | 1.56 | 1 | | 5 | | | 3 | | |
| | 400.00 | 9(2G) | 0(3G) | 7(3G) | 7 | 0(5) | | | |
| | 25.00 | 7 | 0(3G) | 7(2G) | 1 | 0(5) | | | |
| | 6.25 | 1 | | 6 | | | 7 | | |
| 41 | 400.00 | 0(3G) | 0(4G) | 0(3G) | 1 | 0(4G) | | | |
| 42 | 400.00 | 1 | 1 | 1 | 1 | 1 | | | |
| 43 | 400.00 | 1 | 1 | 1 | 1 | 1 | | | |
| 44 | 400.00 | 3(2G) | 0(3G) | 5(3G) | 1 | 1 | | | |
| 45 | 400.00 | 1 | 7(2G) | 5(2G) | 1 | 8(2G) | | | |
| | 400.00 | | 7 | | | 9 | | | |
| | 100.00 | | 3 | | | 2 | 1 | 1 | 1 |
| | 25.00 | | 2 | | | 1 | | | |
| 46 | 400.00 | 8 | 0(3G) | 9(2G) | | 8(2G) | | | |
| | 100.00 | 8 | 0(3G) | 9(2G) | | 8(2G) | 3 | 1 | 0(5) |
| | 100.00 | 8 | 0(3G) | 9(2G) | | 0(5) | | | |
| | 25.00 | 6 | 2(2G) | 5(2C) | | 0(4G) | | | |
| | 6.25 | 5 | 1 | 2 | | 1(2G) | | | |
| | 400.00 | 8 | 0(3G) | 7(3G) | 1 | 0(4G) | | | |
| | 25.00 | 6 | 7(2G) | 9 | | 1 | | | |
| 48 | 400.00 | 1(3G) | 0(4G) | 0(3G) | 1 | 0(5) | | | |
| 49 | 400.00 | 0(4G) | 0(5) | 0(4G) | 7 | 0(5) | | | |
| | 400.00 | | | | 1 | | | | |
| | 100.00 | | | | 1 | | 1(3G) | 0(4G) | 0(5) |
| | 25.00 | | | | 1 | | | | |
| 50 | 400.00 | 7 | 1 | 8 | 1 | 8(2G) | | | |
| | 400.00 | 1(3G) | | 0(4G) | | 0(5) | | | |
| | 100.00 | 1(2G) | | 8(3G) | | 0(4G) | 1(2G) | 0(3G) | 0(3G) |
| | 25.00 | 1 | | 2(2G) | | 1(2G) | | | |
| 51 | 400.00 | 3(3G) | 0(4G) | 0(4G) | 1 | 0(5) | | | |

Additional Fungicidal Testing

The compound of Example 46 was further evaluated for the control of various fungal pathogens. For these additional tests, the compound was formulated as described above for the general fungicidal testing. The compound was applied to foliage of a host plant, either before ("protective") or after ("curative") inoculation with the pathogen, while other applications were made as a soil drench. The host plant was wheat. Suitable reference standards, as well as a control, were used to verify each test. The results of these tests were as set forth in the following tables. Ratings were made on the same scales used in the previous table.

TABLE XXI

Wheat Powdery Mildew (*Erysiphe graminis tritici*)

| | | Disease Ratings | | | |
|---|---|---|---|---|---|
| | Rate | Foliar | | Rate | |
| Treatment | (ppm) | Protective | Curative | (lbs/acre) | Soil |
| Compound of | 400 | 7 | 5 | 10 | 1 |
| Example 46 | 200 | 7 | 3 | 5 | 1 |
| | 100 | 7 | 1 | 2.5 | 1 |
| | 50 | 6 | 1 | | |

TABLE XXII

Wheat Leaf Rust (*Puccinia recondita tritici*)

| | | Foliar | | Rate | |
|---|---|---|---|---|---|
| Treatment | Rate | Protective | Curative | (lbs/acre) | Soil |
| Compound of | 400 | 9(2G) | 1(2G) | 10 | 1 |
| Example 46 | 200 | 9(2G) | 1(2G) | 5 | 1 |
| | 100 | 9(2G) | 1(2G) | 2.5 | 1 |
| | 50 | 8 | 1 | | |

As will be apparent from the foregoing, many of the compounds of the present invention exhibit useful fungicidal activity. Accordingly, in another embodiment, the present invention is directed to a method of inhibiting a plant pathogenic fungal organism which comprises applying to a locus of the organism an inhibiting amount of a compound of the present invention. The method is practiced in accordance with standard techniques for the use of fungicides. The compounds can be formulated as described below in the Formulations section. In general, good fungicidal efficacy can be expected at rates of 0.5–5.0 lbs/acre.

Formulations

For any of their various uses, the compounds of the present invention are preferably formulated with a suitable argriculturally acceptable carrier. Typically such a formulation will contain from about 0.05 to about 95.0 percent by weight of the active ingredient. Examples of such compositions include sprayable formulations, such as wettable powders, aqueous suspensions and emulsifiable concentrates; and solid compositions, such as dusts, granules, and dry-flowable pellets. The compounds can also be formulated with fertilizer and applied to soil to achieve both a utility in accordance with the present invention as well as fertilization of the crop.

Sprayable formulations are in the form of concentrated compositions which can be diluted with water to form water dispersions or emulsions containing in the range from about 0.05 percent to about 10 percent of the active agent by weight. Such water dispersions or emulsions are sprayed onto plants or onto soil. The concentrated compositions may be either solids, usually known as wettable powders or dry flowables, or liquids, usually known as emulsifiable concentrates and aqueous suspensions.

A typical wettable powder comprises an intimate mixture of an active ingredient of the invention, an inert carrier, and surfactants. The concentration of the active agent is usually from about 25 percent to about 90 percent by weight. The inert carrier is usually chosen from among the attapulgite clays, the montmorillonite clays, the diatomaceous earths, the kaolinites, or the purified silicates. Effective surfactants, comprising from about 0.5 percent to about 10 percent by weight of the wettable powder, are chosen from among the condensed naphthalenesulfonates, the alkyl sulfates and the alkyl arylethoxylates. Suspending agents, such as the sulfonated lignins, can also be added.

A typical emulsifiable concentrate comprises from about 0.1 to about 6 pounds (from about 0.045 kg to about 3.05 kg) of a compound of the invention per gallon of liquid, dissolved in a mixture of organic solvents and emulsifiers. The organic solvent is chosen with regard to its solvency and its cost. Useful solvents include the aromatics, especially the xylenes and the heavy aromatic naphthas. Hydrophilic cosolvents such as DMF, cyclohexanone, and the glycol ethers such as 2-methoxyethanol may be included. Other organic solvents may also be used, including the terpenic solvents and kerosene; methyl heptyl ketone and other high molecular weight ketones; cyclohexyl acetate and other high molecular weight esters. Suitable emulsifiers for emulsifiable concentrates are chosen from the alkylbenzenesulfonates, naphthalenesulfonates, and nonionic surfactants such as alkylphenol adducts of polyoxyethylene, and are used at similar percentages as for wettable powders.

An aqueous suspension, or flowable, is comprised of a finely ground suspension of the active ingredient dispersed in a water based system. This type of formulation is particularly useful for compounds with low water solubility. The concentration of active agent is usually from about 15 to 60 percent by weight. A typical aqueous suspension may comprise wetting and dispersing agents, antifreeze components, thickening or bulking agents, as well as water and the active ingredient.

Dust compositions containing a compound of the present invention usually contain from about 0.1 to about 50 percent by weight of the compound. Dusts are prepared by intimately mixing and finely grinding the active agent with an inert solid such as ground montmorillonite clay, attapulgite clay, talc, ground volcanic rock, kaolin clay, or other inert, relatively dense, inexpensive substances.

Solid, granular compositions are convenient for the application of compounds of this invention to the soil and will contain the active agent in an amount from about 0.1 to about 25 percent by weight. Granules comprise a compound of the invention dispersed on a granular inert carrier such as coarsely ground clay of from about 0.1 to about 3 mm particle size. The active ingredient is most conveniently applied to the clay by dissolving it in an inexpensive solvent, such as acetone, methylene chloride, xylene or other petroleum solvents, methoxy propylene glycol, or the like, and applying the solution to the sized clay in an appropriate solids mixer. The solvent is then typically removed by evaporation; however removal is not essential. Alternatively, any of the present compounds which is an oil can be sprayed, with or without heating, directly onto clay. Likewise, any of the present compounds which is a solid can be melted and then sprayed directly onto clay.

Representative formulations of the present invention are illustrated below.

EXAMPLE A

10% Granule, Compound of Example 24

The compound of Example 24 was dissolved in acetone (in the ratio of 1 gram of compound per 4 grams of acetone). Propylene glycol was added and the mixture stirred, then poured over the carrier, mixed well, and air dried.

| Ingredient | Percent by Weight |
|---|---|
| Compound of Example 24 | 10 |
| Propylene glycol | 5 |
| Florex 24/48 RVM | 85 |
| | 100 |

*RVM = regular volatile material

EXAMPLE B

10% Granule, Compound of Example 1

The compound of Example 1 was dissolved in methylene chloride (a 12% solution), poured over the carrier, mixed well, and air dried.

| Ingredient | Percent by Weight |
|---|---|
| Compound of Example 1 | 10 |
| Florex 24/48 RVM | 90 |
| | 100 |

EXAMPLE C

10% Granule, Compound of Example 36

The compound of Example 36 was formulated in the same procedure as the immediately preceding example.

| Ingredient | Percent by Weight |
|---|---|
| Compound of Example 36 | 10 |
| Florex 24/48 RVM | 90 |
| | 100 |

EXAMPLE D

10% Granule, Compound of Example 37

The compound of Example 1 was dissolved in methylene chloride and an equimolar amount of tributylamine was slowly added to the solution to produce the salt of Example 37. The solution then containing the salt of Example 37 was poured over the carrier, mixed well, and air dried.

| Ingredient | Percent by Weight |
|---|---|
| Compound of Example 37 | 14.5 |
| Lowe's clay 30/40 mesh, Bloomfield, Missouri | 85.5 |
| | 100.0 |

EXAMPLES E–H

10% Granule, Compound of Example 36

The procedure of the preceding example was used to make four 10% granular formulations from the compound of Example 1 and dimethylbis($C_{14}$–$C_{18}$)ammonium chloride, the latter estimated to be only 75% pure, yielding formulations of the compound of Example 36. The four carriers were as follows:

Oil-Dri Mississippi Grey Clay
Oil-Dri Mississippi Brown Clay
Florex Clay LVM (low volatile material)
Lowe's Oran, Missouri Clay The composition of all four formulations was as follows.

| Ingredient | Percent by Weight |
| --- | --- |
| Compound of Example 36 | 11.9 |
| Carrier | 88.1 |
|  | 100.0 |

EXAMPLES I AND J

10% Granule, Compounds of Examples 1 and 36, Carrier Study

Various carriers were evaluated for 10% granular formulations of each of the compounds of Examples 1 and 36. Each compound was dissolved in dichloromethane, mixed, poured onto the respective carrier, mixed well, and air dried. The carriers evaluated were as follows.

Oil-Dri Mississippi Grey clay (this same clay is also referred to as Agsorb RVM-MS);
Oil-Dri Mississippi Brown clay (this same clay is also referred to as Agsorb LVM-MS);
Oil-Dri Georgia white clay—Oil Dry Corporation
Florex RVM;
Florex LVM—Floridin Company
Agsorb LVM—Oil Dry Corporation
Attapulgus RVM—Englehardt Minerals
Bentonite Granular—American Colloid
Pike's Peak clay (9-J)—General Reduction Crop.
KWK Volclay—American Colloid
Lowe's Oran, Missouri clay;
Lowe's Bloomfield, Missouri clay—Lowe's Industrial Products, Inc.

All formulations had the same composition:

| Ingredient | Percent by Weight |
| --- | --- |
| Compound of Example 1 or Example 36 | 10 |
| Carrier | 90 |
|  | 100 |

Based on the foregoing formulations, Oil-Dri Mississippi Grey clay and Oil-Dri Mississippi Brown clay are preferred carriers for the parent compounds, whereas Florex LVM clay and Lowe's Oran Missouri clay are preferred carriers for the salts.

Starting Materials

As taught above, the compounds of the present invention are prepared by the reaction of an acyl halide and an aniline, 1-aminonaphthalene, 2-amino-5-nitropyridine:

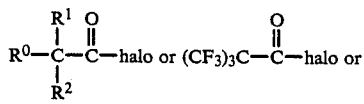

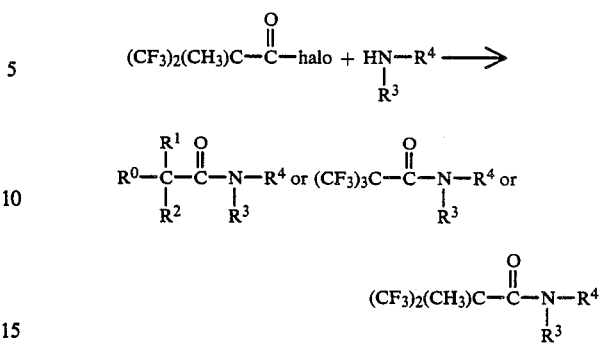

These starting materials are either known compounds or are prepared in known procedures. Essentially all of the anilines are known compounds. 1-Aminonaphthalene and 2-amino-5-nitropyridine are likewise known compounds.

Some of the alkanoyl halides are known compounds. The following are described in the literature:

$$F-\underset{\underset{Y}{|}}{\overset{\overset{CF_3}{|}}{C}}-\overset{\overset{O}{\|}}{C}-F \text{ or } -Cl$$

| Y | Reference |
| --- | --- |
| CN | A, B, C |
| $CF_3$ | D, E |
| n-$C_3F_7$ | F, G |

The following are also described in the literature:

($CF_3$)$_3$CCOF—Reference D ($CF_3$)$_2$BrCCOF—Reference H ($CF_3$)$_2$ClCCOF—Reference I ($CF_3$)$_2$($CH_3$)CCOF—Reference J

References

A. U.S. Pat. No. 4,031,124 (1977)
B. U.S. Pat. No. 3,933,767 (1976)
C. U.S. Pat. No. 3,852,326 (1974)
D. U.S. Pat. No. 3,113,967 (1963)
E. *J. Am. Chem. Soc.*, 84, 4275 (1962)
F. U.S. Pat. No. 4,172,016 (1979)
G. *J. F. Chem.*, 12 1–25 (1978)
H. *Chem. Abs.* 56, 312b (1961)
I. *Tetrahedron*, 27 3345–3355 (1971)
J. *J. F. Chem.*, 29 471–474 (1985)

Other of the alkanoyl halide starting materials can be prepared in analogous manner.

In addition, most of the starting alkanoyl halides can be prepared by electrochemical fluorination of precursor non-fluorinated compounds:

| Substituent on present starting material | Precursor substituent | Reference |
| --- | --- | --- |
| F | H | Hudlicky (following table) |
| $CF_3$ | $CH_3$ | " |
| $C_2F_5$ | $C_2H_5$ | " |
| n-$C_3F_7$ | n-$C_3H_7$ | " |

-continued

| Substituent on present starting material | Precursor substituent | Reference |
|---|---|---|
| OR$_f$ | OR | A |
|  | NR$_2$ | B, C, D |

Similarly, many of the alkanoyl halide starting materials are conveniently prepared by electrochemical fluorination of the precursors listed above, which are already partially fluorinated.

References

A. U.S. Pat. No. 2,594,272 (1952)
B. U.K. No. 666,733 (1952)
C. *Chem. Abs.*, 65, 2140g (1966)
D. *Chem. Abs.*, 62, 16089d (1965)

A general reference on electrochemical fluorination is "Chemistry of Organic Fluorine Compounds" by M. Hudlicky (Horwood Ltd., 1976), especially page 73.

I claim:

1. A method of inactivating an insect or arachnid which comprises applying to a locus of the insect or arachnid an effective amount of an active agent which is a compound selected from the group consisting of the formulae

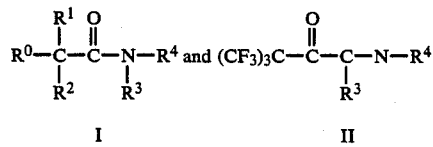

I   II wherein
R$^0$ represents
  bromo,
  chloro, or
  fluoro;
R$^1$ represents
  CF$_3$,
  C$_2$F$_5$,
  C$_3$F$_7$, or
  a n-, iso-, or sec-C$_4$F$_9$;
R$^2$ represents
  CF$_3$, C$_2$F$_5$, or C$_3$F$_7$, or,
  when R$^0$ represents fluoro, R$^2$ can additionally represent
  —OR$_f$,
  —N(R$_f$)$_2$,
  —CN,
  —CF$_2$—OR$_f$, or
  —CF$_2$—N(R$_f$)$_2$
  and each R$_f$ independently represents perfluoroloweralkyl of C$_1$-C$_4$ or, in —N(R$_f$)$_2$ both R$_f$ groups can be taken together with the N and constitute perfluoropyrrolidino, perfluoropiperidino, perfluoromorpholino, or N-(trifluoromethyl)perfluoropiperazino;
R$^3$ represents
  hydrogen, or
  methyl; and
R$^4$ represents
  5-nitro-2-pyridyl, thiocyanatophenyl bearing a single additional substituent which is fluoro, chloro, bromo, iodo, or nitro, or substituted aryl of the formula

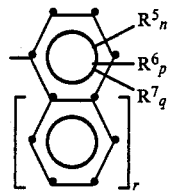

wherein each R$^5$ independently represents
  bromo,
  chloro, or
  fluoro;
each R$^6$ independently represents
  iodo,
  nitro,
  cyano,
  trifluoromethyl,
  fluorosulfonyl,
  methylsulfonyl,
  ethylsulfonyl,
  carbomethoxy, or
  carboethoxy;
R$^7$ represents
  methyl, or,
  when two R$^6$ moieties represent nitro at the 2- and 4-positions, R$^7$ can additionally represent C$_1$-C$_4$ alkoxy or C$_1$-C$_4$ alkylthio located at only the 3- or 5-position;
n represents 0-5; p represents 0-2 except that p can additionally represent 3 but only where two R$^6$ moieties represent nitro and a third R$^6$ moiety represents trifluoromethyl; q represents 0, or, when at least one R$^5$, nitro, or fluorosulfonyl group is present, 1;
r represents 0 or 1; and the sum of n, p, and q is:
  2-5 when each of p, q, and r is 0;
  2-3 when any one of p, q, or r is at least 1, except that when p is one and R$^6$ is 4-nitro, the sum of n and p can additionally be 1;
or a sodium, potassium, or ammonium salt of a foregoing compound, wherein ammonium is of the following formula

wherein each R$^8$ independently represents alkyl of C$_1$-C$_{20}$, benzyl, 2-hydroxyethyl, 2-hydroxypropyl, or 3-hydroxypropyl; and R$^9$ represents hydrogen or R$^8$, the total number of carbon atoms in all R$^8$ and R$^9$ moieties being from 12 to 60, except that when one or more R$^8$ groups are 2-hydroxyethyl, 2-hydroxypropyl, or 3-hydroxypropyl, the total number of carbon atoms in all R$^8$ and R$^9$ moieties can be from 6 to 60.

2. The method of claim 1 employing as active agent a compound of formula II or a salt thereof.

3. The method of claim 1 employing as active agent a compound of formula I or a salt thereof.

4. The method of claim 3 wherein $R^3=H$ and $R^4=2$-F, -Cl, -Br, or -I-4-nitrophenyl.

5. The method of claim 4 wherein $R^0=F$.

6. The method of claim 5 wherein $R^2=CF_3$, $C_2F_5$, or $C_3F_7$.

7. The method of claim 6 wherein the active agent is 2'-bromo-4'-nitro-2,3,3,3-tetrafluoro-2-(trifluoromethyl)propionanilide or a salt thereof.

8. The method of claim 6 wherein the active agent is 2'-chloro-4'-nitro-2,3,3,3-tetrafluoro-2-(trifluoromethyl)propionanilide or a salt thereof.

9. The method of claim 6 wherein the active agent is 2'-iodo-4'-nitro-2,3,3,3-tetrafluoro-2-(trifluoromethyl)-propionanilide or a salt thereof.

10. The method of claim 6 wherein the active agent is 2'-bromo-4'-nitro-2,3,3,4,4,4-hexafluoro-2-(trifluoromethyl)butyranilide or a salt thereof.

11. The method of claim 6 wherein the active agent is 2'-bromo-4'-nitro-2,3,3,4,4,4-hexafluoro-2-(pentafluoroethyl)butyranilide or a salt thereof.

12. The method of claim 6 wherein the active agent is 2'-bromo-4'-nitro-2,3,3,4,4,5,5,5-octafluoro-2-(trifluoromethyl)valeranilide or a salt thereof.

13. The method of claim 6 wherein the active agent is 2'-bromo-4'-nitro-2,3,3,4,4,5,5,5-octafluoro-2-(pentafluoroethyl)valeranilide or a salt thereof.

14. The method of claim 6 wherein the active agent is 2'-bromo-4'-nitro-2,3,3,4,4,5,5,5-octafluoro-2-(heptafluoropropyl)valeranilide or a salt thereof.

15. The method of claim 6 wherein the active agent is 2'-bromo-4'-nitro-2,3,3,4,4,5,5,6,6,6-decafluoro-2-(trifluoromethyl)hexananilide or a salt thereof.

16. The method of claim 6 wherein the active agent is 2'-bromo-4'-nitro-2,3,3,4,4,5,5,6,6,6-decafluoro-2-(pentafluoroethyl)hexananilide or a salt thereof.

17. The method of claim 5 wherein $R^2=OR_f$.

18. The method of claim 17 wherein the active agent is 2'-bromo-4'-nitro-2,3,3,3-tetrafluoro-2-(trifluoromethoxy)propionanilide or a salt thereof.

19. The method of claim 17 wherein the active agent is 2'-bromo-4'-nitro-2,3,3,3-tetrafluoro-2-(pentafluoroethoxy)propionanilide or a salt thereof.

20. The method of claim 17 wherein the active agent is 2'-bromo-4'-nitro-2,3,3,3-tetrafluoro-2-(heptafluoropropoxy)propionanilide or a salt thereof.

21. The method of claim 17 wherein the active agent is 2'-bromo-4'-nitro-2,3,3,3-tetrafluoro-2-(nonafluorobutoxy)propionanilide or a salt thereof.

22. The method of claim 5 wherein $R^2=-N(R_f)_2$.

23. The method of claim 22 wherein the active agent is 2'-bromo-4'-nitro-2,3,3,3-tetrafluoro-2-(octafluoromorpholino)propionanilide or a salt thereof.

24. The method of claim 3 wherein the active agent is 2',4'-dinitro-2,3,3,3-tetrafluoro-2-(trifluoromethyl)propionanilide or a salt thereof.

25. The method of claim 3 wherein the active agent is 2'-cyano-4'-nitro-2,3,3,3-tetrafluoro-2-(trifluoromethyl)propionanilide or a salt thereof.

26. The method of claim 3 wherein the active agent is 2'-(trifluoromethyl)-4'-nitro-2,3,3,3-tetrafluoro-2-(trifluoromethyl)propionanilide or a salt thereof.

27. The method of claim 3 wherein the active agent is 2'-methyl-4'-nitro-2,3,3,3-tetrafluoro-2-(trifluoromethyl)propionanilide or a salt thereof.

28. The method of claim 3 wherein the active agent is 2',5'-dichloro-4'-nitro-2,3,3,3-tetrafluoro-2-(trifluoromethyl)propionanilide or a salt thereof.

29. The method of claim 3 wherein the active agent is 2',6'-dichloro-4'-nitro-2,3,3,3-tetrafluoro-2-(trifluoromethyl)propionanilide or a salt thereof.

30. The method of claim 3 wherein the active agent is 2'-methyl-4'-nitro-5'-chloro-2,3,3,3-tetrafluoro-2-(trifluoromethyl)propionanilide or a salt thereof.

31. A method of claim 3 wherein $R^0$ represents chloro and both $R^1$ and $R^2$ represent trifluoromethyl.

32. The method of claim 3 wherein the insect or arachnid is a larval stage of corn rootworm.

33. The method of claim 32 wherein the active agent is 2'-bromo-4'-nitro-2,3,3,3-tetrafluoro-2-(trifluoromethyl)propionanilide or a salt thereof.

34. A formulation suitable for inactivating insects or arachnids which comprises an agriculturally acceptable adjuvant and an effective amount of an active agent which is a compound selected from the group consisting of the formulae

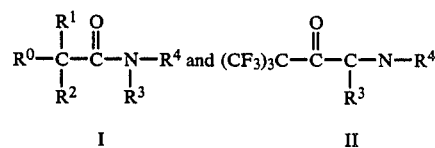

wherein
$R^0$ represents
  bromo,
  chloro, or
  fluoro;
$R^1$ represents
  $CF_3$,
  $C_2F_5$,
  $C_3F_7$, or
  a n-, iso-, or sec-$C_4F_9$;
$R^2$ represents
  $CF_3$, $C_2F_5$, or $C_3F_7$, or,
  when $R^0$ represents fluoro, $R^2$ can additionally represent
  $-OR_f$,
  $-N(R_f)_2$,
  $-CN$,
  $-CF_2-OR_f$, or
  $-CF_2-N(R_f)_2$
and each $R_f$ independently represents perfluoroloweralkyl of $C_1-C_4$ or, in $-N(R_f)_2$ both $R_f$ groups can be taken together with the N and constitute perfluoropyrrolidino, perfluoropiperidino, perfluoromorpholino, or N-(trifluoromethyl)perfluoropiperazino;
$R^3$ represents
  hydrogen, or
  methyl; and
$R^4$ represents
  5-nitro-2-pyridyl, thiocyanatophenyl bearing a single additional substituent which is fluoro, chloro, bromo, iodo, or nitro, or substituted aryl of the formula

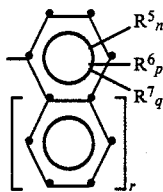

wherein each $R^5$ independently represents
  bromo,
  chloro, or
  fluoro;
each $R^6$ independently represents
  iodo,
  nitro,
  cyano,
  trifluoromethyl,
  fluorosulfonyl,
  methylsulfonyl,
  ethylsulfonyl,
  carbomethoxy, or
  carboethoxy;
$R^7$ represents
  methyl, or,
  when two $R^6$ moieties represent nitro at the 2- and 4-positions, $R^7$ can additionally represent $C_1$–$C_4$ alkoxy or $C_1$–$C_4$ alkylthio located at only the 3- or 5-position;
n represents 0–5; p represents 0–2 except that p can additionally represent 3 but only where two $R^6$ moieties represent nitro and a third $R^6$ moiety represents trifluoromethyl; q represents 0, or, when at least one $R^5$, nitro, or fluorosulfonyl group is present, 1; r represents 0 or 1; and the sum of n, p, and q is:
2–5 when each of p, q, and r is 0;
2–3 when any one of p, q, or r is at least 1, except that when p is one and $R^6$ is 4-nitro, the sum of n and p can additionally be 1;
or a sodium, potassium, or ammonium salt of a foregoing compound, wherein ammonium is of the following formula

wherein each $R^8$ independently represents alkyl of $C_1$–$C_{20}$, benzyl, 2-hydroxyethyl, 2-hydroxypropyl, or 3-hydroxypropyl; and $R^9$ represents hydrogen or $R^8$, the total number of carbon atoms in all $R^8$ and $R^9$ moieties being from 12 to 60, except that when one or more $R^8$ groups are 2-hydroxyethyl, 2-hydroxypropyl, or 3-hydroxypropyl, the total number of carbon atoms in all $R^8$ and $R^9$ moieties can be from 6 to 60.

35. The formulation of claim 34 wherein the active agent is a compound of formula II or a salt thereof.

36. The formulation of claim 34 wherein the active agent is a compound of formula I or a salt thereof.

37. The formulation of claim 36 wherein $R^3$=H and $R^4$=2-F, -Cl, -Br, or -I-4-nitrophenyl.

38. The formulation of claim 37 wherein $R^0$=R.

39. The formulation of claim 38 wherein $R^2$=$CF_3$, $C_2F_5$, or $C_3F_7$.

40. The formulation of claim 39 wherein the active agent is 2′-bromo-4′-nitro-2,3,3,3-tetrafluoro-2-(trifluoromethyl)propionanilide or a salt thereof.

41. The formulation of claim 39 wherein the active agent is 2′-chloro-4′-nitro-2,3,3,3-tetrafluoro-2-(trifluoromethyl)propionanilide or a salt thereof.

42. The formulation of claim 39 wherein the active agent is 2′-iodo-4′-nitro-2,3,3,3-tetrafluoro-2-(trifluoromethyl)propionanilide or a salt thereof.

43. The formulation of claim 39 wherein the active agent is 2′-bromo-4′-nitro-2,3,3,4,4,4-hexafluoro-2-(trifluoromethyl)butyranilide or a salt thereof.

44. The formulation of claim 39 wherein the active agent is 2′-bromo-4′-nitro-2,3,3,4,4,4-hexafluoro-2-(pentafluoroethyl)butyranilide or a salt thereof.

45. The formulation of claim 39 wherein the active agent is 2′-bromo-4′-nitro-b 2,3,3,4,4,5,5,5-octafluoro-2-(trifluoromethyl)valeranilide or a salt thereof.

46. The formulation of claim 39 wherein the active agent is 2′-bromo-4′-nitro-2,3,3,4,4,5,5,5-octafluoro-2-(pentafluoroethyl)valeranilide or a salt thereof.

47. The formulation of claim 39 wherein the active agent is 2′-bromo-4′-nitro-2,3,3,4,4,5,5,5-octafluoro-2-(heptafluoropropyl)valeranilide or a salt thereof.

48. The formulation of claim 39 wherein the active agent is 2′-bromo-4′-nitro-2,3,3,4,4,5,5,6,6,6-decafluoro-2-(trifluoromethyl)hexananilide or a salt thereof.

49. The formulation of claim 39 wherein the active agent is 2′-bromo-4′-nitro-2,3,3,4,4,5,5,6,6,6-decafluoro-2-(pentafluoroethyl)hexananilide or a salt thereof.

50. The formulation of claim 38 wherein $R^2$=$OR_f$ or a salt thereof.

51. The formulation of claim 50 wherein the active agent is 2′-bromo-4′-nitro-2,3,3,3-tetrafluoro-2-(trifluoromethoxy)propionanilide or a salt thereof.

52. The formulation of claim 50 wherein the active agent is 2′-bromo-4′-nitro-2,3,3,3-tetrafluoro-2-(pentafluoroethoxy)propionanilide or a salt thereof.

53. The formulation of claim 50 wherein the active agent is 2′-bromo-4′-nitro-2,3,3,3-tetrafluoro-2-(heptafluoropropoxy)propionanilide or a salt thereof.

54. The formulation of claim 50 wherein the active agent is 2′-bromo-4′-nitro-2,3,3,3-tetrafluoro-2-(nonafluorobutoxy)propionanilide or a salt thereof.

55. The formulation of claim 38 wherein $R^2$=—$N(R_f)_2$.

56. The formulation of claim 55 wherein the active agent is 2′-bromo-4′-nitro-2,3,3,3-tetrafluoro-2-(octafluoromorpholino)propionanilide or a salt thereof.

57. The formulation of claim 36 wherein the active agent is 2′,4′-dinitro-2,3,3,3-tetrafluoro-2-(trifluoromethyl)propionanilide or a salt thereof.

58. The formulation of claim 36 wherein the active agent is 2′-cyano-4′-nitro-2,3,3,3-tetrafluoro-2-(trifluoromethyl)propionanilide or a salt thereof.

59. The formulation of claim 36 wherein the active agent is 2′-(trifluoromethyl)-4′-nitro-2,3,3,3-tetrafluoro-2-(trifluoromethyl)propionanilide or a salt thereof.

60. The formulation of claim 36 wherein the active agent is 2′-methyl-4′-nitro-2,3,3,3-tetrafluoro-2-(trifluoromethyl)propionanilide or a salt thereof.

61. The formulation of claim 36 wherein the active agent is 2′,5′-dichloro-4′-nitro-2,3,3,3-tetrafluoro-2-(trifluoromethyl)propionanilide or a salt thereof.

62. The formulation of claim 36 wherein the active agent is 2′,6′-dichloro-4′-nitro-2,3,3,3-tetrafluoro-2-(trifluoromethyl)propionanilide or a salt thereof.

63. The formulation of claim 36 wherein the active agent is 2′-methyl-4′-nitro-5′-chloro-2,3,3,3-tetrafluoro-2-(trifluoromethyl)propionanilide or a salt thereof.

64. A formulation of claim 36 wherein $R^0$ represents chloro and both $R^1$ and $R^2$ represent trifluoromethyl.

* * * * *

UNITED STATES PATENT AND TRADEMARK OFFICE
CERTIFICATE OF CORRECTION

PATENT NO. : 4,826,841
DATED : May 2, 1989
INVENTOR(S) : Robert P. Gajewski

It is certified that error appears in the above—identified patent and that said Letters Patent is hereby corrected as shown below:

Column 4, line 14, "ethyl" should read --methyl--.

Column 14, line 29, delete "graphed".

Column 14, line 66, "2,3,3-tetrafluoro-" should read --2,3,3,3-tetrafluoro- --.

Column 30, line 12 and 13, "delay in emergence, injury on" should read --delay in emergence, and the Compound of Example 1 in addition showed crop injury on--.

Column 30, line 53, "Hypera postica 13 alfalfa weevil" should read --Hypera postica - alfalfa weevil--.

Column 35, lines 30-40, the structure which appears as

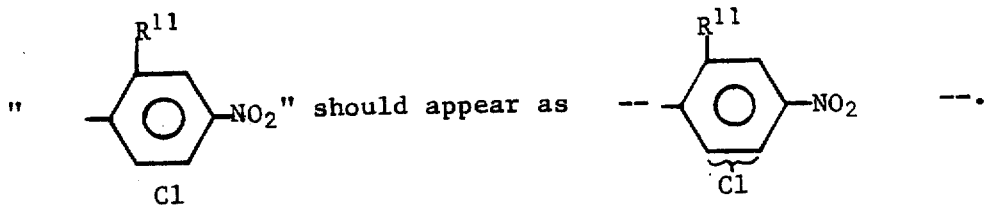

Column 47, line 26, "comtrol" should read --control--.

Column 56, line 50, "argriculturally" should read --agriculturally--.

Column 59, line 44, "conposition:" should read --composition:--.

Column 59, line 62, "1-aminonaphthalene, 2-amino-5-" should read --1-aminonaphthalene, or 2-amino-5- --.

UNITED STATES PATENT AND TRADEMARK OFFICE
CERTIFICATE OF CORRECTION

PATENT NO. : 4,826,841

DATED : May 2, 1989

INVENTOR(S) : Robert P. Gajewski

It is certified that error appears in the above—identified patent and that said Letters Patent is hereby corrected as shown below:

Column 61, lines 30-35, of claim 1, that portion of the formula which reads

"$(CF_3)_3C-\overset{\overset{O}{\|}}{C}-\underset{\underset{R^3}{|}}{C}-N-R^4$" should read --$(CF_3)_3C-\overset{\overset{O}{\|}}{C}-\underset{\underset{R^3}{|}}{C}-N-R^4$--.

Column 64, lines 22-30, of claim 34, that portion of the formula which reads

"$(CF_3)_3C-\overset{\overset{O}{\|}}{C}-\underset{\underset{R^3}{|}}{C}-N-R^4$" should read --$(CF_3)_3C-\overset{\overset{O}{\|}}{C}-\underset{\underset{R^3}{|}}{C}-N-R^4$--.

Column 65, line 66, in claim 38, "$R^0 = R$" should read --$R^0 = F$--.

Signed and Sealed this

Eighth Day of May, 1990

*Attest:*

HARRY F. MANBECK, JR.

*Attesting Officer*  *Commissioner of Patents and Trademarks*